US012571803B2

(12) United States Patent
Wilson et al.

(10) Patent No.: US 12,571,803 B2
(45) Date of Patent: *Mar. 10, 2026

(54) METHODS OF PRODUCING BODILY FLUID SAMPLES CONTAINING AN ANALYTICALLY QUANTIFIED AMOUNT OF PHOSPHORYLATED TAU PROTEIN

(71) Applicant: Quanterix Corporation, Billerica, MA (US)

(72) Inventors: David Wilson, Boxborough, MA (US); John Henrik Zetterberg, Molnlycke (SE); Kaj Blennow, Kungsbacka (SE); Jeffrey D. Randall, Canton, MA (US)

(73) Assignee: Quanterix Corporation, Billerica, MA (US)

( * ) Notice: Subject to any disclaimer, the term of this patent is extended or adjusted under 35 U.S.C. 154(b) by 873 days.

This patent is subject to a terminal disclaimer.

(21) Appl. No.: 17/674,968

(22) Filed: Feb. 18, 2022

(65) Prior Publication Data

US 2022/0244276 A1      Aug. 4, 2022

Related U.S. Application Data

(63) Continuation of application No. 16/522,237, filed on Jul. 25, 2019, now Pat. No. 11,275,092, which is a continuation of application No. 15/269,142, filed on Sep. 19, 2016, now Pat. No. 10,393,759, which is a continuation of application No. 14/111,326, filed as application No. PCT/US2012/033343 on Apr. 12, 2012, now abandoned.

(60) Provisional application No. 61/524,693, filed on Aug. 17, 2011, provisional application No. 61/474,315, filed on Apr. 12, 2011.

(51) Int. Cl.
*G01N 33/68*      (2006.01)
*G01N 33/543*      (2006.01)

(52) U.S. Cl.
CPC ... *G01N 33/6896* (2013.01); *G01N 33/54306* (2013.01); *G01N 2333/47* (2013.01); *G01N 2333/4709* (2013.01); *G01N 2800/28* (2013.01); *G01N 2800/52* (2013.01)

(58) Field of Classification Search
None
See application file for complete search history.

(56) References Cited

U.S. PATENT DOCUMENTS

| | | | |
|---|---|---|---|
| 3,712,986 A | 1/1973 | Collings | |
| 4,200,110 A | 4/1980 | Peterson et al. | |
| 4,232,119 A | 11/1980 | Carlsson et al. | |
| 4,631,211 A | 12/1986 | Houghten | |
| 4,780,421 A | 10/1988 | Kameda et al. | |
| 4,883,642 A | 11/1989 | Bisconte | |

| | | | |
|---|---|---|---|
| 4,907,037 A | 3/1990 | Boisde et al. | |
| 4,924,870 A | 5/1990 | Wlodarczyk et al. | |
| 4,962,037 A | 10/1990 | Jett et al. | |
| 5,026,159 A | 6/1991 | Allen et al. | |
| 5,028,535 A | 7/1991 | Buechler et al. | |
| 5,089,391 A | 2/1992 | Buechler et al. | |
| 5,091,300 A | 2/1992 | Hurni et al. | |
| 5,108,961 A | 4/1992 | Zhong et al. | |
| 5,152,816 A | 10/1992 | Berkey | |
| 5,190,857 A | 3/1993 | Allen et al. | |
| 5,196,306 A | 3/1993 | Bobrow et al. | |
| 5,213,962 A | 5/1993 | Van Nostrand et al. | |
| 5,234,814 A | 8/1993 | Card et al. | |
| 5,244,636 A | 9/1993 | Walt et al. | |
| 5,244,813 A | 9/1993 | Walt et al. | |
| 5,250,264 A | 10/1993 | Walt et al. | |
| 5,252,494 A | 10/1993 | Walt | |
| 5,262,332 A | 11/1993 | Selkoe et al. | |
| 5,270,165 A | 12/1993 | Van Nostrand et al. | |
| 5,298,741 A | 3/1994 | Walt et al. | |
| 5,315,375 A | 5/1994 | Allen | |
| 5,320,814 A | 6/1994 | Walt et al. | |
| 5,329,461 A | 7/1994 | Allen et al. | |
| 5,374,395 A | 12/1994 | Robinson et al. | |
| 5,405,783 A | 4/1995 | Pirrung et al. | |
| 5,441,870 A | 8/1995 | Seubert et al. | |
| 5,445,934 A | 8/1995 | Fodor et al. | |
| 5,468,846 A | 11/1995 | Ichikawa et al. | |

(Continued)

FOREIGN PATENT DOCUMENTS

| | | |
|---|---|---|
| AU | 199956253 B2 | 3/2000 |
| CA | 2258745 A1 | 12/1997 |

(Continued)

OTHER PUBLICATIONS

Quanterix P-TAU 231 (retrieved online https://www.quanterix.com/simoa-assay-kits/p-tau-231/#:~:text=Threonine%20231%20is%20one%20of,with%20specificity%20for%20brain%20injury on Apr. 29, 2025) (Year: 2025).*
Sjogren et al. Clinica Chimica Acta 332 (2003) 1-10. https://doi.org/10.1016/S0009-8981(03)00121-9 (Year: 2003).*
Hesse et al. Neuroscience Letters 297 (2001) 187-190 https://doi.org/10.1016/S0304-3940(00)01697-9 (Year: 2001).*
Office Action for U.S. Appl. No. 14/111,331 dated Jun. 29, 2020.
Appeal Brief for U.S. Appl. No. 14/111,331 as filed Feb. 26, 2021.
Examiner's Answer to Appeal Brief for U.S. Appl. No. 14/111,331 dated Jun. 17, 2021.

(Continued)

*Primary Examiner* — Gregory S Emch
*Assistant Examiner* — Fernando Ivich
(74) *Attorney, Agent, or Firm* — Wolf, Greenfield & Sacks, P.C.

(57)      ABSTRACT

The present invention, in some embodiments, generally relates to methods of determining a treatment protocol for and/or a prognosis of a patient's recovery from a brain injury. In some embodiments, the brain injury results from a hypoxic event. In some embodiments, methods are provided for determining a measure of the concentration of tau protein in a patient sample containing or suspected of containing tau protein.

22 Claims, 8 Drawing Sheets

(56) References Cited

U.S. PATENT DOCUMENTS

| | | | |
|---|---|---|---|
| 5,474,990 A | 12/1995 | Olney | |
| 5,488,567 A | 1/1996 | Allen et al. | |
| 5,492,812 A | 2/1996 | Vooheis | |
| 5,512,490 A | 4/1996 | Walt et al. | |
| 5,532,138 A | 7/1996 | Singh et al. | |
| 5,532,379 A | 7/1996 | Fujimoto | |
| 5,545,531 A | 8/1996 | Rava et al. | |
| 5,583,001 A | 12/1996 | Bobrow et al. | |
| 5,593,846 A | 1/1997 | Schenk et al. | |
| 5,620,850 A | 4/1997 | Bamdad et al. | |
| 5,633,972 A | 5/1997 | Walt et al. | |
| 5,690,894 A | 11/1997 | Pinkel et al. | |
| 5,700,637 A | 12/1997 | Southern | |
| 5,705,401 A | 1/1998 | Masters et al. | |
| 5,731,158 A | 3/1998 | Bobrow et al. | |
| 5,770,455 A | 6/1998 | Cargill et al. | |
| 5,807,522 A | 9/1998 | Brown et al. | |
| 5,814,524 A | 9/1998 | Walt et al. | |
| 5,843,779 A | 12/1998 | Vandermeeren et al. | |
| 5,858,648 A | 1/1999 | Steel et al. | |
| 5,861,257 A * | 1/1999 | Vandermeeren ....... C07K 16/18 | |
| | | | 435/7.1 |
| 5,869,266 A | 2/1999 | Wolozin et al. | |
| 5,885,529 A | 3/1999 | Babson et al. | |
| 5,900,481 A | 5/1999 | Lough et al. | |
| 5,976,817 A | 11/1999 | Davies-Heerema et al. | |
| 5,981,180 A | 11/1999 | Chandler et al. | |
| 5,981,208 A | 11/1999 | Tamburini et al. | |
| 6,001,564 A | 12/1999 | Bergeron et al. | |
| 6,007,690 A | 12/1999 | Nelson et al. | |
| 6,013,445 A | 1/2000 | Albrecht et al. | |
| 6,023,540 A | 2/2000 | Walt et al. | |
| 6,133,436 A | 10/2000 | Koster et al. | |
| 6,143,496 A | 11/2000 | Brown et al. | |
| 6,156,270 A | 12/2000 | Buechler | |
| 6,174,695 B1 | 1/2001 | Hammock et al. | |
| 6,210,910 B1 | 4/2001 | Walt et al. | |
| 6,266,459 B1 | 7/2001 | Walt et al. | |
| 6,285,807 B1 | 9/2001 | Walt et al. | |
| 6,327,410 B1 | 12/2001 | Walt et al. | |
| 6,329,139 B1 | 12/2001 | Nova et al. | |
| 6,368,874 B1 | 4/2002 | Gallop et al. | |
| 6,377,721 B1 | 4/2002 | Walt et al. | |
| 6,388,746 B1 | 5/2002 | Eriksson et al. | |
| 6,396,995 B1 | 5/2002 | Stuelpnagel et al. | |
| 6,406,845 B1 | 6/2002 | Walt et al. | |
| 6,432,630 B1 | 8/2002 | Blankenstein | |
| 6,482,593 B2 | 11/2002 | Walt et al. | |
| 6,495,335 B2 | 12/2002 | Chojkier et al. | |
| 6,582,908 B2 | 6/2003 | Fodor et al. | |
| 6,599,331 B2 | 7/2003 | Chandler et al. | |
| 6,602,702 B1 | 8/2003 | McDevitt et al. | |
| 6,620,584 B1 | 9/2003 | Chee et al. | |
| 6,635,452 B1 | 10/2003 | Monforte et al. | |
| 6,667,159 B1 | 12/2003 | Walt et al. | |
| 6,670,137 B2 | 12/2003 | VanMechelen et al. | |
| 6,680,173 B2 | 1/2004 | Vanmechelen et al. | |
| 6,713,309 B1 | 3/2004 | Anderson et al. | |
| 6,714,303 B2 | 3/2004 | Ivarsson | |
| 6,811,988 B2 | 11/2004 | Chojkier et al. | |
| 6,821,449 B2 | 11/2004 | Caplen et al. | |
| 6,838,051 B2 | 1/2005 | Marquiss et al. | |
| 6,858,394 B1 | 2/2005 | Chee et al. | |
| 6,859,570 B2 | 2/2005 | Walt et al. | |
| 6,878,345 B1 | 4/2005 | Astle | |
| 6,929,924 B2 | 8/2005 | Bouanani et al. | |
| 6,942,968 B1 | 9/2005 | Dickinson et al. | |
| 6,943,034 B1 | 9/2005 | Winkler et al. | |
| 6,991,939 B2 | 1/2006 | Walt et al. | |
| 6,999,657 B2 | 2/2006 | Walt | |
| 7,041,481 B2 | 5/2006 | Anderson et al. | |
| 7,056,746 B2 | 6/2006 | Seul et al. | |
| 7,060,431 B2 | 6/2006 | Chee et al. | |
| 7,107,092 B2 | 9/2006 | Goldstein et al. | |
| 7,115,884 B1 | 10/2006 | Walt et al. | |
| 7,211,390 B2 | 5/2007 | Rothberg et al. | |
| 7,244,559 B2 | 7/2007 | Rothberg et al. | |
| 7,250,267 B2 | 7/2007 | Walt et al. | |
| 7,264,929 B2 | 9/2007 | Rothberg et al. | |
| 7,348,181 B2 | 3/2008 | Walt et al. | |
| 7,442,516 B2 | 10/2008 | Ohno et al. | |
| 7,480,433 B2 | 1/2009 | Walt et al. | |
| 7,572,581 B2 | 8/2009 | Gelfand et al. | |
| 7,651,841 B2 | 1/2010 | Song et al. | |
| 7,655,424 B2 | 2/2010 | Jackowski | |
| 7,749,700 B2 | 7/2010 | Baird et al. | |
| 7,759,062 B2 | 7/2010 | Allawi et al. | |
| 7,776,553 B2 | 8/2010 | Love et al. | |
| 7,838,250 B1 | 11/2010 | Goix et al. | |
| 8,222,047 B2 | 7/2012 | Duffy et al. | |
| 8,236,574 B2 | 8/2012 | Duffy et al. | |
| 8,415,171 B2 | 4/2013 | Rissin et al. | |
| 8,460,878 B2 | 6/2013 | Walt et al. | |
| 8,460,879 B2 | 6/2013 | Walt et al. | |
| 8,492,098 B2 | 7/2013 | Walt et al. | |
| 8,592,221 B2 | 11/2013 | Fraden et al. | |
| 8,846,415 B2 | 9/2014 | Duffy et al. | |
| 9,110,025 B2 | 8/2015 | Rissin et al. | |
| 9,310,360 B2 | 4/2016 | Duffy et al. | |
| 9,395,359 B2 | 7/2016 | Walt et al. | |
| 9,482,622 B2 | 11/2016 | Sato et al. | |
| 9,482,662 B2 | 11/2016 | Duffy et al. | |
| 9,551,663 B2 | 1/2017 | Rissin et al. | |
| 9,562,897 B2 | 2/2017 | Samuels et al. | |
| 9,678,068 B2 | 6/2017 | Duffy et al. | |
| 9,809,838 B2 | 11/2017 | Walt et al. | |
| 9,846,155 B2 | 12/2017 | Rissin et al. | |
| 9,932,626 B2 | 4/2018 | Duffy et al. | |
| 9,952,237 B2 | 4/2018 | Fournier et al. | |
| 10,261,089 B2 | 4/2019 | Walt et al. | |
| 10,357,772 B2 | 7/2019 | Fraden et al. | |
| 10,393,759 B2 | 8/2019 | Wilson et al. | |
| 10,640,814 B2 | 5/2020 | Duffy et al. | |
| 10,725,032 B2 | 7/2020 | Duffy et al. | |
| 10,761,090 B2 | 9/2020 | Samuels et al. | |
| 10,960,397 B2 | 3/2021 | Fraden et al. | |
| 10,989,713 B2 | 4/2021 | Rissin et al. | |
| 11,112,415 B2 | 9/2021 | Fournier et al. | |
| 11,187,702 B2 | 11/2021 | Link et al. | |
| 11,275,092 B2 | 3/2022 | Wilson et al. | |
| 11,434,264 B2 | 9/2022 | Pollock et al. | |
| 11,619,631 B2 | 4/2023 | Duffy et al. | |
| 11,874,279 B2 | 1/2024 | Walt et al. | |
| 11,977,087 B2 | 5/2024 | Fournier et al. | |
| 12,019,072 B2 | 6/2024 | Rissin et al. | |
| 12,111,324 B2 | 10/2024 | Hrusovsky et al. | |
| 12,130,294 B2 | 10/2024 | Hrusovsky et al. | |
| 12,235,267 B2 | 2/2025 | Duffy et al. | |
| 2001/0018191 A1 | 8/2001 | Merken et al. | |
| 2002/0001857 A1 | 1/2002 | Vandermeeren et al. | |
| 2002/0009391 A1 | 1/2002 | Marquiss et al. | |
| 2002/0019016 A1 | 2/2002 | Vanmechelen et al. | |
| 2002/0058332 A1 | 5/2002 | Quake et al. | |
| 2002/0086009 A1 | 7/2002 | Ishiguro et al. | |
| 2002/0090650 A1 | 7/2002 | Empedocles et al. | |
| 2002/0122612 A1 | 9/2002 | Walt et al. | |
| 2002/0137112 A1 | 9/2002 | Chojkier et al. | |
| 2002/0157122 A1 | 10/2002 | Wong et al. | |
| 2002/0188106 A1 | 12/2002 | Mandelkow et al. | |
| 2003/0027126 A1 | 2/2003 | Walt et al. | |
| 2003/0091475 A1 | 5/2003 | Yu et al. | |
| 2003/0096227 A1 | 5/2003 | Shinitzky et al. | |
| 2003/0096243 A1 | 5/2003 | Busa | |
| 2003/0104361 A1 | 6/2003 | Weininger et al. | |
| 2003/0104488 A1 | 6/2003 | Chojkier et al. | |
| 2003/0124599 A1 | 7/2003 | Chen et al. | |
| 2003/0138972 A1 | 7/2003 | Vandermeeren et al. | |
| 2003/0143580 A1 | 7/2003 | Straus et al. | |
| 2003/0143760 A1 | 7/2003 | Vandermeeren et al. | |
| 2003/0165575 A1 | 9/2003 | Iqbal et al. | |
| 2003/0194742 A1 | 10/2003 | Vanmechelen et al. | |
| 2003/0198573 A1 | 10/2003 | Forood et al. | |
| 2004/0013647 A1 | 1/2004 | Solomon et al. | |
| 2004/0014142 A1 | 1/2004 | Vanmechelen et al. | |

(56)     References Cited

U.S. PATENT DOCUMENTS

| | | |
|---|---|---|
| 2004/0018561 A1 | 1/2004 | Decrescenzo et al. |
| 2004/0038426 A1 | 2/2004 | Manalis |
| 2004/0038430 A1 | 2/2004 | Vandermeeren et al. |
| 2004/0043502 A1 | 3/2004 | Song et al. |
| 2004/0053322 A1 | 3/2004 | McDevitt et al. |
| 2004/0071599 A1 | 4/2004 | Rusch et al. |
| 2004/0072278 A1 | 4/2004 | Chou et al. |
| 2004/0086426 A1 | 5/2004 | Vann et al. |
| 2004/0101918 A1 | 5/2004 | Cauci |
| 2004/0132680 A1 | 7/2004 | Wong et al. |
| 2004/0142386 A1 | 7/2004 | Rigler et al. |
| 2004/0166536 A1 | 8/2004 | Kerkman et al. |
| 2004/0219509 A1 | 11/2004 | Valkirs et al. |
| 2004/0248325 A1 | 12/2004 | Bukusoglu |
| 2004/0253624 A1 | 12/2004 | Smith et al. |
| 2004/0253643 A1 | 12/2004 | Seubert et al. |
| 2004/0259237 A1 | 12/2004 | Kellogg et al. |
| 2005/0042221 A1 | 2/2005 | Chojkier et al. |
| 2005/0053996 A1 | 3/2005 | Tong |
| 2005/0069968 A1 | 3/2005 | Seubert et al. |
| 2005/0112634 A1 | 5/2005 | Woudenberg et al. |
| 2005/0112655 A1 | 5/2005 | Banerjee et al. |
| 2005/0118574 A1 | 6/2005 | Chandler et al. |
| 2005/0124016 A1 | 6/2005 | LaDu et al. |
| 2005/0129581 A1 | 6/2005 | McBride et al. |
| 2005/0130173 A1 | 6/2005 | Leamon et al. |
| 2005/0130188 A1 | 6/2005 | Walt et al. |
| 2005/0131650 A1 | 6/2005 | Andersson et al. |
| 2005/0164289 A1 | 7/2005 | Quate et al. |
| 2005/0169925 A1 | 8/2005 | Bardroff et al. |
| 2005/0175626 A1 | 8/2005 | Delacourte et al. |
| 2005/0181460 A1 | 8/2005 | Ohno et al. |
| 2005/0221281 A1 | 10/2005 | Ho |
| 2005/0226780 A1 | 10/2005 | Sandell et al. |
| 2005/0244308 A1 | 11/2005 | Tanaami et al. |
| 2005/0244890 A1 | 11/2005 | Davies et al. |
| 2005/0255491 A1 | 11/2005 | Lee et al. |
| 2005/0266433 A1 | 12/2005 | Kapur et al. |
| 2006/0006067 A1 | 1/2006 | Unger |
| 2006/0013543 A1 | 1/2006 | Walt et al. |
| 2006/0024759 A1 | 2/2006 | Holtzman et al. |
| 2006/0040297 A1 | 2/2006 | Leamon et al. |
| 2006/0061755 A1 | 3/2006 | Turner et al. |
| 2006/0068409 A1 | 3/2006 | Phan et al. |
| 2006/0078998 A1 | 4/2006 | Puskas et al. |
| 2006/0084183 A1 | 4/2006 | Henricksen |
| 2006/0139635 A1 | 6/2006 | Kersey et al. |
| 2006/0205024 A1 | 9/2006 | Rogers et al. |
| 2007/0040095 A1 | 2/2007 | Walt et al. |
| 2007/0059754 A1 | 3/2007 | Kordunsky et al. |
| 2007/0074972 A1 | 4/2007 | Nassef et al. |
| 2007/0116607 A1 | 5/2007 | Wang et al. |
| 2007/0154480 A1 | 7/2007 | Schenk et al. |
| 2007/0259381 A1 | 11/2007 | Rissin et al. |
| 2007/0259385 A1 | 11/2007 | Rissin et al. |
| 2007/0259448 A1 | 11/2007 | Rissin et al. |
| 2008/0032324 A1 | 2/2008 | Walt et al. |
| 2008/0038761 A1 | 2/2008 | Beernink et al. |
| 2008/0039343 A1 | 2/2008 | Guire et al. |
| 2008/0064113 A1 | 3/2008 | Goix et al. |
| 2008/0118924 A1 | 5/2008 | Buechler |
| 2008/0131422 A1 | 6/2008 | Sugimura et al. |
| 2008/0131907 A1 | 6/2008 | Wang et al. |
| 2008/0199879 A1 | 8/2008 | Takayama et al. |
| 2008/0234311 A1 | 9/2008 | Li et al. |
| 2008/0248962 A1 | 10/2008 | Kim et al. |
| 2008/0254482 A1 | 10/2008 | Mattoon et al. |
| 2008/0269069 A1 | 10/2008 | Bacher et al. |
| 2008/0299111 A1 | 12/2008 | Delacourte et al. |
| 2009/0022825 A1 | 1/2009 | Kerkman et al. |
| 2009/0036324 A1 | 2/2009 | Fan et al. |
| 2009/0068639 A1 | 3/2009 | Aizawa et al. |
| 2009/0087860 A1 | 4/2009 | Todd et al. |
| 2009/0142755 A1 | 6/2009 | Albitar |
| 2009/0149341 A1 | 6/2009 | Walt et al. |
| 2009/0156425 A1 | 6/2009 | Walt et al. |
| 2009/0170728 A1 | 7/2009 | Walt et al. |
| 2009/0239308 A1 | 9/2009 | Dube et al. |
| 2009/0254180 A1 | 10/2009 | Pazanowski et al. |
| 2009/0289834 A1 | 11/2009 | Devensky |
| 2009/0307772 A1 | 12/2009 | Markham et al. |
| 2010/0022414 A1 | 1/2010 | Link et al. |
| 2010/0075355 A1 | 3/2010 | Duffy et al. |
| 2010/0075407 A1 | 3/2010 | Duffy et al. |
| 2010/0075439 A1 | 3/2010 | Duffy et al. |
| 2010/0075862 A1 | 3/2010 | Duffy et al. |
| 2010/0112727 A1* | 5/2010 | Todd ................ G01N 33/54333 436/536 |
| 2010/0124552 A1 | 5/2010 | Klein et al. |
| 2010/0136593 A1 | 6/2010 | Jackowski |
| 2010/0140289 A1 | 6/2010 | Knobel et al. |
| 2010/0189338 A1 | 7/2010 | Lin et al. |
| 2010/0192573 A1 | 8/2010 | Hamilton et al. |
| 2010/0204335 A1 | 8/2010 | Beddingfield et al. |
| 2010/0225913 A1 | 9/2010 | Trainer |
| 2010/0227379 A1 | 9/2010 | Wo et al. |
| 2010/0267582 A1 | 10/2010 | Baird et al. |
| 2010/0329929 A1 | 12/2010 | Goix et al. |
| 2011/0037463 A1 | 2/2011 | Bertacco et al. |
| 2011/0039278 A1 | 2/2011 | Pieribone |
| 2011/0183330 A1 | 7/2011 | Lo et al. |
| 2011/0195852 A1 | 8/2011 | Walt et al. |
| 2011/0212462 A1 | 9/2011 | Duffy et al. |
| 2011/0212537 A1 | 9/2011 | Rissin et al. |
| 2011/0212848 A1 | 9/2011 | Duffy et al. |
| 2011/0245097 A1 | 10/2011 | Rissin et al. |
| 2012/0070379 A1 | 3/2012 | Black et al. |
| 2012/0183967 A1 | 7/2012 | Dressman et al. |
| 2012/0196774 A1 | 8/2012 | Fournier et al. |
| 2012/0214160 A1 | 8/2012 | Deng et al. |
| 2012/0277114 A1 | 11/2012 | Duffy et al. |
| 2012/0289428 A1 | 11/2012 | Duffy et al. |
| 2013/0165342 A1 | 6/2013 | Rissin et al. |
| 2013/0345078 A1 | 12/2013 | Walt et al. |
| 2014/0086836 A1 | 3/2014 | Burnham et al. |
| 2014/0094386 A1 | 4/2014 | Wilson et al. |
| 2014/0227720 A1 | 8/2014 | Wilson et al. |
| 2014/0302532 A1 | 10/2014 | Wilson et al. |
| 2015/0185232 A1 | 7/2015 | Keane et al. |
| 2015/0233905 A1 | 8/2015 | Walt et al. |
| 2015/0353997 A1 | 12/2015 | Duffy et al. |
| 2015/0355182 A1 | 12/2015 | Rissin et al. |
| 2016/0123969 A1 | 5/2016 | Rissin et al. |
| 2016/0258959 A1 | 9/2016 | Wilson et al. |
| 2017/0038390 A1 | 2/2017 | Walt et al. |
| 2017/0159104 A1 | 6/2017 | Walt et al. |
| 2017/0160292 A1 | 6/2017 | Wilson et al. |
| 2018/0003703 A1 | 1/2018 | Duffy et al. |
| 2018/0017552 A1 | 1/2018 | Duffy et al. |
| 2018/0037614 A1 | 2/2018 | Pollock et al. |
| 2018/0224451 A1 | 8/2018 | Rissin et al. |
| 2018/0306830 A1 | 10/2018 | Fournier et al. |
| 2018/0363038 A1 | 12/2018 | Duffy et al. |
| 2019/0293655 A1 | 9/2019 | Walt et al. |
| 2019/0302109 A1 | 10/2019 | Duffy et al. |
| 2020/0032326 A1 | 1/2020 | Walt et al. |
| 2020/0123592 A1 | 4/2020 | Díaz-Mochón et al. |
| 2020/0124620 A1 | 4/2020 | Wilson et al. |
| 2020/0271643 A1 | 8/2020 | Wilson et al. |
| 2020/0393457 A1 | 12/2020 | Duffy et al. |
| 2021/0311058 A1 | 10/2021 | Rissin et al. |
| 2022/0034917 A1 | 2/2022 | Fournier et al. |
| 2022/0042995 A1 | 2/2022 | Link et al. |
| 2022/0050108 A1 | 2/2022 | Link et al. |
| 2022/0099678 A1 | 3/2022 | Walt et al. |
| 2022/0229073 A1 | 7/2022 | Hrusovsky et al. |
| 2022/0229074 A1 | 7/2022 | Wilson et al. |
| 2024/0201175 A1 | 6/2024 | Wilson et al. |
| 2025/0208150 A1 | 6/2025 | Wilson et al. |

FOREIGN PATENT DOCUMENTS

| | | |
|---|---|---|
| CN | 1635146 A | 7/2005 |
| CN | 1928561 A | 3/2007 |

(56) References Cited

FOREIGN PATENT DOCUMENTS

| CN | 1950520 | A | 4/2007 |
|----|---------|---|--------|
| CN | 101351564 | A | 1/2009 |
| CN | 101529227 | A | 9/2009 |
| CN | 101541974 | A | 9/2009 |
| DE | 19540098 | A1 | 4/1997 |
| EP | 0 805 215 | A2 | 11/1997 |
| EP | 1 160 256 | A2 | 12/2001 |
| EP | 1 180 679 | A1 | 2/2002 |
| EP | 1 259 810 | A2 | 11/2002 |
| EP | 1 298 436 | A2 | 4/2003 |
| EP | 1 721 657 | A1 | 11/2006 |
| EP | 1 978 035 | A1 | 10/2008 |
| EP | 2 267 451 | A2 | 12/2010 |
| EP | 2 324 360 | B1 | 1/2018 |
| JP | 2001-269196 | A | 10/2001 |
| JP | 2002-506200 | A | 2/2002 |
| JP | 2002-525587 | A | 8/2002 |
| JP | 2002-526743 | A | 8/2002 |
| JP | 2004-354164 | A | 12/2004 |
| JP | 2005-518553 | A | 6/2005 |
| JP | 2006-511792 | A | 4/2006 |
| WO | WO 88/05533 | A1 | 7/1988 |
| WO | WO 91/06559 | A1 | 5/1991 |
| WO | WO 93/06121 | A1 | 4/1993 |
| WO | WO 93/24517 | A2 | 12/1993 |
| WO | WO 95/19178 | A1 | 7/1995 |
| WO | WO 95/25116 | A1 | 9/1995 |
| WO | WO 95/32425 | A1 | 11/1995 |
| WO | WO 95/35506 | A2 | 12/1995 |
| WO | WO 96/04309 | A1 | 2/1996 |
| WO | WO 97/27326 | A1 | 7/1997 |
| WO | WO 98/50782 | A2 | 11/1998 |
| WO | WO 99/45357 | A2 | 9/1999 |
| WO | WO 99/58948 | A2 | 11/1999 |
| WO | WO 00/04372 | A1 | 1/2000 |
| WO | WO 00/14546 | A1 | 3/2000 |
| WO | WO 00/47996 | A2 | 8/2000 |
| WO | WO 01/57520 | A2 | 8/2001 |
| WO | WO 01/90757 | A1 | 11/2001 |
| WO | WO 02/46222 | A2 | 6/2002 |
| WO | WO 02/47466 | A2 | 6/2002 |
| WO | WO 03/054142 | A2 | 7/2003 |
| WO | WO 03/073817 | A1 | 9/2003 |
| WO | WO 2004/043226 | A2 | 5/2004 |
| WO | WO 2004/065000 | A1 | 8/2004 |
| WO | WO 2004/083443 | A1 | 9/2004 |
| WO | WO 2005/011599 | A2 | 2/2005 |
| WO | WO 2005/019419 | A2 | 3/2005 |
| WO | WO 2005/023414 | A1 | 3/2005 |
| WO | WO 2005/033283 | A2 | 4/2005 |
| WO | WO 2005/047484 | A2 | 5/2005 |
| WO | WO 2005/054431 | A2 | 6/2005 |
| WO | WO 2005/075507 | A1 | 8/2005 |
| WO | WO 2005/095262 | A1 | 10/2005 |
| WO | WO 2005/123775 | A1 | 12/2005 |
| WO | WO 2006/007726 | A1 | 1/2006 |
| WO | WO 2006/055739 | A2 | 5/2006 |
| WO | WO 2006/078289 | A2 | 7/2006 |
| WO | WO 2006/102297 | A1 | 9/2006 |
| WO | WO 2006/103116 | A1 | 10/2006 |
| WO | WO 2006/108180 | A2 | 10/2006 |
| WO | WO 2007/016357 | A1 | 2/2007 |
| WO | WO 2007/044091 | A2 | 4/2007 |
| WO | WO 2007/044974 | A2 | 4/2007 |
| WO | WO 2007/050359 | A2 | 5/2007 |
| WO | WO 2007/064972 | A2 | 6/2007 |
| WO | WO 2007/068429 | A1 | 6/2007 |
| WO | WO 2007/081385 | A2 | 7/2007 |
| WO | WO 2007/081386 | A2 | 7/2007 |
| WO | WO 2007/081387 | A1 | 7/2007 |
| WO | WO 2007/082750 | A1 | 7/2007 |
| WO | WO 2007/084192 | A2 | 7/2007 |
| WO | WO 2007/090126 | A2 | 8/2007 |
| WO | WO 2007/098148 | A2 | 8/2007 |
| WO | WO 2007/106762 | A2 | 9/2007 |
| WO | WO 2007/114947 | A2 | 10/2007 |
| WO | WO 2007/136614 | A2 | 11/2007 |
| WO | WO 2008/027017 | A1 | 3/2008 |
| WO | WO 2008/034016 | A2 | 3/2008 |
| WO | WO 2008/048371 | A2 | 4/2008 |
| WO | WO 2008/060364 | A2 | 5/2008 |
| WO | WO 2008/067464 | A2 | 6/2008 |
| WO | WO 2008/081008 | A1 | 7/2008 |
| WO | WO 2008/150946 | A1 | 12/2008 |
| WO | WO 2008/156622 | A1 | 12/2008 |
| WO | WO 2009/004494 | A2 | 1/2009 |
| WO | WO 2009/029073 | A1 | 3/2009 |
| WO | WO 2009/134942 | A1 | 11/2009 |
| WO | WO 2009/156747 | A3 | 12/2009 |
| WO | WO 2010/039180 | A2 | 4/2010 |
| WO | WO 2011/032155 | A2 | 3/2011 |
| WO | WO 2011/109364 | A2 | 9/2011 |
| WO | WO 2011/109372 | A1 | 9/2011 |
| WO | WO 2013/103475 | A2 | 7/2013 |
| WO | WO 2016/115256 | A1 | 7/2016 |
| WO | WO 2016/130923 | A1 | 8/2016 |
| WO | WO 2018/222585 | A2 | 12/2018 |
| WO | WO 2019/060607 | A1 | 3/2019 |

OTHER PUBLICATIONS

Reply Brief for U.S. Appl. No. 14/111,331 as filed Aug. 16, 2021.

Appeal Decision for U.S. Appl. No. 14/111,331 dated Nov. 16, 2022.

Office Action for U.S. Appl. No. 14/111,331 dated Sep. 21, 2023.

Hadd et al., Microchip device for performing enzyme assays. Anal Chem. Sep. 1, 1997;69(17):3407-12. doi: 10.1021/ac970192p.

Grate et al., Advances in assays and analytical approaches for botulinum-toxin detection. TrAC, Trends Anal Chem. Nov. 2010;29(10):1137-56.

Li et al., Hydrogel droplet microarrays with trapped antibody-functionalized beads for multiplexed protein analysis. Lab Chip. Feb. 7, 2011;11(3):528-34. doi: 10.1039/c0lc00291g. Epub Dec. 1, 2010.

International Search Report and Written Opinion mailed Nov. 29, 2012 for Application No. PCT/US2012/033338.

International Preliminary Report on Patentability mailed Oct. 24, 2013 for Application No. PCT/US2012/033338.

International Search Report and Written Opinion mailed Oct. 29, 2012 for Application No. PCT/US2012/033343.

International Preliminary Report on Patentability mailed Oct. 24, 2013 for Application No. PCT/US2012/033343.

Office Communication for U.S. Appl. No. 14/111,331 mailed Dec. 12, 2019 and claims pending.

[No Author Listed], bioMérieux and Quanterix Sign Strategic Partnership in Ultrasensitive and Multiplex Immunoassays. Quanterix Press Release. Nov. 15, 2012. 2 pages.

[No Author Listed], Does Brain Hypoxia Help Kick Off Alzheimer's Pathology? Alzheimer Research Forum. Dec. 16, 2011. http://www.alzforum.org/new/detailprint.asp?id=3002 [last accessed Jan. 30, 2012]. 4 pages.

[No Author Listed], Novel test following prostate surgery could detect cancer recurrence earlier. AACR Press Release. Sep. 29, 2010. Last accessed at http://www.aacr.org/home/public--media/aacr-press-releases.aspx?d=2072 on Jan. 31, 2012. 2 pages.

[No Author Listed], Pittcon Announces 2010 Technical Program: Webcast of Selected Symposia. Press Release. Oct. 15, 2009. http://archive.constantcontact.com/fs033/1102032821298/archive/1102745632000.html [last accessed Jan. 31, 2012]. 2 pages.

[No Author Listed], Quanterix and STRATEC Announce Strategic Partnership. Quanterix Press Release. Aug. 16, 2011. 2 pages.

[No Author Listed], Quanterix Announces Commercial Availability of its Simoa Single Molecule Array Technology. Quanterix Press Release. Jul. 30, 2013. 2 pages.

[No Author Listed], Quanterix corporation awarded $185,000 grant from the National Cancer Institute. Quanterix Press Release. Sep. 30, 2008. Last accessed at http://www.quanterix.com/news/pressReleases/SBIR1Grant.html on Jan. 31, 2012. 1 page.

(56)                   References Cited

OTHER PUBLICATIONS

[No Author Listed], Quanterix corporation raises $15 million in series A financing. Quanterix Press Release. Aug. 25, 2008. Last accessed at http://www.quanterix.com/news/pressReleases/seriesAFunding.html on Jan. 31, 2012. 2 pages.

[No Author Listed], Quanterix Digital ELISA Measures Low Abundance Biomarkers of Inflammation in Crohn's Disease. Quanterix Press Release. Aug. 19, 2011. Last accessed at http://www.quanterix.com/events-news/press-releases/item/142-quanterix-digital-elisa-measures-low-abundance-biomarkers-of-inflammation-in-crohn's-disease on Sep. 20, 2012.

[No Author Listed], Quanterix Discovers Link Between Heart Attack-induced Hypoxia and Suspected Alzheimer's Disease Pathway. Quanterix Press Release. Apr. 12, 2011. Last accessed at http://www.quanterix.com/events-news/press-releases/item/146-quanterix-discovers-link-between-heart-attack-induced-hypoxia-and-suspected-alzheimer's-disease-pathway on Sep. 20, 2012.

[No Author Listed], Quanterix Launches Multiplexed Single Molecule Immunoassay Technology to Improve Diagnosis and Potential Treatment of Complex Diseases. Quanterix Press Release. Sep. 17, 2013. 2 pages.

[No Author Listed], Quanterix to Present Poster Session on Blood-based Brain Biomarker Measurements of Sports Related Brain Injury at Neuroscience. Quanterix Press Release. Nov. 4, 2013. 1 page.

[No Author Listed], Quanterix's Simoa technology to detect blood biomarker for concussion in hockey players. Quanterix Press Release. Mar. 14, 2014. 1 page.

[No Author Listed], Quanterix's Ultrasensitive Simoa™ Technology Demonstrates Equivalence with NAT and 3,000x Improvement in Sensitivity over Conventional Immunoassays for HIV Detection. Quanterix Press Release. Oct. 11, 2012. 1 page.

[No Author Listed], Quanterix's Ultrasensitive Simoa™ Technology Forges New Ground with Direct Detection of Genomic DNA in Human Blood and River Water. Quanterix Press Release. Jan. 22, 2013. 2 pages.

[No Author Listed], Scientific Principle of Simoa™ (Single Molecule Array) Technology. Whitepaper 1.0. Jul. 19, 2013. 2 pages.

[No Author Listed], Single molecule arrays for digital detection in complex samples. Quanterix Corporation. IQT Technology Focus Day. Mar. 25, 2010. PowerPoint presentation. 30 pages.

[No Author Listed], Ultrasensitive Tau Assay Enables Quantification of Neuronal Biomarker in Blood for the First Time. Whitepaper 3.0. Quanterix. Oct. 8, 2013. 4 pages.

Adams et al., Encoded fiber-optic microsphere arrays for probing protein-carbohydrate interactions. Angewandte Chemie. 2003; 115:5475-5478.

Agrawal et al., Nanometer-scale mapping and single-molecule detection with color-coded nanoparticle probes. Proc Natl Acad Sci U S A. Mar. 4, 2008;105(9):3298-303. Epub Feb. 27, 2008.

Agrawal et al., Single-bead immunoassays using magnetic microparticles and spectral-shifting quantum dots. J Agric Food Chem. May 16, 2007; 55(10):3778-82. Epub Apr. 25, 2007.

Ahn et al., Detection of *Salmonella* spp. Using microsphere-based, fiber-optic DNA microarrays. Anal Chem. Aug. 1, 2005; 77(15):5041-7.

Ahn et al., Fiber-optic microarray for simultaneous detection of multiple harmful algal bloom species. Appl Environ Microbiol. Sep. 2006; 72(9):5742-9.

Albert et al., Automatic decoding of sensor types within randomly ordered, high-density optical sensor arrays. Anal Bioanal Chem. Apr. 2002; 373(8):792-802. Epub Jul. 27, 2002.

Albert et al., Cross-reactive chemical sensor arrays. Chem Rev. Jul. 12, 2000; 100(7):2595-626.

Albert et al., Information coding in artificial olfaction ultisensory arrays. Anal Chem. Aug. 15, 2003; 75(16):4161-7.

Albert et al., Optical multibead arrays for simple and complex odor discrimination. Anal Chem. Jun. 1, 2001; 73(11):2501-8.

Angenendt et al., Subnanoliter enzymatic assays on microarrays. Proteomics. Feb. 2005;5(2):420-5.

Arnaud, Observing single enzymes at work. Chemical & Engineering News. Oct. 2007; 85(44): 8.

Beer et al., On-chip, real-time, single-copy polymerase chain reaction in picoliter droplets. Anal Chem. Nov. 15, 2007;79(22):8471-5. Epub Oct. 11, 2007. Abstract only.

Bencic-Nagale et al., Extending the longevity of fluorescence-based sensor arrays using adaptive exposure. Anal Chem. Oct. 1, 2005; 77(19):6155-62.

Bhat et al., Single molecule detection in nanofluidic digital array enables accurate measurement of DNA copy number Anal Bioanal Chem. May 2009;394(2):457-67. Epub Mar. 15, 2009.

Biran et al., Optical imaging fiber-based live bacterial cell array biosensor. Anal Biochem. Apr. 1, 2003; 315(1):106-13.

Biran et al., Optical imaging fiber-based single live cell arrays: a high-density cell assay platform. Anal Chem. Jul. 1, 2002; 74(13):3046-54.

Blake et al., Phenotypic consequences of promoter-mediated transcriptional noise. Mol Cell. Dec. 28, 2006; 24(6):853-65.

Blicharz et al., Detection of inflammatory cytokines using a fiber optic microsphere immunoassay array. *Proc. SPIE.* 2006; 6380, 638010-1-638010-6.

Blicharz et al., Fiber-optic microsphere-based antibody array for the analysis of inflammatory cytokins in saliva. Anal. Chem. 2009;81(6):2106-14.

Blicharz et al., Use of colorimetric test strips for monitoring the effect of hemodialysis on salivary nitrite and uric acid in patients with end-stage renal disease: a proof of principle. Clin Chem. Sep. 2008; 54(9):1473-80. Epub Aug. 1, 2008.

Bourzac, Next-generation diagnostics: a startup can detect tiny traces of cancer markers in blood samples. Technol Rev. May 13, 2008. Last accessed at http://www.technologyreview.com/Biztech/20760/?a=f on Feb. 2, 2012. 2 pages.

Bowden et al., Development of a microfluidic platform with an optical imaging microarray capable of attomolar target DNA detection. Anal Chem. Sep. 1, 2005; 77(17):5583-8.

Boyden, The chemotactic effect of mixtures of antibody and antigen on polymorphonuclear leucocytes. J Exp Med. Mar. 1, 1962;115:453-66.

Brehm-Stecher et al., Single-cell microbiology: tools, technologies, and applications. Microbiol Mol Biol Rev. Sep. 2004; 68(3):538-59.

Brogan et al., Optical fiber-based sensors: application to chemical biology. Curr Opin Chem Biol. Oct. 2005; 9(5):494-500.

Bronk et al., Combined imaging and chemical sensing using a single optical imaging fiber. Anal Chem. Sep. 1, 1995; 67(17):2750-7.

Bronk et al., Fabrication of patterned sensor arrays with aryl azides on a polymer-coated imaging optical fiber bundle. Anal Chem. Oct. 15, 1994; 66(20):3519-20.

Bulut et al., Tau protein as a serum marker of brain damage in mild traumatic brain injury: preliminary results. Adv Ther. Jan.-Feb. 2006;23(1):12-22.

Burton et al., A microfluidic chip-compatible bioassay based on single-molecule detection with high sensitivity and multiplexing. Lab Chip. Apr. 7, 2010; 10(7):843-51. Epub Jan. 14, 2010.

Cairns, A new market beckons for Alzheimer's blood tests. Evaluate Vantage. Apr. 19, 2021. https://www.evaluate.com/vantage/articles/analysis/spotlight/new-market-beckons-alzheimers-blood-tests [last accessed Jul. 15, 2021]. 3 pages.

Campian, Colored and fluorescent solid supports. Innovation and Perspectives in Solid Phase Synthesis. Ed. R. Epton, Mayflower Worldwide Limited, Birmingham. Ch. 77. 1994:469-472.

Chang et al., Digital ELISA of HIV P24 capsid protein with sensitivity of nucleic acid amplification tests. 2012 AACC Meeting. Los Angeles, CA. Abstract and Poster. 2012. 2 pages.

Chang et al., Prototype digital immunoassay for troponin I with sub-femtomolar sensitivity. 2013 AACC Meeting. Houston, TX. Abstract and Poster. 2013. 2 pages.

Chang et al., Simple diffusion-constrained immunoassay for p24 protein with the sensitivity of nucleic acid amplification for detecting acute HIV infection. J Virol Methods. Mar. 2013;188(1-2):153-60. doi: 10.1016/j.jviromet.2012.08.017. Epub Oct. 2, 2012.

(56)            References Cited

OTHER PUBLICATIONS

Chang et al., Single molecule enzyme-linked immunosorbent assays: theoretical considerations. J Immunol Methods. Apr. 30, 2012;378(1-2):102-15. doi: 10.1016/j.jim.2012.02.011. Epub Apr. 30, 2013. 28 pages.

Chen et al., Microfabricated arrays of cylindrical wells facilitate single-molecule enzymology of alpha-chymotrypsin. Biotechnol Prog. Jul.-Aug. 2009;25(4):929-37.

Chin et al., Editor's Choice: Distinctive individualism. Science. Apr. 4, 2008;320:21.

Chon et al., Characterization of single-cell migration using a computer-aided fluorescence time-lapse videomicroscopy system. Anal Biochem. Oct. 15, 1997;252(2):246-54.

Deutsch et al., Apparatus for high-precision repetitive sequential optical measurement of living cells. Cytometry. Jul. 1, 1994; 16(3):214-26.

Dicesare et al., Individual cell migration analysis using fiber-optic bundles. Anal Bioanal Chem. May 2005; 382(1):37-43. Epub Apr. 1, 2005.

Dickinson et al., A chemical-detecting system based on a cross-reactive optical sensor array. Nature. Aug. 22, 1996; 382(6593):697-700.

Dickinson et al., Convergent, self-encoded bead sensor arrays in the design of an artificial. Anal Chem. Jun. 1, 1999; 71(11):2192-8.

Dickinson et al., Current trends in 'artificial-nose' technology. Trends Biotechnol. Jun. 1998; 16(6):250-8.

Ding et al., Ultrasensitive assays for detection of plasma tau and phosphorylated tau 181 in Alzheimer's disease: a systematic review and meta-analysis. Transl Neurodegener. Mar. 12, 2021;10(1):10.

Dolinak et al., Global hypoxia per se is an unusual cause of axonal injury. Acta Neuropathol. 2000;100:553-60.

Duffy et al., Detection of prostate specific antigen (PSA) in the serum of radical prostatectomy patients at femtogram per milliliter levels using digital ELISA (AccuPSATM) based on single molecule arrays (SiMoA). AACC Meeting Poster. 2010. 1 page.

Duffy, Immunoassays with Broad Dynamic Ranges based on Combining Digital and Digitally Enhanced Analog Detecion of Enzyme Labels. Oak Ridge Conference. Presentation. Apr. 15, 2011. 16 pages.

Duffy, Single Molecule Arrays (Simoa) for Ultrasensitive Protein Detection in Companion Diagnostics. Next Generation DX Summit. Aug. 22, 2012. PowerPoint presentation. 36 slides.

Duffy, Ultra-sensitive protein detection using single molecule arrays (Simoa): the potential for detecting single molecules of botulinum toxin. The Botulinum J. 2012;2(2):164-7.

Egner et al., Tagging in combinatorial chemistry: the use of coloured and flurorescent beads. Chem Commun. 1997; 735-736.

Eid et al., Real-time DNA sequencing from single polymerase molecules. Science. Jan. 2, 2009; 323(5910): 133-8. Epub Nov. 20, 2008.

Ekins et al., Single-molecule ELISA. Clin Chem. Mar. 2011;57(3):372-5. Epub Oct. 13, 2010. Papers in press. Oct. 13, 2010. pp. 1-3.

English et al., Ever-fluctuating single enzyme molecules: Michaelis-Menten equation revisited. Nat Chem Biol. Feb. 2006; 2(2):87-94. Epub Dec. 25, 2005.

Epstein et al., Combinatorial decoding: an approach for universal DNA array fabrication. J Am Chem Soc. Nov. 12, 2003; 125(45):13753-9.

Epstein et al., Fluorescence-based nucleic acid detection and microarrays. Analytica Chimica Acta. 2002; 469:3-36.

Epstein et al., High-density fiber-optic genosensor microsphere array capable of zeptomole detection limits. Anal Chem. Apr. 15, 2002; 74(8):1836-40.

Epstein et al., High-density, microsphere-based fiber optic DNA microarrays. Biosens Bioelectron. May 2003; 18(5-6):541-6.

Epstein, et al., Fluorescence-based fibre optic arrays: a universal platform for sensing. Chem Soc Rev. Jul. 2003; 32(4):203-14.

Ferguson et al., A fiber-optic DNA biosensor microarray for the analysis of gene expression. Nat Biotechnol. Dec. 1996; 14(13):1681-4.

Ferguson et al., High-density fiber-optic DNA random microsphere array. Anal Chem. Nov. 15, 2000; 72(22):5618-24.

Ferguson et al., Simultaneous monitoring of pH, $CO_2$ and $O_2$ using an optical imaging fiber. Analytica Chimica Acta. 1997; 340(1-3):123-131.

Fister et al., Counting single chromophore molecules for ultrasensitive analysis and separations on microchip devices. Analytical Chemistry. 1998; 70:431-437.

Fulton et al., Advanced multiplexed analysis with the FlowMetrix system. Clin Chem. Sep. 1997; 43(9):1749-56.

Furka et al., General method for rapid synthesis of multicomponent peptide mixtures. Int J Pept Protein Res. Jun. 1991;37(6):487-93.

Gebel, Molecule counting made easy. Anal Chem. Sep. 2009; 7130-7131.

Giaever et al., Micromotion of mammalian cells measured electrically. Proc Natl Acad Sci U S A. Sep. 1, 1991;88(17):7896-900.

Goedert et al., Multiple isoforms of human microtubule-associated protein tau: sequences and localization in neurofibrillary tangles of Alzheimer's disease. Neuron. Oct. 1989;3(4):519-26.

Gorris et al., Analytical chemistry on the femtoliter scale. Angew Chem Int Ed. 2010; 49:2-18.

Gorris et al., Mechanistic aspects of horseradish peroxidase elucidated through single-molecule studies. J Am Chem Soc. May 6, 2009; 131(17):6277-82.

Gorris et al., Optical-fiber bundles. FEBS J. Nov. 2007; 274(21):5462-70. Epub Oct. 12, 2007.

Gorris et al., Stochastic inhibitor release and binding from single-enzyme molecules. Proc Natl Acad Sci U S A. Nov. 6, 2007; 104(45):17680-5. Epub Oct. 26, 2007.

Guglielmotto et al., The up-regulation of BACE1 mediated by hypoxia and ischemic injury: role of oxidative stress and HIF1α. J Neurochem. 2009; 108:1045-56.

Harma et al., Europium nanoparticles and time-resolved fluorescence for ultrasensitive detection of prostate-specific antigen. Clin Chem. Mar. 2001; 47(3):561-8.

Härma et al., Miniature single-particle immunoassay for prostate-specific antigen in serum using recombinant Fab fragments. Clin Chem. Nov. 2000; 46(11):1755-61.

Härma et al., Zeptomole detection sensitivity of prostate-specific antigen in a rapid microtitre plate assay using time-resolved fluorescence. Luminescence. Nov.-Dec. 2000;15(6):351-5.

Hashida et al., Immune complex transfer enzyme immunoassay that is more sensitive and specific than western blotting for detection of antibody immunoglobulin G to human immunodeficiency virus type 1 in serum with recombinant pol and gag proteins as antigens. Clin Diagn Lab Immunol. Sep. 1995; 2(5):535-41.

Haugland, Handbook: A Guide to Fluorescent Probes and Labeling Technologies. Invitrogen, Eugene, OR. Molecular Probes, US. 2005. pp. 473-538.

He et al., Selective encapsulation of single cells and subcellular organelles into picoliter- and femtoliter-volume droplets. Anal Chem. Mar. 15, 2005; 77(6):1539-44.

Healey et al., Fiberoptic DNA sensor array capable of detecting point mutations. Anal Biochem. Sep. 5, 1997; 251(2):270-9.

Healey et al., Multianalyte biosensors on optical imaging bundles. Biosens Bioelectron. 1997; 12(6):521-9.

Healey et al., Photodeposition of micrometer-scale polymer patterns on optical imaging fibers. Science. Aug. 25, 1995; 269(5227):1078-80.

Hindson et al., High-throughput droplet digital PCR system for absolute quantitation of DNA copy number Anal Chem. Nov. 15, 2011583(22):8604-10. Epub Oct. 28, 2011.

Hirano et al., A novel method for DNA molecular counting. Nucleic Acids Symp Ser. 2000;(44):157-8.

Hirschfeld, Remote and in-situ analysis. Anal Chem. 1986; 324:618-624.

Hunsaker et al., Nucleic acid hybridization assays employing dA-tailed capture probes. II. Advanced multiple capture methods. Anal Biochem. Sep. 1989; 181(2):360-70.

Jendroska et al., Ischemic stress induces deposition of amyloid β immunoreactivity in human brain. Acta Neuropathol. 1995;90:461-6.

(56) References Cited

OTHER PUBLICATIONS

Jeromin et al., Ultrasensitive detection of neurodegenerative biomarkers in blood with the fully automated Simoa analyzer. AAIC Meeting. Copenhagen, Denmark. Abstract and Poster. 2014. 2 pages.

Jeromin et al., Ultrasensitive detection of total tau in blood in sport-related concussion with the fully automated Simoa analyzer. Traumatic Brain Injury Conference. Washington, DC. Abstract and Poster. 2014. 2 pages.

Johnson et al., Identification of multiple analytes using an optical sensor array and pattern recognition neural networks. Analytical Chemistry. 1997; 69(22):4641-4648.

Joos, Quanterix Web Symposium: Immunoassays in Multiplex for Biomarker Discovery and Validation. Presentation. Feb. 27, 2013. 43 pages.

Kan et al., Isolation and detection of single molecules on paramagnetic beads using sequential fluid flows in microfabricated polymer array assemblies. Lab Chip. Mar. 7, 2012;12(5):977-85. Epub Dec. 16, 2011.

Ke et al., Improving precision of proximity ligation assay by amplified single molecule detection. PLoS One. Jul. 16, 2013;8(7):e69813. doi: 10.1371/journal.pone.0069813. 5 pages.

Kiss et al., High-throughput quantitative polymerase chain reaction in picoliter droplets. Anal Chem. Dec. 1, 2008;80(23):8975-81.

Koike et al., Oligemic hypoperfusion differentially affects tau and amyloid-{beta}. Am J Pathol. 2010;177(1):300-310.

Kremsky et al., Immobilization of DNA via oligonucleotides containing an aldehyde or carboxylic acid group at the 5' terminus. Nucleic Acids Res. Apr. 10, 1987; 15(7):2891-909.

Kuang et al., Living bacterial cell array for genotoxin monitoring. Anal Chem. May 15, 2004; 76(10):2902-9.

Kuang et al., Monitoring "promiscuous" drug effects on single cells of multiple cell types. Anal Biochem. Oct. 15, 2005; 345(2):320-5.

Kuang et al., Simultaneously monitoring gene expression kinetics and genetic noise in single cells by optical well arrays. Anal Chem. Nov. 1, 2004; 76(21):6282-6.

Kunikata et al., Three dimensional microelectrode array device integrating multi-channel microfluidics to realize manipulation and characterization of enzyme-immobilized polystyrene beads. Sens Actuators B Chem. Aug. 18, 2009;141(1):256-62. Abstract only.

Lafratta et al., Very high density sensing arrays. Chem Rev. Feb. 2008; 108(2):614-37. Epub Jan. 30, 2008.

Lee et al., A fiber-optic microarray biosensor using aptamers as receptors. Anal Biochem. Jun. 15, 2000; 282(1):142-6.

Li et al., Detection of single-molecule DNA hybridization using enzymatic amplification in an array of femtoliter-sized reaction vessels. J Am Chem Soc. Sep. 24, 2008; 130(38):12622-3. Epub Sep. 3, 2008.

Li et al., Hypoxia increases $A\beta$ generation by altering $\beta$- and $\gamma$-cleavage of APP. Neurobiol Aging. 2009;30:1091-8.

Li et al., Molecule by molecule direct and quantitative counting of antibody-protein complexes in solution. Anal Chem. Aug. 1, 2004; 76(15):4446-51.

Liliang et al., Tau proteins in serum predict outcome after severe traumatic brain injury. J Surg Res. May 15, 2010;160(2):302-7.

Lu et al., Single-molecule enzymatic dynamics. Science. Dec. 4, 1998; 282(5395):1877-82.

Lui et al., Plasma amyloid-beta as a biomarker in Alzheimer's disease: the AIBL study of aging. J Alzheimers Dis. 2010;20(4):1233-42. doi: 10.3233/JAD-2010-090249.

Luo et al., Single-molecule and ensemble fluorescence assays for a functionally important conformational change in T7 DNA polymerase. Proc Natl Acad Sci U S A. Jul. 31, 2007; 104(31):12610-5. Epub Jul. 18, 2007.

Melin et al., Microfluidic large-scale integration: the evolution of design rules for biological automation. Annu Rev Biophys Biomol Struct. 2007; 36:213-31.

Michael et al., Combined imaging and chemical sensing of fertilization-induced acid release from single sea urchin eggs. Anal Biochem. Sep. 10, 1999; 273(2):168-78.

Michael et al., Randomly ordered addressable high-density optical sensor arrays. Anal Chem. Apr. 1, 1998; 70(7):1242-8.

Mondello et al., CSF and Plasma Amyloid-$\beta$ Temporal Profiles and Relationships With Neurological Status and Mortality After Severe Traumatic Brain Injury: Results of a Pilot Study. 26th Annual Congress of the European Society of Intensive Care Medicine. Abstract. 2013. 2 pages.

Mondello et al., CSF and Plasma Amyloid-$\beta$ Temporal Profiles and Relationships with Neurological Status and Mortality after Severe Traumatic Brain Injury. Scientific Reports. Oct. 10, 2014;4:6446. doi:10.1038/srep06446. 6 pages.

Monk et al., Fabrication of gold microtubes and microwires in high aspect ratio capillary arrays. J Am Chem Soc. Sep. 22, 2004; 126(37):11416-7.

Monk et al., Optical fiber-based biosensors. Anal Bioanal Chem. Aug. 2004; 379(7-8):931-45. Epub Jun. 23, 2004.

Monk et al., Progress toward the dermination of $Sr^{2+}$ in highly basic solutions using imagining optical fiber sensor arrays. J. Mater. Chem. 2005; 15:4361-4366.

Morrison et al., Nanoliter high throughput quantitative PCR. Nucleic Acids Res. 2006;34(18):e123. Epub Sep. 25, 2006.

Mortberg, Assessment of the Cerebral Ischemic/Reperfusion Injury after Cardiac Arrest. Acta Universitatis Upsaliensis Uppsala. Dissertation. 2010. 71 pages.

Munkholm et al., Polymer modification of fiber optic chemical sensors as a method of enhancing fluroescence signal for pH measurement. Anal Chem. 1986; 58:1427-1430.

Nagai et al., High-throughput PCR in silicon based microchamber array. Biosens Bioelectron. Dec. 2001; 16(9-12):1015-9.

Nalefski et al., Single-molecule detection for femtomolar quantification of proteins in heterogeneous immunoassays. Clin Chem. Nov. 2006; 52(11):2172-5.

Nam et al., Nanoparticle-based bio-bar codes for the ultrasensitive detection of proteins. Science. Sep. 26, 2003;301(5641):1884-6.

Neselius et al., Olympic boxing is associated with elevated levels of the neuronal protein tau in plasma. Brain Inj. 2013;27(4):425-33. doi: 10.3109/02699052.2012.750752. Epub Mar. 8, 2013.

Niemeyer et al., Combination of DNA-directed immobilization and immuno-PCR: very sensitive antigen detection by means of self-assembled DNA-protein conjugates. Nucleic Acids Res. Aug. 15, 2003; 31(16):e90.

Okrongly, Single Molecule Enzyme Detection and Application to Immunoassay: Implications for Personalized Medicine. Abstract and Presentation. ISE International Conference. May 4, 2010. 24 pages.

Ost et al., Initial CSF total tau correlates with 1-year outcome in patients with traumatic brain injury. Neurology. Nov. 14, 2006;67(9):1600-4.

Panova et al., In situ fluorescence imaging of localized corrosion with a pH-sensitive imaging fiber. Anal Chem. Apr. 15, 1997; 69(8):1635-41.

Pantano et al., Analytical applications of optical imaging fibers. Anal Chem. Aug. 1, 1995; 67(15):481A-487A.

Pantano et al., Ordered nanowell arrays. Chemistry of Materials. 1996;8: 2832-2835.

Pantano et al., Toward a near-field optical array. Rev. Sci. Instrum. 1997; 68(3) 1357-1359.

Peterson et al., Fiber optic pH probe for physiological use. Anal Chem. May 1980; 52(6):864-9.

Prabhakar et al., Simultaneous quantification of proinflammatory cytokines in human plasma using the LabMAP assay. J Immunol Methods. Feb. 1, 2002;260(1-2):207-18.

Qiu et al., Fluorescence single-molecule counting assays for high-sensitivity detection of cytokines and chemokines. Clin Chem. Nov. 2007; 53(11):2010-2.

Randall et al., Plasma Tau Levels in Concussed Hockey Players. Neuroscience Conference. San Diego, CA. Abstract and Poster. 2013. 2 pages.

Randall et al., Serum Tau is predictive of 6-month cognitive outcome following cardiac arrest. 2011 Neuroscience Conference. Washington, DC. Abstract and Poster. 2011. 2 pages.

Randall et al., Tau proteins in serum predict neurological outcome after hypoxic brain injury from cardiac arrest: Results of a pilot

(56)     References Cited

OTHER PUBLICATIONS study. Resuscitation. Mar. 2013;84(3):351-6. doi: 10.1016/j. resuscitation.2012.07.027. Epub Aug. 9, 2012. Epub Aug. 9, 2012. 6 pages.

Randle et al., Integrating molecular detection and response to create self-signalling antibodies. Biochem Biophys Res Commun. Nov. 12, 2004; 324(2):504-10.

Rissin et al., Attomolar detection of proteins in serum using single molecule enzyme-linked immunosorbent assays. Quanterix Corporation. Oak Ridge Conference, San Jose, CA. Poster. 2010. 1 page.

Rissin et al., Digital concentration readout of single enzyme molecules using femtoliter arrays and Poisson statistics. Nano Lett. Mar. 2006; 6(3):520-3.

Rissin et al., Digital readout of target binding with attomole detection limits via enzyme amplification in femtoliter arrays. J Am Chem Soc. May 17, 2006; 128(19):6286-7.

Rissin et al., Distinct and long-lived activity states of single enzyme molecules. J Am Chem Soc. Apr. 16, 2008; 130(15):5349-53. Epub Mar. 5, 2008.

Rissin et al., Duplexed sandwich immunoassays on a fiber-optic microarray. Anal Chim Acta. Mar. 30, 2006; 564(1):34-9. Epub Nov. 11, 2005.

Rissin et al., Immunoassays with broad dynamic ranges based on combining digital and digitally-enhanced analog detection of enzyme labels. Oak Ridge Conference. Poster 7 and Abstract. Apr. 14-15, 2011. 2 pages.

Rissin et al., Multiplexed single molecule immunoassays. Lab Chip. Aug. 7, 2013;13(15):2902-11. doi: 10.1039/c3lc50416f.

Rissin et al., Simultaneous detection of single molecules and singulated ensembles of molecules enables immunoassays with broad dynamic range. Anal Chem. Mar. 15, 2011;83(6):2279-85. Epub Feb. 23, 2011.

Rissin et al., Single-molecule enzyme-linked immunosorbent assay detects serum proteins at subfemtomolar concentrations. Nat Biotechnol. Jun. 2010; 28(6):595-9 and supplemental pages. Epub May 23, 2010.

Roeffaers et al., Single-molecule fluorescence spectroscopy in (bio)catalysis. Proc Natl Acad Sci U S A. Jul. 31, 2007; 104(31):12603-9. Epub Jul. 30, 2007.

Rondelez et al., Highly coupled ATP synthesis by F1-ATPase single molecules. Nature. Feb. 17, 2005; 433(7027):773-7.

Rondelez et al., Microfabricated arrays of femtoliter chambers allow single molecule enzymology. Nat Biotechnol. Mar. 2005; 23(3):361-5. Epub Feb. 20, 2005.

Rotman, Measurement of activity of single molecules of beta-D-galactosidase. Proc Natl Acad Sci U S A. Dec. 15, 1961; 47:1981-91.

Schauer et al., A cross-reactive, class-selective enzymatic array assay. J Am Chem Soc. Sep. 26, 2001; 123(38):9443-4.

Schmidinger, et al., Inhibitor and protein microarrays for activity-based recognition of lipolytic enzymes. Chembiochem. Mar. 2006; 7(3):527-34.

Schweitzer et al., Inaugural article: immunoassays with rolling circle DNA amplification: a versatile platform for ultrasensitive antigen detection. Proc Natl Acad Sci U S A. Aug. 29, 2000; 97(18):10113-9.

Seydack, Nanoparticle labels in immunosensing using optical detection methods. Biosens Bioelectron. Jun. 15, 2005; 20(12):2454-69. Epub Dec. 16, 2004.

Shahim et al., Blood biomarkers for brain injury in concussed professional ice hockey players. JAMA Neurol. Jun. 2014;71(6):684-92. doi: 10.1001/jamaneurol.2014.367. Epub Mar. 13, 2014. 9 pages.

Shen et al. High-throughput SNP genotyping on universal bead arrays. Mutat Res. Jun. 3, 2005;573(1-2):70-82.

Shephard et al., Array-based binary analysis for bacterial typing. Anal Chem. Jan. 1, 2005; 77(1):319-26.

Shiiya et al., Tau protein in the cerebrospinal fluid is a marker of brain injury after aortic surgery. Ann Thorac Surg. Jun. 2004;77(6):2034-8.

Song et al., Detecting biological warfare agents. Emerg Infect Dis. Oct. 2005; 11(10):1629-32.

Song et al., Direct Detection of Bacterial DNA and viral RNA at Subfemtomolar Concentrations Using Single Molecule Arrays (Simoa). 2013 Oakridge Conference. Baltimore, MD. Abstract and Poster. 2013. 2 pages.

Song et al., Direct detection of bacterial genomic DNA at sub-femtomolar concentrations using single molecule arrays. Anal Chem. Feb. 5, 2013;85(3):1932-9. doi: 10.1021/ac303426b. Epub Jan. 18, 2013. Supporting information included.

Song et al., Fiber-optic microsphere-based arrays for multiplexed biological warfare agent detection. Anal Chem. Feb. 15, 2006; 78(4):1023-33.

Song et al., Single molecule measurements of tumor necrosis factor α andinterleukin-6 in the plasma of patients with Crohn's disease. J Immunol Methods Sep. 30, 2011;372(1-2):177-86. Epub Jul. 27, 2011.

Soukka et al., Supersensitive time-resolved immunofluorometric assay of free prostate-specific antigen with nanoparticle label technology. Clin Chem. 2001; 47(7):1269-78.

Stamou et al., Self-assembled microarrays of attoliter molecular vessels. Angew Chem Int Ed Engl. Nov. 24, 2003; 42(45):5580-3.

Steemers et al., Multi-analyte sensing: from site-selective deposition to randomly ordered addressable optical sensors. Microchimica Acta. 1999; 131:99-105.

Steemers et al., Screening unlabeled DNA targets with randomly ordered fiber-optic gene arrays. Nat Biotechnol. Jan. 2000; 18(1):91-4.

Stitzel et al., Array-to-array transfer of an artificial nose classifier. Anal Chem. Nov. 1, 2001; 73(21):5266-71.

Subbaraman, Detecting single cancer molecules. Technol Rev. Jun. 3, 2010. Last accessed at http://www.technologyreview.com/biomedicine/25462/ on Jan. 31, 2012. 2 pages.

Suh et al., Hypoxic ischemia and proteasome dysfunction alter tau isoform ratio by inhibiting exon 10 splicing. J Neurochem. Jul. 2010;114(1):160-70. doi: 10.1111/j.1471-4159.2010.06732.x. Epub Apr. 3, 2010.

Sun et al., Hypoxia facilitates Alzheimer's disease pathogenesis by up-regulating BACE1 gene expression. PNAS. Dec. 5, 2006;103(49):18727-32.

Sykes et al., Quantitation of targets for PCR by use of limiting dilution. Biotechniques. 1992;13(3):444-9.

Szunerits et al., "Aluminum Surface Corrosion and the Mechanism of Inhibitors Using pH and Metal Ion Selective Imaging Fiber Bundles," Analytical Chemistry, 2002, 74(4), 886-894.

Szunerits et al., "Fabrication of an Optoelectrochemical Microring Array," Analytical Chemistry, 2002, 74(7), 1718-1723.

Szunerits et al., Spatially resolved electrochemiluminescence on an array of electrode tips. Anal Chem. Sep. 1, 2003; 75(17):4382-8.

Szunerits et al., The use of optical fiber bundles combined with electrochemistry for chemical imaging. Chemphyschem. Feb. 17, 2003; 4(2):186-92.

Szurdoki et al., A duplexed microsphere-based fluorescent immunoassay. Anal Biochem. Apr. 15, 2001; 291(2):219-28.

Tam et al., An imaging fiber-based optical tweezer array for microparticle array assembly. Applied Physics Letters. 2004; 84(21):4289-4291.

Tam et al., Fabrication and optical characterization of imaging fiber-based nanoarrays. Talanta. Sep. 15, 2005; 67(3):498-502. Epub Jul. 27, 2005.

Tam et al., Parallel microparticle manipulation using an imaging fiber bundle-based optical tweezer array and a digital micromirror device. Applied Physics Letters. 2006; 89:194101/1-194101/3.

Tan et al., Monitoring the reactions of single enzyme molecules and single metal ions. Anal. Chem. 1997; 69:4242-4248.

Tanen et al., Development of an Ultrasensitive Digital Immunoassay on the Single Molecule Array (SimoaTM) Platform. 2014 AAPS Annual Meeting. San Diego, CA. Abstract and Poster. Nov. 2-6, 2014. 2 pages.

Taylor et al., Application of high-density optical microwell arrays in a live-cell biosensing system. Anal Biochem. Feb. 15, 2000; 278(2):132-42.

(56) References Cited

OTHER PUBLICATIONS

Taylor et al., Hypoxic Enhancement of Quantal Catecholamine Secretion: Evidence for the Involvement of Amyloid β-Peptides. J Biol Chem. Oct. 29, 1999;274(44):31217-22.

Tessler et al., Protein quantification in complex mixtures by solid phase single-molecule counting. Anal Chem. Sep. 1, 2009; 81(17):7141-8.

Tettenborn et al., Prophylaxis and acute therapy of arterial embolism with special reference to cerebral embolism. Herz. Dec. 1991;16(6):444-55. Review. Abstract only. 1 page.

Teunissen et al., Plasma p-tau217: from 'new kid' to most promising candidate for Alzheimer's disease blood test. Brain. Dec. 5, 2020;143(11):3170-3172.

Timmerman, Quanterix CEO sets sight on early detection of cancer, neurological diseases in the blood. Xconomy. Jan. 19, 2010. Last accessed at http://www.xconomy.com/boston/2010/01/19/quanterix-ceo-sets-sight-on-early-detection-of-cancer-neurological-diseases-in-the-blood/ on Jan. 31, 2012. 4 pages.

Todd et al., Ultrasensitive flow-based immunoassays using single-molecule counting. Clin Chem. Nov. 2007; 53(11):1990-5. Epub Sep. 21, 2007.

Tromberg et al., Development of antibody-based fiber-optic sensors for detection of a benzo[a]pyrene metabolite. Anal Chem. Sep. 15, 1988; 60(18):1901-8.

Ueberfeld et al., Reversible ratiometric probe for quantitative DNA measurements. Anal Chem. Feb. 15, 2004; 76(4):947-52.

Vo-Dinh et al., Phase-resolved fiber-optics fluoroimmunosensor. Applied Spectroscopy. 1990; 44(1):128-132.

Vogelstein et al., Digital PCR. Proc Natl Acad Sci U S A. Aug. 3, 1999;96(16):9236-41.

Walt et al., Biosensing with live cells using a high-density optical fiber array. Radiation Research. 2001; 156(4):442.

Walt et al., Microsensor arrays for saliva diagnostics. Ann N Y Acad Sci. Mar. 2007;1098:389-400.

Walt et al., Optical sensor arrays for odor recognition. Biosens Bioelectron. Sep. 15, 1998; 13(6):697-9.

Walt et al., Ultrasensitive detection of proteins using single mol-ecule arrays (SiMoA). Presented Mar. 1, 2010. Pittcon. Abstract and PowerPoint presentation. 33 pages.

Walt, An array of solutions, fiber arrays contribute to studies of individual cellular behavior and response. SPIE'S oemagazine. 2005; 19-21.

Walt, Fiber optic array biosensors. Biotechniques. Nov. 2006; 41(5):529, 531, 533 passim.

Walt, Fiber optic imaging sensors. Accounts of Chemical Research. 1998; 31:267-278.

Walt, Imaging optical sensor arrays. Curr Opin Chem Biol. Oct. 2002; 6(5):689-95.

Walt, Optical methods for single molecule detection and analysis. Anal Chem. Feb. 5, 2013;85(3):1258-63. doi: 10.1021/ac3027178. Epub Dec. 19, 2012.

Walt, Techview: molecular biology. Bead-based fiber-optic arrays. Science. Jan. 21, 2000; 287(5452):451-2.

Wang et al., Cerebrovascular hypoperfusion induces spatial memory impairment, synaptic changes, and amyloid-β oligomerization in rats. J Alzheimers Dis. 2010;21(3):813-822.

Wang et al., Quantification of protein based on single-molecule counting by total internal reflection fluorescence microscopy with adsorption equilibrium. Anal Chim Acta. May 2, 2007; 590(1):104-9. Epub Mar. 15, 2007.

Warren et al., Transcription factor profiling in individual hematopoietic progenitors by digital RT-PCR. Proc Natl Acad Sci U S A. Nov. 21, 2006;103(47):17807-12. Epub Nov. 10, 2006.

Whitaker et al., Fiber-based single cell analysis of reporter gene expression in yeast two-hybrid systems. Anal Biochem. Jan. 1, 2007; 360(1):63-74. Epub Oct. 30, 2006.

Whitaker et al., Multianalyte single-cell analysis with multiple cell lines using a fiber-optic array. Anal Chem. Dec. 1, 2007; 79(23):9045-53. Epub Nov. 1, 2007.

White et al., An olfactory neuronal network for vapor recognition in an artificial nose. Biol Cybern. Apr. 1998; 78(4):245-51.

White et al., Rapid analyte recognition in a device based on optical sensors and the olfactory system. Analytical Chemistry. 1996; 68(13):2191-2202.

Wilson et al., Development of AccuPSA™, a novel digital immunoassay for sub-femtomolar measurement of PSA in post radical prostatectomy patients. AACR Molecular diagnostics in Cancer Therapeutic Development Poster. 2011. 1 page.

Wilson et al., Fifth-generation digital immunoassay for prostate-specific antigen by single molecule array technology. Clin Chem. Dec. 2011;57(12):1712-21. Epub Oct. 13, 2011.

Wilson et al., Simoa™ HD-1: a fully automated digital immunoassay analyzer capable of single molecule counting, sub-femtomolar sensitivity, and multiplexing. 2014 AACC Meeting. Chicago, IL. Abstract and Poster. 2014. 2 pages.

Wilson, Serum Measurement of Hypoxia-Induced Amyloid Beta 1-42 Following Resuscitation from Cardiac Arrest. Abstract and Poster. American Academy of Neurology Annual Meeting. Apr. 9, 2011. 2 pages.

Wu et al., Development and preliminary clinical validation of a high sensitivity assay for cardiac troponin using a capillary flow (single molecule) fluorescence detector. Clin Chem. Nov. 2006; 52(11):2157-9.

Wunderlich et al., Neuron-specific enolase and tau protein as neurobiochemical markers of neuronal damsage are related to early clinical course and long-term outcome in acute ischemic stroke. Clinical Neurology and Neurosurgery. Sep. 2006;108:558-63.

Xie et al., Optical studies of single molecules at room temperature. Annu Rev Phys Chem. 1998; 49:441-80.

Xie et al., Single gold nanoparticles counter: an ultrasensitive detection platform for one-step homogeneous immunoassays and DNA hybridization assays. J Am Chem Soc. Sep. 9, 2009;131(35):12763-70.

Xue et al., Differences in the chemical reactivity of individual molecules of an enzyme. Nature. Feb. 23, 1995; 373(6516):681-3.

Yan et al., Analyzing polyubiquitin chains upon ubiquitin activating enzyme inhibition from cell culture & tumor lysates using the Quanterix's single molecule array (Simoa) technology. 2013 Society for the Laboratory Automation & Screening Annual Meeting. Orlando, FL. Abstract and Poster. 2013. 2 pages.

Young et al., Integrating high-content screening and ligand-target prediction to identify mechanism of action. Nat Chem Biol. Jan. 2008; 4(1):59-68. Epub Dec. 9, 2007.

Zetterberg et al., Hypoxia due to cardiac arrest induces a time-dependent increase in serum amyloid β levels in humans. PLoS One. 2011;6(12):e28263. doi: 10.1371/journal.pone.0028263. Epub Dec. 14, 2011.

Zetterberg et al., Hypoxia due to cardiac arrest induces a time-dependent increase in serum amyloid β levels in humans. PLoS One. 2011;6(12):e28263. Epub Dec. 14, 2011.

Zetterberg et al., Plasma tau levels in Alzheimer's disease. Alzheimers Res Ther. Mar. 28, 2013;5(2):9. doi: 10.1186/alzrt163. eCollection 2013.

Zetterberg, Quanterix Web Symposium: Peripheral Blood Biomarkers for Brain Damage—Challenging but Feasible. Presentation. Oct. 16, 2012. 29 pages.

Zhang et al., Hypoxia-inducible Factor 1α (HIF-1α)-mediated Hypoxia Increases BACE1 Expression and β-Amyloid Generation. J Biol Chem. Apr. 13, 2007;282(15):10873-80.

Office Action for U.S. Appl. No. 14/111,326 dated Jan. 29, 2015.

Office Action for U.S. Appl. No. 15/269,142 dated Dec. 31, 2018.

Office Action for U.S. Appl. No. 16/522,237 dated Mar. 16, 2021.

Response to Non-Final Office Action for U.S. Appl. No. 16/522,237 dated Jul. 16, 2021.

Office Action for U.S. Appl. No. 17/589,912 dated Mar. 19, 2025.

Office Action for U.S. Appl. No. 19/073,950 dated Apr. 7, 2025.

Office Action for U.S. Appl. No. 19/073,950 dated Jul. 30, 2025.

[No Author Listed], Alzheimer's Disease (AD). Applications. Quanterix. 2010. https://web.archive.org/web/20100529185326/http://www.quanterix.com/applications/ad.html [last accessed Jun. 6, 2025]: 2 pages.

(56)                    References Cited

OTHER PUBLICATIONS

[No Author Listed], Answer to 1 Complaint with Jury Demand, Amended Counterclaim against Fujirebio Diagnostics, Inc., Fujirebio Europe N.V. by Quanterix Corporation. United States District Court for the District of Delaware. Jul. 14, 2025: 458 pages.
[No Author Listed], Assay Kits. Simoa. Quanterix. 2013. https://web.archive.org/web/20131022204103/http://quanterix.com/products/assay-kits [last accessed Jun. 6, 2025]: 2 pages.
[No Author Listed], Aβ-42 (Amyloid beta protein 42). Singulex Life Science Products. 2006: 1 page.
[No Author Listed], Complaint for Declaratory Judgement for *Fujirebio Diagnostics, Inc.* v. *Quanterix Corporation* filed May 28, 2025: 49 pages.
[No Author Listed], Curriculum vitae of Petitioner's Expert John Todd, PhD. 11 pages.
[No Author Listed], Declaration of Ingrid Hsieh-Yee, PhD. *Fujirebio Diagnsotics, Inc.,* v. *Quanterix Corp.* USPTO Before the Patent Trial and Appeal Board. May 28, 2015: 91 pages.
[No Author Listed], Declaration of John Todd PhD in support of Petition for Inter Partes Review of U.S. Pat. No. 11,275,092. *Fujirebio Diagnsotics, Inc.,* v. *Quanterix Corp.* USPTO Before the Patent Trial and Appeal Board. May 28, 2025: 94 pages.
[No Author Listed], Defendant and counter-plaintiff Quanterix Corporation's opposition brief to Fujirebio Diagnostics, Inc.'s motion to dismiss amended counterclaim pursuant to Fed R. Civ. P. 12 (B)(6). United States District Court. Oct. 24, 2025: 26 pages.
[No Author Listed], Defendant Quanterix Corporation's Answer to Complaint and Second Amended Counterclaim. USDC. Oct. 24, 2025: 66 pages.
[No Author Listed], Demand for Jury Trial. Defendant Quanterix Corporation's Answer to Complaint and Counterclaims. United States District Court for the District of Delaware. Jun. 23, 2025; 112 pages.
[No Author Listed], Innotest hTAU Ag. Innogenetics. https://web.archive.org/web/20040914040003fw_/http://www.innogenetics.be/site/prodview.asp?id=38&lang=E&print=true [last accessed Jun. 6, 2025]: 4 pages.
[No Author Listed], Patent owner preliminary response. USPTO Before the Patent Trial and Appeal Board. Sep. 22, 2025: 43 pages.
[No Author Listed], Patent Owner's Brief in Support of Discretionary Denial. USPTO Before the Patent Trial and Appeal Board. Aug. 20, 2025: 39 pages.
[No Author Listed], Petition for Inter Partes Review of U.S. Pat. No. 11,275,092. United States Patent and Trademark Office Before the Patent Trial and Appeal Board. May 28, 2025: 86 pages.
[No Author Listed], Petitioner's opposition to patent owner's request for discretionary denial of institution. USPTO Before the Patent Trial and Appeal Board. Sep. 19, 2025: 58 pages.
[No Author Listed], Plaintiff and counter-defendant Fujirebio Diagnostics, Inc.'s opening brief in support of its motion to dismiss Quanterix Corporation's amended counterclaim. United States District Court for the District of Delaware. Sep. 5, 2025: 26 pages.
[No Author Listed], Prosecution history of U.S. Appl. No. 08/159,969 (granted as U.S. Pat. No. 5,492,812) as of Feb. 20, 1996: 177 pages.
[No Author Listed], Prosecution history of U.S. Appl. No. 14/111,326 as of Apr. 26, 2017: 816 pages.
[No Author Listed], Prosecution history of U.S. Appl. No. 15/269,142 (granted as U.S. Pat. No. 10,393,759) as of Oct. 1, 2019: 379 pages.
[No Author Listed], Prosecution history of U.S. Appl. No. 16/522,237 (granted as U.S. Pat. No. 11,275,092) as of Mar. 25, 2025: 391 pages.
[No Author Listed], Quanterix Announces Key Patents Issued for Simoa Platform. Quanterix. Oct. 16, 2013: 1 page.
[No Author Listed], Quanterix Issued Key Patent for Simoa Technology. Press Release. Questex. Aug. 7, 2012: 1 page.
Banks et al., Release of the angiogenic cytokine vascular endothelial growth factor (VEGF) from platelets: significance for VEGF measurements and cancer biology. Br J Cancer. Mar. 1998;77(6):956-64. doi: 10.1038/bjc.1998.158.

Bitsch et al., Serum tau protein level as a marker of axonal damage in acute ischemic stroke. Eur Neurol. 2002;47(1):45-51. doi: 10.1159/000047946.
Blennow et al., CSF markers for incipient Alzheimer's disease. Lancet Neurol. Oct. 2003;2(10):605-13. doi: 10.1016/s1474-4422(03)00530-1.
Bogoslovsky et al., Increases of Plasma Levels of Glial Fibrillary Acidic Protein, Tau, and Amyloid β up to 90 Days after Traumatic Brain Injury. J Neurotrauma. Jan. 1, 2017;34(1):66-73. doi: 10.1089/neu.2015.4333.
De Jong et al., Current state and future directions of neurochemical biomarkers for Alzheimer's disease. Clin Chem Lab Med. 2007;45(11):1421-34. doi: 10.1515/CCLM.2007.320.
Galasko, Biomarkers for Alzheimer's disease—clinical needs and application. J Alzheimers Dis. Mar. 2005;8(4):339-46. doi: 10.3233/jad-2005-8403.
Gavett et al., Mild traumatic brain injury: a risk factor for neurodegeneration. Alzheimers Res Ther. Jun. 25, 2010;2(3):18. doi: 10.1186/alzrt42.
Hampel et al., Total and Phosphorylated Tau Protein as Biological Markers of Alzheimer's Disease. Exp Gerontol. Jan. 2010;45(1):30. doi: 10.1016/j.exger.2009.10.010.
Humpel, Identifying and validating biomarkers for Alzheimer's disease. Trends Biotechnol. Jan. 2011;29(1):26-32. doi: 10.1016/j.tibtech.2010.09.007. Epub Oct. 23, 2010.
Konzack et al., Swimming against the Tide: Mobility of the Microtubule-Associated Protein Tau in Neurons. J Neuroscience. Sep. 2007;27(37):9916-27. doi: 10.1523/JNEUROSCI.0927-07.2007.
Koul et al., Temporal relationship between neurofilament light chain and cytokines involved in T helper-17 lymphocyte signaling in the blood of experimental autoimmune encephalomyelitis mice. Mult Scler Relat Disord. Jul. 2025;99:106463. doi: 10.1016/j.msard.2025.106463. Epub Apr. 21, 2025.
Medeiros et al., The role of tau in Alzheimer's disease and related disorders. CNS Neurosci Ther. Oct. 2011; 17(5):514-24. doi: 10.1111/j.1755-5949.2010.00177.x. Epub Jun. 14, 2010.
Mortimer et al., Head trauma as a risk factor for Alzheimer's disease: a collaborative re-analysis of case-control studies. EURODEM Risk Factors Research Group. Int J Epidemiol. 1991;20 Suppl 2:S28-35. doi: 10.1093/ije/20.supplement_2.s28.
O'Brien et al., Elevated Serum Interleukin-1β Levels in Male, but not Female, Collision Sport Athletes with a Concussion History. J Neurotrauma. May 15, 2021;38(10):1350-1357. doi: 10.1089/neu.2020.7479. Epub Feb. 24, 2021.
Ruder et al., Dynamics of Inflammatory and Neurodegenerative Biomarkers after Autologous Hematopoietic Stem Cell Transplantation in Multiple Sclerosis. Int J Mol Sci. Sep. 19, 2022;23(18):10946. doi: 10.3390/ijms231810946.
Schraen-Maschke et al., Tau as a biomarker of neurodegenerative diseases. Biomark Med. Aug. 2008;2(4):363-84. doi: 10.2217/17520363.2.4.363.
Tang et al., Human pro-tumor necrosis factor is a homotrimer. Biochemistry. Jun. 25, 1996;35(25):8216-25. doi: 10.1021/bi952182t.
Thaxton et al., Nanoparticle-based bio-barcode assay redefines "undetectable" PSA and biochemical recurrence after radical prostatectomy. Proc Natl Acad Sci U S A. Nov. 3, 2009;106(44):18437-42. Epub Oct. 19, 2009. 6 pages.
Todd et al., How low can you go? Next generation immunoassay systems and the revival of protein biomarkers. Immunoassays. Drug Discovery World. Oct. 2008:51-57.
Vandermeeren et al., Detection of tau proteins in normal and Alzheimer's disease cerebrospinal fluid with a sensitive sandwich enzyme-linked immunosorbent assay. J Neurochem. Nov. 1993;61(5):1828-34. doi: 10.1111/j.1471-4159.1993.tb09823.x.
Weingarten et al., A protein factor essential for microtubule assembly. Proc Natl Acad Sci USA. May 1975;72(5):1858-62. doi: 10.1073/pnas.72.5.1858.
Office Action for U.S. Appl. No. 17/589,912 dated Nov. 14, 2025.
[No Author Listed], Plaintiff and Counter-Defendant Fujirebio Diagnostics, Inc.'s Reply Brief in Support of Its Motion to Dismiss Quanterix Corporation's Amended Counterclaim Pursuant to Fed.

(56) References Cited

OTHER PUBLICATIONS

R. Civ. P. 12(b)(6). United States District Court for the District of Delaware. Nov. 19, 2025: 14 pages.

Brodacki et al., Serum interleukin (IL-2, IL-10, IL-6, IL-4), TNFalpha, and INFgamma concentrations are elevated in patients with atypical and idiopathic parkinsonism. Neurosci Lett. Aug. 22, 2008441(2):158-62. doi: 10.1016/j.neulet.2008.06.040. Epub Jun. 19, 2008.

Fein et al., Co-localization of amyloid beta and tau pathology in Alzheimer's disease synaptosomes. Am J Pathol. Jun. 2008;172(6):1683-92. doi: 10.2353/ajpath.2008.070829. Epub May 8, 2008.

Knoblach et al., Early neuronal expression of tumor necrosis factor-alpha after experimental brain injury contributes to neuro-logical impairment. J Neuroimmunol. Mar. 1, 1999;95(1-2):115-25. doi: 10.1016/s0165-5728(98)00273-2.

Orozco et al., Flow cytometric analysis of circulating microparticles in plasma. Cytometry A. Jun. 2010;77(6):502-14. doi: 10.1002/cyto.a.20886.

* cited by examiner

METHODS OF PRODUCING BODILY FLUID SAMPLES CONTAINING AN ANALYTICALLY QUANTIFIED AMOUNT OF PHOSPHORYLATED TAU PROTEIN

RELATED APPLICATIONS

This application is a continuation of U.S. patent application Ser. No. 16/522,237, filed Jul. 25, 2019, and entitled "METHODS OF DETERMINING A TREATMENT PROTOCOL FOR AND/OR A PROGNOSIS OF A PATIENT'S RECOVERY FROM A BRAIN INJURY," which is a continuation of U.S. patent application Ser. No. 15/269,142, filed Sep. 19, 2016, and entitled "METHODS OF DETERMINING A TREATMENT PROTOCOL FOR AND/OR A PROGNOSIS OF A PATIENT'S RECOVERY FROM A BRAIN INJURY," which is a continuation of U.S. patent application Ser. No. 14/111,326, filed Jun. 24, 2014, and entitled "METHODS OF DETERMINING A TREATMENT PROTOCOL FOR AND/OR A PROGNOSIS OF A PATIENT'S RECOVERY FROM A BRAIN INJURY," which is a national stage of International Patent Application Serial No. PCT/US2012/033343, filed Apr. 12, 2012, and entitled "METHODS OF DETERMINING A TREATMENT PROTOCOL FOR AND/OR A PROGNOSIS OF A PATIENT'S RECOVERY FROM A BRAIN INJURY," which claims priority under 35 U.S.C. § 119 (e) to U.S. Provisional Patent Application Ser. No. 61/474,315, filed Apr. 12, 2011, and entitled "METHODS OF DETERMINING A TREATMENT PROTOCOL FOR AND/OR A PROGNOSIS OF A PATIENT'S RECOVERY FROM A BRAIN INJURY RESULTING FROM A HYPOXIC EVENT." and claims priority under 35 U.S.C. § 119 (e) to U.S. Provisional Patent Application Ser. No. 61/524,693, filed Aug. 17, 2011, and entitled "METHODS OF DETERMINING A TREATMENT PROTOCOL FOR AND/OR A PROGNOSIS OF A PATIENT'S RECOVERY FROM A BRAIN INJURY." each of which are incorporated herein by reference in their entireties for all purposes.

FIELD OF THE INVENTION

The present invention generally relates, in some embodiments, to methods of determining a treatment protocol for and/or a prognosis of a patient's recovery from a brain injury. In some embodiments, the brain injury results from a hypoxic event. In some embodiments, methods are provided for determining a measure of the concentration of tau protein in a patient sample containing or suspected of containing tau protein.

BACKGROUND OF THE INVENTION

A brain injury in a human may be caused by any number of events or conditions. In some cases, a brain injury may be caused by external mechanical force, such as rapid acceleration or deceleration, impact, blast waves, or penetration by a projectile. This type of acquired brain injury is generally known as traumatic brain injury. Another type of acquired brain injury involves biochemical forces, such as oxygen deprivation (hypoxia). Hypoxia generally refers to a deficiency in the amount of oxygen reaching body tissues or a condition of insufficient levels of oxygen in tissue or blood. Oxygen deprivation to the brain results in neuronal damage and death, which is in turn related to the extent of long term brain dysfunction. The concentration of certain biomarkers may become elevated as a result of neuronal damage and death. For example, tau proteins are associated with microtubules and localized in the axonal compartment of neurons. Tau is known to be elevated in the cerebrospinal fluid (CSF) of patients with neurodegenerative disease and head injuries. However, since such biomarkers must diffuse across the blood brain barrier, they may be present in the blood in proportion in extremely low concentrations that are not reliably measurable by typical conventional immunoassays. While the concentration of some biomarkers in the brain and central nervous system are known to increase with hypoxic events, the increased concentration has not been correlated with specific diagnostic indications and/or methods of treatment. In addition, while some methods exist for determining a brain injury in a patient and/or determining a course of treatment following a brain injury, many of the known methods are costly (e.g., magnetic resonance imaging) and/or provide unclear results and/or predictors. Accordingly, improved methods are needed.

SUMMARY OF THE INVENTION

In some embodiments, a method for determining a measure of the concentration of tau protein in a patient sample containing or suspected of containing tau protein is provided comprising performing an assay to determine a measure of the concentration of tau protein in the sample, wherein the limit of detection of tau protein of the assay is less than about 0.2 pg/mL.

In some embodiments, a method of determining a treatment protocol for and/or a prognosis of a patient's recovery from a brain injury is provided comprising performing an assay on a blood sample from the patient and/or plasma and/or serum derived from the blood sample to determine a measure of the concentration of tau protein in the sample; and determining a prognosis of the patient's recovery from the brain injury and/or a method of treatment based at least in part on the measured concentration of tau protein present in the sample.

In some embodiments, a method of determining a treatment protocol for and/or a prognosis of a patient's recovery from a brain injury is provided comprising determining a prognosis of the patient's recovery from the brain injury and/or a method of treatment based at least in part on a measured concentration of tau protein present in a patient sample, wherein the measured concentration has been determined by performing an assay on the patient sample, which comprises a blood sample from the patient and/or plasma and/or serum derived from the blood sample, to determine the measure of the concentration of tau protein in the sample.

In some embodiments, a method for performing an assay and providing data for determining a treatment protocol for and/or a prognosis of a patient's recovery from a brain injury is provided comprising performing an assay on a blood sample from the patient and/or plasma and/or serum derived from the blood sample to determine a measure of the concentration of tau protein in the sample; and providing data from the assay to enable determining a prognosis of the patient's recovery from the brain injury and/or a method of treatment based at least in part on the measured concentration of tau protein present in the sample.

In some embodiments, a method of determining a treatment protocol for and/or a prognosis of a patient's recovery from a brain injury is provided comprising determining a measure of the concentration of tau protein in each of a plurality of samples obtained from the patient following the brain injury; and determining a prognostic of the patient's recovery from the brain injury and/or a method of treatment based at least in part on the measured concentration tau protein present in the sample.

In some embodiments, a method of determining a method of treatment for and/or a prognosis of a patient's recovery from a brain injury is provided comprising (a) performing an assay on each of a plurality of samples obtained from the patient following the brain injury to determine the measured concentration of tau protein in each of the samples, wherein the plurality of samples are obtained from the patient over a period of time of at least about 48 hours; (b) determining the area under the curve of a graph of the tau protein concentration in the plurality of samples versus time, wherein the area is determined for the entire time period and/or for a second peak in the tau protein concentration; and (c) determining a prognosis of the patient's recovery from the brain injury and/or a method of treatment based at least in part on the area under the curve for the entire time period and/or the second peak in the tau protein concentration determined in step (b).

In some embodiments, a method of determining a method of treatment for and/or a prognosis of a patient's recovery from a brain injury is provided comprising determining a prognosis of the patient's recovery from the brain injury and/or a method of treatment based at least in part on the area under the curve of a graph of the tau protein concentration in the plurality of samples versus time, wherein the area is determined for the entire time period and/or for a second peak in the tau protein concentration, which has been determined by (a) performing an assay on each of a plurality of samples obtained from the patient following the brain injury to determine the measured concentration of tau protein in each of the samples, wherein the plurality of samples have been obtained from the patient over a period of time of at least about 48 hours; and (b) determining the area under the curve of a graph of the tau protein concentration in the plurality of samples versus time for the entire time period and/or for a second peak in the tau protein.

In some embodiments, a method for performing an assay and providing data for determining a method of treatment for and/or a prognosis of a patient's recovery from a brain injury is provided comprising (a) performing an assay on each of a plurality of samples obtained from the patient following the brain injury to determine the measured concentration of tau protein in each of the samples, wherein the plurality of samples are obtained from the patient over a period of time of at least about 48 hours; (b) determining the area under the curve of a graph of the tau protein concentration in the plurality of samples versus time, wherein the area under the curve is determined for the entire time period and/or for a second peak in the tau protein concentration; and (c) providing data derived in steps (a) and (b) to enable determining a prognosis of the patient's recovery from the brain injury and/or a method of treatment based at least in part on the area under the curve determined for the entire time period and/or for a second peak in the tau protein concentration.

Figure 1A:
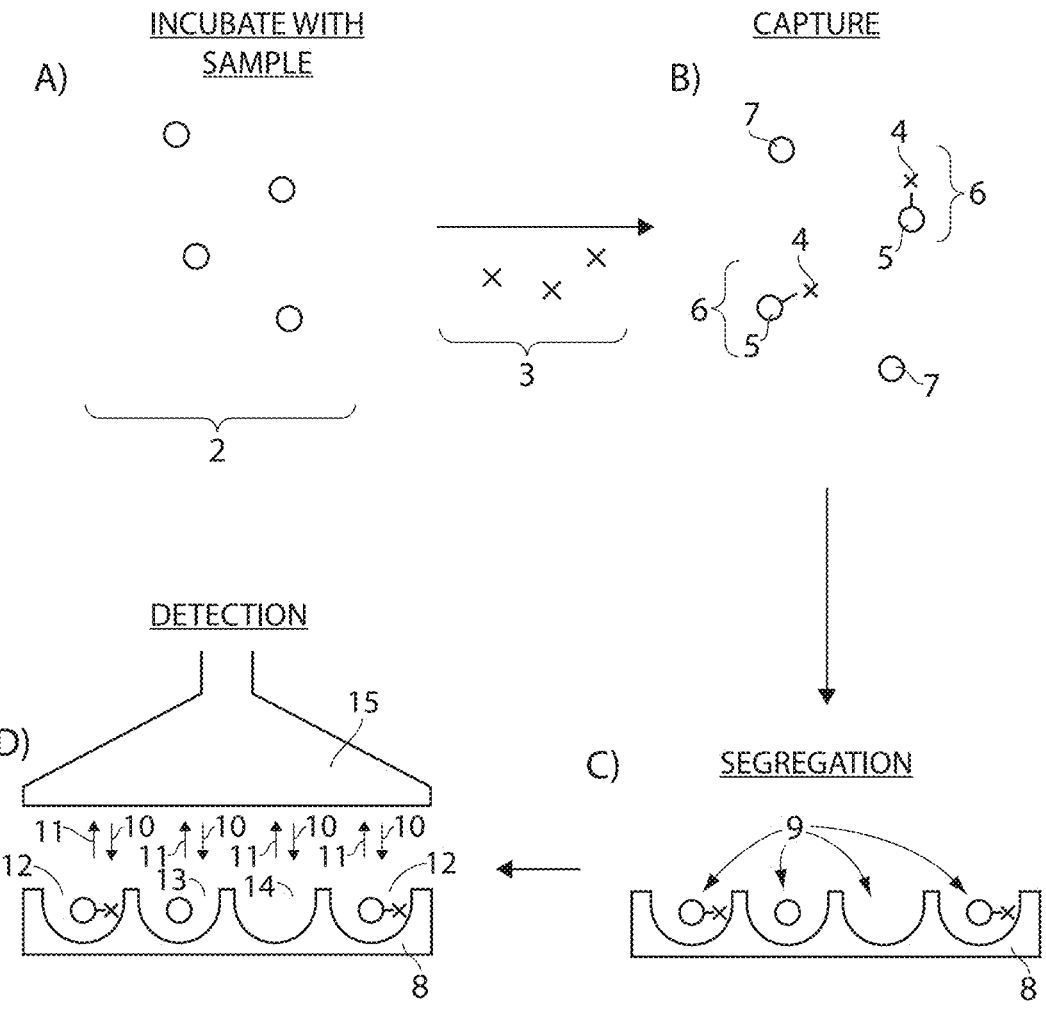
FIG. 1a is a schematic flow diagram depicting one embodiment of steps (A-D) for performing an exemplary method of the present invention.

Other aspects, embodiments, and features of the invention will become apparent from the following detailed description when considered in conjunction with the accompanying drawings. The accompanying figures are schematic and are not intended to be drawn to scale. For purposes of clarity, not every component is labeled in every figure, nor is every component of each embodiment of the invention shown where illustration is not necessary to allow those of ordinary skill in the art to understand the invention. All patent applications and patents incorporated herein by reference are incorporated by reference in their entirety. In case of conflict, the present specification, including definitions, will control.

DETAILED DESCRIPTION

The present invention generally relates to methods of determining a treatment protocol for and/or a prognosis of a patient's recovery from a brain injury. In some embodiments, the brain injury may result from a hypoxic event. In some embodiments, methods are provided for determining a measure of the concentration of tau protein in a patient sample containing or suspected of containing tau protein. The subject matter of the present invention involves, in some cases, interrelated products, alternative solutions to a particular problem, and/or a plurality of different uses of one or more systems and/or articles.

In some embodiments, a method of the present invention comprises determining a measure of the concentration of at least one biomarker in one or more samples obtained from a patient following a brain injury. In some embodiments, a method of the present invention comprises determining a measure of the concentration of at least one biomarker in one or more samples obtained from a patient following the brain injury (e.g., optionally resulting from a hypoxic event). A prognostic indication of the patient's recovery and/or determining a course of treatment (e.g., from the brain injury, optionally resulting from a hypoxic event) may be based at least in part on the measure of the concentration of the at least one biomarker present in the one or more samples. It should be understood, that while much of the discussion below is directed to methods involving the analysis of more than one sample, this is by way of example only, and similar methods may be employed wherein only a single sample is employed.

As will be known to those of ordinary skill in the art, the term "hypoxia" generally refers to a deficiency in the amount of oxygen reaching body tissues or a condition of insufficient levels of oxygen in tissue or blood. Hypoxia at a cellular level develops when delivery of oxygen to cell mitochondria slows as the partial pressure gradient from capillaries to tissues decreases. As the delivery of oxygen decreases, aerobic metabolism stops and less efficient anaerobic pathways of glycolysis become responsible for the production of cellular energy. The end result is an increase in cellular concentrations of sodium, calcium, and hydrogen ions which may lead to cell death.

Oxygen deprivation to the brain results in neuronal damage and death. The extent of neuronal damage and death in turn relates to the extent of long term brain dysfunction, as can be assessed using standard criteria (such as Cerebral Performance Category, CPC rating, or like criteria). Severe hypoxia can result in a patient's death and/or an irreversible brain injury (e.g., resulting in the patient being in a vegetative state). Hypoxic events may be global (e.g., due to low oxygen content in the blood) or focused (e.g., affecting only an area of the brain). Causes of hypoxia include, but are not limited to, local asphyxia (e.g., caused by smoke inhalation), carbon monoxide poisoning and/or toxicity, cardiac arrest, choking, drowning, high altitudes, strangulation, an ischemic event, thrombosis, arterial embolism, hemorrhage, swelling of the brain, stroke, physical trauma and/or physical injury (e.g., blunt trauma to the head), arteriosclerosis, and/or atherosclerosis. In some cases, the event may be myocardial infarction, myocardial ischemia, and/or transient ischemic attack.

Hypoxic conditions can lead to the production and/or change in the concentration of certain biomarkers. That is, the concentration of certain biomarkers increase or decrease following the hypoxic event. For example, the production of the proteolytic products of β-amyloid precursor protein has been found to become elevated in the brain and central nervous system under hypoxic condition. The increased concentration is theorized to be due to a hypoxia-inducible factor (HIF-1) that promotes the production of beta-amyloid peptides from amyloid precursor protein, a membrane protein concentrated in neuronal synapses. A cascade of biomarkers, such as tau proteins, is generated in the brain in proportion to the extent of hypoxia. Such biomarkers could in turn diffuse across the blood brain barrier and into the blood in proportion to the extent of hypoxia, and may be generally found in low abundance. The ability to determine a change in the concentration of a biomarker in a plurality of samples (or a single sample) obtained from a patient following a hypoxic event can, in some embodiments, be correlated with a prognostic indication of the patient's recovery from a brain injury and/or used to determine a method of treatment. In some cases, sample(s) of the patient's cerebrospinal fluid (CSF) may be obtained and analyzed to determine the concentration and/or a change in the concentration of the biomarker. In some cases, however, it is advantageous to determine the level of a biomarker in the blood of a patient as compared to CSF, as blood sampling is generally less invasive and may result in fewer complications as compared to CSF sampling. However, many of the biomarkers that are present in the CSF have a slow rate of transmission across and/or a high barrier of transportation across the blood-brain barrier (BBB) and thus, the concentration of the biomarker in the patient's blood may be sufficiently lowered as compared to the concentration in CSF to make it difficult or impossible to accurately determine using typically employed conventional immunoassays. Accordingly, assay methods which have very low limits of quantification (LOQ) and/or limits of detection (LOD) are generally necessary to determine a measure of the concentration of a biomarker in the patient's blood to provide statistically significant and/or meaningful results. In some embodiments, the methods of the present invention make use of methods having very low LODs and/or LOQs (e.g., in the low pg/mL range) to determine a measure of the concentration of a biomarker in a sample(s) obtained from a patient following a hypoxic event. Various parameters related to the changes in the concentration of the biomarker in the samples (e.g., blood samples) may be correlated with a prognostic indication and/or a method of treatment following a hypoxic event. Correlations (e.g., between the concentration and prognostic indication(s) and/or between the concentration and method(s) of treatment) have been discovered and/or are now discoverable due to recent advancements in technology which allow for the determination of the low concentrations of biomarkers in bodily fluids with sufficient accuracy and precision, thus allowing for the variations in concentration to be statistically significant and therefore, diagnostic.

It should be noted, that while many of the embodiments described herein focus on brain injuries caused by hypoxic events, this is by no way limiting, and in some embodiments, the brain injury may be caused by other events, for example, traumatic brain injuries wherein the force is such that the skull fractures causing mechanical damage to the brain. In some cases, a traumatic brain injury may be caused by external mechanical force, such as rapid acceleration or deceleration, impact, blast waves, or penetration by a projectile.

In embodiments where a plurality of samples are obtained from a patient, the samples may be obtained from a patient over any suitable period of time. Generally, the period of time may be selected such that the concentration of a biomarker in the samples becomes statistically significant and/or a trend is observable (e.g., an increase and/or decrease in the concentration). For biomarkers which are analyzed in blood samples, the period of time over which a plurality of samples are obtained from the patient may account for any lag time required for the biomarker to cross the BBB. Non-limiting examples of suitable periods of time in which the samples may be obtained from the patient include 1 hour, 2 hours, 3 hours, 4 hours, 6 hours, 8 hours, 10 hours, 12 hours, 18 hours, 24 hours, 36 hours, 48 hours, 60 hours, 72 hours, 4 days, 5 days, 6 days, 7 days, or more. In some cases, the duration of time of sample collection time is at least 60 hours, or at least 72 hours. In some cases, the duration of time of sample collection is between 12 hours and 7 days, or between 24 hours and 4 days, or between 2 days and 4 days, or between 3 days and 4 days. The first sample may be obtained from the patient without a short timeframe following the brain injury. For example, the first sample may be obtained from the patient within 1 hour, 2 hours, 3 hours, 4 hours, 5 hours, 6 hours, 8 hours, 10 hours, or 12 hours of the brain injury. In some cases, the first sample is obtained within 6 hours of the brain injury. In some embodiments, a first sample is obtained from the patient within 6 hours of the suspected brain injury, and at about 1, about 2, about 6, about 12, about 24, about 48, and about 72 hours, following the first sampling. In some embodiments, additional samples are obtained at about 96 and/or at about 108 hours following the first sampling.

Any number of samples (e.g., one or more) may be obtained from the patient over the time period of sample collection. Generally, the minimum number of samples obtained is such that a trend (e.g., an increase or decrease) in the concentration of the biomarker is observable. Non-limiting examples of the number of samples that are obtained from the patient (e.g., during the prescribed collection time) is at least about 1, about 2, at least about 3, at least about 4, at least about 5, at least about 6, at least about 7, at least about 8, at least about 9, at least about 10, at least about 12, at least about 15 or more. In some cases, the number of samples obtained from the patient is between 2 and 20, between 5 and 15, or between 5 and 10.

The sample(s) obtained from the patient may be from any suitable bodily source. In some cases, the samples are CSF fluid samples. In some cases, the samples are not CSF fluid samples. In some cases, the samples are blood or blood products (e.g., whole blood, plasma, serum, etc.). In other cases, the samples may be urine or saliva samples. In some embodiments, the samples may be analyzed directly (e.g., without the need for extraction of the biomarker from the fluid sample) and/or with dilution (e.g., addition of a buffer or agent to the sample). Generally, each of the samples obtained from the patient is collected using substantially similar procedures (e.g., to ensure minimal variation between samples based on sample collection methods). Those of ordinary skill in the art will be aware of suitable systems and methods for obtaining a sample from a patient.

Each of or substantially all of the samples may be analyzed using an assay method (e.g., as described herein) to determine a measure of the concentration of at least one biomarker in each, a subset of or substantially all of the samples. In some cases, the methods comprise determining a measure of the concentration of a single biomarker in the samples. In other cases, a method comprises determining a measure of the concentration of more than one biomarker in each, a subset of or substantially all of the samples. For example, a measure of the concentration of 2, 3, 4, 5, 6, 7, 8, 9, 10, or more, biomarkers may be determined in the samples.

In some embodiments, the methods of the present invention comprise determining a prognostic indication based at least in part on the measured concentration of the at least one biomarker in the samples. In some cases, the prognostic indication may be correlated with standard criteria employed to define long-term brain dysfunction and/or injury. Those of ordinary skill in the art will be aware of such criteria, for example, cerebral performance category ratings ("CPC rating"), or more specifically, Glasgow-Pittsburgh cerebral performance category ratings (or scale) (e.g., see Teasdale G, Jennett B (1974); *Assessment of coma and impaired consciousness*; Lancet 2 (7872): 81-84). The CPC scale ranges from 1 to 5, with 1 representing a slight possibility of neurological deficit and 5 representing severe deficit and/or death. In some methods of the present invention, the prognostic indication of the patient's recovery from the brain injury is classified as either "good" (e.g., correlating to a CPC score of 1 or 2) corresponding to a high likelihood of recovery and/or returning to independent living, or "poor" (e.g., correlating to a CPC score of 3, 4, or 5) corresponding to little possibility of a full recovery and resulting in assisted living and/or death.

In the CPC scale, a rating of 1 is generally classified as good cerebral performance. The patient is conscious and alert, is able to work, but may have mild neurological or psychological deficit. A rating of 2 is generally classified as having moderate cerebral disability. The patient is conscious and has sufficient cerebral function for independent activities of daily life, and is generally able to work in sheltered environment. A rating of 3 corresponds to severe cerebral disability. While the patient is conscious, they generally depend on others for daily support because of impaired brain function. The patient may have abilities ranging from ambulatory state to severe dementia or paralysis. A rating of 4 corresponds to a coma or vegetative state. The patient is generally unaware, even if they appear awake (e.g., the patient is in a vegetative state) without interaction with environment and is cerebral unresponsive. A rating of 5 refers to brain death, associated with apnea, areflexia, and/or EEG silence. The CPC scale is summarized in Table 1.

TABLE 1

| CPC Scale Summary | |
|---|---|
| CPC Score | Description |
| 1 | Conscious and alert with normal function or only slight disability |
| 2 | Conscious and alert with moderate disability |
| 3 | Conscious with severe disability |
| 4 | Comatose or persistent vegetative state |
| 5 | Brain dead or death from other causes |

Other non-limiting examples of suitable criteria include the "scale g" criteria (e.g., see Dekaban AS, Robinson CE.; Application of a new rating scale of brain dysfunction to monitoring rehabilitation in 65 patients with severe head injury, Bull Clin Neurosci., 1984; 49, 82-92), the "Rancho Los Amigos Scale," and the "Disabilities Rating Scale."

In addition to the biomarkers specifically mentioned herein, those of ordinary skill will be aware of other suitable biomarkers to use in connection with the methods described herein. As described herein, the biomarker generally undergoes a change in concentration as a result of a hypoxic event. For example, the concentration of the biomarker may increase or decrease as a result of the brain injury. Non-limiting examples of biomarkers include neuron specific neuronal enolase (NSE), β-site aPP-cleaving enzyme 1 (BACe1), S100B, myelin basic protein (MBP), growth associated protein 43, glutamine synthetase, glial fibrillary acid protein (GFAP), glycine transporter (e.g., GLYT1, GLYT2), neuron specific glycoprotein (e.g., GP50), calpain, neurofibrillary protein, heat shock protein 72, beta-amyloid precursor proteins, calbindin D-28K, proteolipid protein, myeline associated glycoprotein, neurofilament H, creatine kinase protein (e.g., CK-BB), tau proteins (including phosphorylated taus such as p-tau-181 or p-tau-231), and endothelium membrane proteins (e.g., thrombomodulin).

Figure 4:
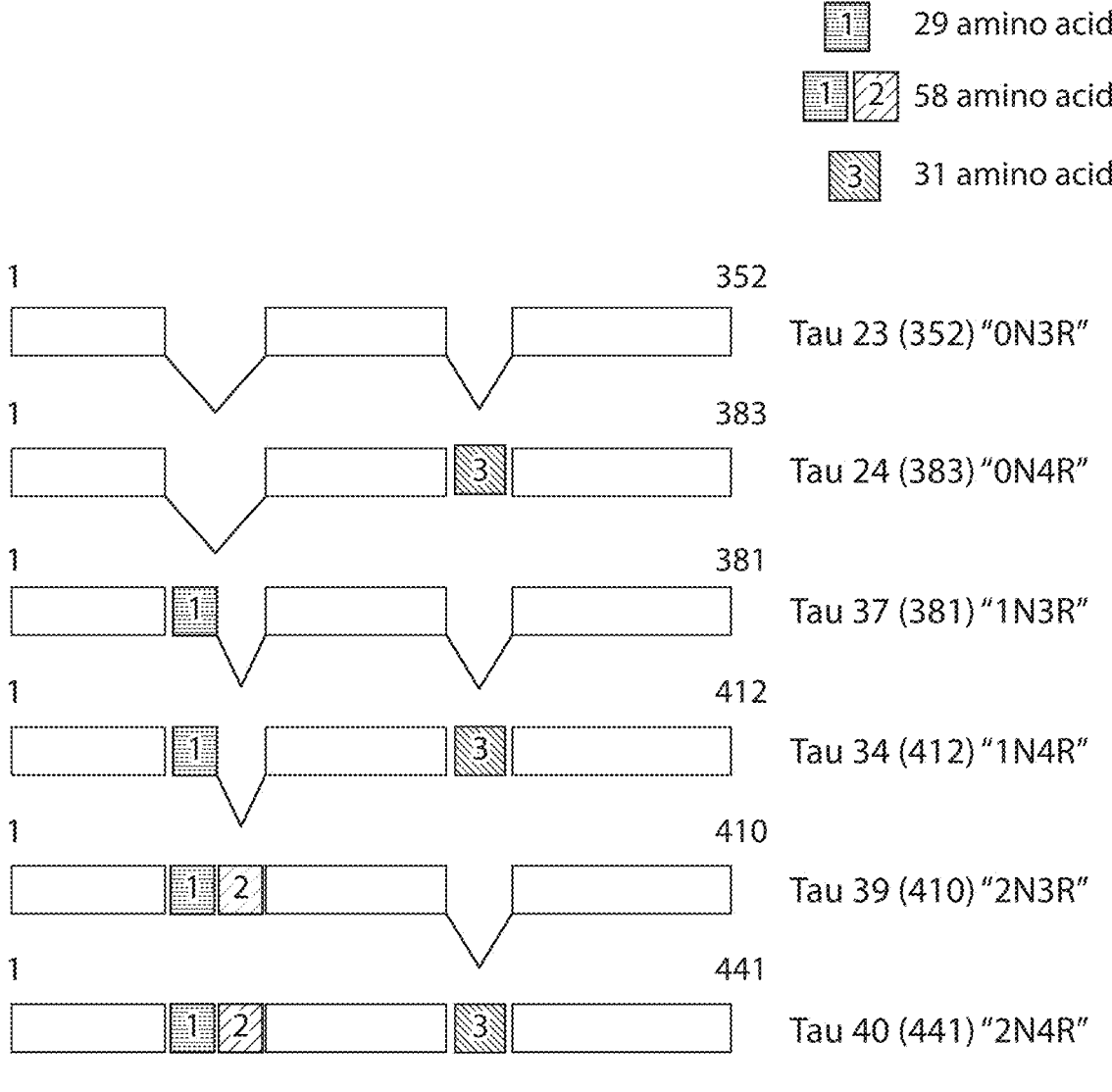
FIG. 4 illustrates six naturally occurring isoforms of tau proteins.

In some cases, the biomarker is a tau protein. Various forms and/or combinations of tau proteins may be contemplated for use as a target biomarker with the methods described herein, include isoforms and short isoforms, for example, ranging from tau 23 (352a.a, "0N3R", wherein R indicates the number of repeats and N indicates the number or amino terminal inserts, as will be understood by those of ordinary skill in the art) to tau 40 (441a.a. "2N4R"). There are six known naturally-occurring tau proteins, the sequences of which are well known in the art. The six tau proteins include tau 23 (352, 0N3R), tau 24 (383, 0N4R), tau 37 (381, 1N3R), tau 34 (412, 1N4R), tau 39 (410, 2N3R), tau 40 (441, 2N4R), and/or combinations thereof (e.g., see FIG. 4). In some cases, at least some of the tau proteins may be phosphorylated.

Those of ordinary skill in the art will understand that determination of a biomarker in a sample may comprise determining the concentration of a single isoform of a biomarker, or alternatively, may comprise determining the concentration of a plurality of isoforms of the biomarker. For example, with respect to tau proteins, in some cases, the concentration of tau protein employed in the algorithms and methods described herein may be the concentration of a single isoform of tau protein in the sample, or alternatively, the concentration of tau protein employed in the algorithms and methods described herein may be the concentration of a plurality of forms of tau proteins in the sample.

The plurality of samples obtained from the patient may be analyzed (e.g., using an assay method as described herein) to determine a measure of the concentration of the at least one biomarker in each of the samples (or a single sample). A prognostic indication and/or a method of treatment may be determined based at least in part on the measure of the concentration of the biomarker in each of the plurality of samples. The data may be analyzed using a variety of techniques, as described herein, and a prognostic indication for recovery from a brain injury (e.g., a "good" outcome or a "poor" outcome), or a specific method of treatment may be determined based on the results.

In some embodiments, the measure of the concentration of the at least one biomarker for each of the plurality of samples obtained from the patient may be plotted on a graph of concentration versus time (e.g., in hours), and one or more parameters can be obtained from the graph and used to determine the method of treatment and/or the prognostic indication. Non-limiting examples of parameters that may be determined and/or employed include baseline biomarker concentration, increase in biomarker concentration, duration of rise of biomarker concentration, maximum slope of increasing biomarker concentration, rate of change of biomarker concentration, area under the curve and/or magnitude of the fold increase of biomarker concentration. Each of the parameters and their determination will now be described in detail, followed by a description of possible data analysis and methods useful or potentially useful to determine suitable correlations between the measure of the concentration determined in the samples and a treatment/prognostic indication. The measure of the concentration of the biomarker may be determined/displayed in any suitable unit. In some cases, the measure of the concentration is determined/displayed in pg/mL.

The term "baseline biomarker concentration" refers to the concentration of the biomarker generally present in a fluid sample from a normal patient (e.g., prior to or unexposed to a hypoxic event). The baseline biomarker concentration can be determined using a variety of methods which will be commonly known and understood by those of ordinary skill in the art. In some cases, the baseline biomarker concentration can be determined by averaging the value of a biomarker present in a population of control patients (e.g., patients who have not experienced a hypoxic event). This may be useful in embodiments where the baseline concentration of the biomarker is substantially the same for a given population of individuals (e.g., based on age, gender, medical condition, etc.). However, many of the methods described herein require accurate determination of extremely low concentrations of the at least one biomarker in samples obtained from a patient, and accordingly, a general baseline concentration of a biomarker (e.g., based on a sampling of a population) may not provide enough accuracy and/or precision to give useful results. Accordingly, a measure of the baseline biomarker concentration, in some embodiments, may be determined for each individual patient. In some embodiments, the baseline biomarker concentration may be set to zero, e.g., in embodiments where the concentration of the biomarker is zero or essentially zero in normal patients.

In some cases, the baseline biomarker concentration for each individual is equal to the measure of the concentration of the biomarker in the first sample obtained from the patient following the hypoxic event. In other cases, if available, a baseline biomarker concentration is the measure of the concentration of the biomarker present in a sample obtained from the patient prior to the hypoxic event. In yet other cases, the baseline biomarker concentration is the average concentration of the biomarker determined in a plurality of samples taken from the patient immediately or substantially immediately following the hypoxic event (e.g., prior to the concentration of the biomarker increasing due to the hypoxic event). That is, the concentration of the biomarker in the plurality of samples obtained from the patient in a selected time period following the hypoxic event may be averaged to determine the baseline biomarker concentration for that patient. As will be understood by those of ordinary skill in the art, in such cases, any sample which has a concentration level that significantly differs from the other concentration levels during that period of time (e.g., a data point/outlier having a concentration which deviates significantly from the other concentrations measured during the time frame) may be excluded from the averaging calculation. In some cases, if a sample has a concentration which differs by greater than about 50% from the calculated average, that sample may be excluded from the averaging calculation. In some cases, if a sample has a concentration which differs by more than about 0.5 pg/mL, about 1 pg/mL, about 2 pg/mL, about 5 pg/mL, or about 10 pg/mL from the calculated average, that sample may be excluded from the averaging calculation. An anomalous data point may be observed and/or caused by administration of drugs to the patient. The baseline biomarker concentration may be determined by averaging the concentration of the biomarker in the samples obtained from the patient between the first sample (e.g., obtained within 6 hours of the hypoxic event) and 24 hours following the first collection of a sample, or between the first sample and 18 hours following the first collection of a sample, or between the first sample, and 12 hours following the first collection of a sample, or between the first sample, and 6 hours following the first collection of a sample (e.g., not including any outliers).

The term "area under the curve." (or AUC) is a common parameter used to analyze data, and such calculations will be well known and understood by those of ordinary skill in the art. In context with the methods of this disclosure, the AUC refers to the area under the biomarker concentration versus time curve. Generally the calculation takes into account the baseline biomarker concentration. Those of ordinary skill it the art will be aware of suitable algorithms and/or computer programs capable of determining the area under the curve for a selected set of data. In some cases, the area under the curve may be determined for more than one portion of the data. For example, a first area under the curve value may be determined for a first range of data, and a second area under the curve value may be determined for a second range of data. The first and the second ranges of data may or may not be overlapping (e.g., may comprise some overlapping data points or may comprise different data points). It should be understood, that determining the area under the curve can be accomplished using a variety of techniques which will be known to those of ordinary skill in the art, including but not limited to, plotting the concentration versus time on a graph and determining the area under the line/curve (e.g., optionally with use of a computer program) and/or determining a functional relationship between the concentration and time and integrating the data without requiring physically plotting or drawing of a graph. As used herein, the phrase "determining the area under the curve of a graph of a biomarker concentration versus time" covers all of the above techniques and others applicable for determining the area or equivalent, and is not limited to physically or electronically plotting the concentration versus time on a graph and determining the area under the line/curve.

The term "change in biomarker concentration" refers to the change (e.g., increase or decrease) in concentration of the biomarker over the time period in which the samples are collected. An increase in biomarker concentration may be calculated by subtracting the baseline biomarker concentration (e.g., as described herein) from the maximum biomarker concentration. The "maximum biomarker concentration" is the maximum measured concentration of the biomarker measured in a single sample collected over the duration of the sample collection. For example, if the duration of the sample collection is 72 hours, the maximum concentration is equal to the maximum measured concentration in a single sample which was obtained from the patient in the 72 hour period. A decrease in biomarker concentration may be calculated by subtracting an elevated biomarker concentration (e.g., as described herein) from the minimum biomarker concentration.

The term "magnitude of the fold increase of biomarker concentration" refers to the magnitude of the fold-increase in concentration over the duration of sample collection, and may be calculated by dividing the maximum biomarker concentration (e.g., as described herein) by the baseline biomarker concentration (e.g., as described herein).

The term "duration of rise of biomarker concentration" refers to the time over which the concentration of the biomarker is increasing during the time period over which the samples are collected. In some cases, the duration of rise of biomarker concentration can be determined by subtracting the time at which the last sample was collected at approximately the baseline biomarker concentration (e.g., starting time of the rise) from the time at which the maximum biomarker concentration was observed (e.g., ending time of the rise). That is, the duration of the rise may be equal to the ending time of the rise minus the starting time of the rise. The duration of rise is generally provided in hours.

The term "maximum slope of increasing biomarker concentration" refers to the slope at which the maximum increase in concentration occurred over the time period in which the samples were collected. Those of ordinary skill will be aware of methods to calculate this value using common graphical analysis methods. For example, a plot may be prepared showing concentration versus time, and the maximum slope may be calculated based on this plot. In some cases, the maximum slope is equal to the slope between two data points, whereas in other cases, the maximum slope may be determined based on the average slope between a plurality of data points.

The above parameters, alone or in combination, may be correlated to a prognostic indication and/or a method of treatment for a patient following a brain injury (e.g., caused by a hypoxic event). Following determination of a correlation between biomarker concentrations and a prognostic indication and/or a method of treatment (e.g., using a plurality of samples obtained from a plurality of test patients with known outcomes), the correlation can be used in connection with methods to determine prognosis (e.g., prognostic indications) and/or methods of treatment for patients with unknown outcomes. That is, an algorithm can be developed relating changes in a biomarker concentration and specific methods of treatment and/or prognostic indications using samples from test patients having been subject to known methods of treatment and/or having a known prognosis. Once the algorithm has been developed, it can be used to determine methods of treatment and/or prognostic indications for patients with unknown outcomes.

To determine a correlation between a biomarker and a prognostic indication and/or a method of treatment (e.g., to develop an algorithm relating the measured biomarker concentration to preferred methods of treatment and/or prognostic indications), a plurality of samples from a plurality of test patients may be obtained. A "test patient" is a patient who has a known outcome (e.g., a good or a poor CPC score) and/or has received a certain treatment. The plurality of the samples obtained from each of the test patients may be analyzed to determine the measure of the concentration of at least one biomarker in the each of the samples. Some or all of the parameters described herein may be determined for each patient, and the data may be analyzed to determine correlations between the parameters and the patient outcomes and/or treatments, which can in turn be used to develop an algorithm. The algorithm may then be applied to the concentration of the at least one biomarker in samples obtained from a patient having an unknown outcome to determine a method of treatment and/or a prognostic indication for that patient. A specific example of such an analysis is described below, and further details are provided in Example 1.

Similar analysis and methods may be used to correlate suitable methods of treatment based upon the measured concentration(s) of a biomarker in a plurality of samples obtained from a patient. In some cases, the method of treatment may comprise administering at least one therapeutic agent to the patient. For example, the therapeutic agent may be a neuroprotective drug. Other non-limiting methods of treatment include administration of anti-oxidants, hypothermia, blood thinning, and administration of steroids (e.g., to help reduce brain swelling) (e.g., see T. S. Richmond, Cerebral Resuscitation After Global Brain Ischemia: Linking Research to Practice, American Association of Critical-Care Nurses Journal, May 1997, Volume 8, Number 2).

A therapeutic agent is generally administered in an amount effective to provide a medically desirable result. The effective amount will vary with the particular condition being treated, the age and physical condition of the subject being treated, the severity of the condition, the duration of the treatment, the nature of the concurrent therapy (if any), the specific route of administration and the like factors within the knowledge and expertise of the health care practitioner. In some cases, a therapeutic agent may reduce brain injuries resulting from the hypoxic event. In some cases, the method of treatment may involve a change in treatment, such as an increase or decrease in the dose of a therapeutic agent, a switch from one therapeutic agent to another therapeutic agent, an addition of another therapeutic agent to the existing therapeutic agent, or a combination thereof. A switch from one therapeutic agent to another may involve a switch to a therapeutic agent with a high risk profile but where the likelihood of expected benefit is increased.

In one embodiment, a method of the present invention for determining a treatment protocol for and/or a prognostic indication of a patient's recovery from a brain injury (e.g., resulting from a hypoxic event) comprises performing an assay on a plurality of samples to determine a measure of the concentration of tau protein in each sample and determining a prognostic indication of the patient's recovery from the brain injury and/or a method of treatment based at least in part on the measure of the concentration of tau protein present in the samples. The sample, in some embodiments, is a blood sample from the patient and/or plasma and/or serum derived from the blood sample. In some cases, the concentration of the tau protein in the samples is less than about or about 1000 pg/mL, less than about or about 900 pg/mL, less than about or about 800 pg/mL, less than about or about 700 pg/mL, less than about or about 600 pg/mL, less than about or about 500 pg/mL, less than about or about 400 pg/mL, less than about or about 300 pg/mL, less than about or about 200 pg/mL, less than about or about 100 pg/mL, less than about or about 50 pg/mL, less than about or about 30 pg/mL, less than about or about 20 pg/mL, less than about or about 10 pg/mL, less than about or about 5 pg/mL, less than about or about 1 pg/mL, or less. In some cases, the assay has a limit of quantification of less than about or about 100 pg/mL, less than about or about 50 pg/mL, less than about or about 40 pg/mL, less than about or about 30 pg/mL, less than about or about 20 pg/mL, less than about or about 10 pg/mL, less than about or about 5 pg/mL, less than about or about 4 pg/mL, less than about or about 3 pg/mL, less than about or about 2 pg/mL, less than about or about 1 pg/mL, less than about or about 0.8 pg/mL, less than about or about 0.7 pg/mL, less than about or about 0.6 pg/mL, less than about or about 0.5 pg/mL, less than about or about 0.4 pg/mL, less than about or about 0.3 pg/mL, less than about or about 0.2 pg/mL, less than about or about 0.1 pg/mL, less than about or about 0.05 pg/mL, less than about or about 0.04 pg/mL, less than about or about 0.02 pg/mL, less than about or about 0.01 pg/mL, or less. In some cases, the assay has a limit of detection of less than about or about 100 pg/mL, less than about or about 50 pg/mL, less than about or about 40 pg/mL, less than about or about 30 pg/mL, less than about or about 20 pg/mL, less than about or about 10 pg/mL, less than about or about 5 pg/mL, less than about or about 4 pg/mL, less than about or about 3 pg/mL, less than about or about 2 pg/mL, less than about or about 1 pg/mL, less than about or about 0.8 pg/mL, less than about or about 0.7 pg/mL, less than about or about 0.6 pg/mL, less than about or about 0.5 pg/mL, less than about or about 0.4 pg/mL, less than about or about 0.3 pg/mL, less than about or about 0.2 pg/mL, less than about or about 0.1 pg/mL, less than about or about 0.05 pg/mL, less than about or about 0.04 pg/mL, less than about or about 0.02 pg/mL, less than about or about 0.01 pg/mL, or less.

In one embodiment, a correlation was determined between certain parameters (e.g., area under the curve of a plot of tau protein concentration versus time) and a good (e.g., CPC rating 1 or 2) or a poor (e.g., CPC rating of 3, 4, or 5) prognostic indication. To determine the correlation, an assay was carried out on each of the samples obtained from a plurality of test patients having undergone a brain injury (e.g., resulting from a hypoxic event) (e.g., patients having a known outcome and/or having undergone a certain method of treatment following a brain injury). The first sample was taken within 6 hours of the brain injury (e.g., resulting from a hypoxic event), and additional samples were generally obtained at about 1, 2, 6, 12, 24, 48, and 72 hours following the first sample (and optionally, at 96 and/or 108 hours). Each of the test patients had a known prognostic outcome according to the CPC scale. For each test patient, a plot of the measured concentration of tau protein in pg/mL time in hours was prepared. The data was analyzed and the area under the curve of the tau protein concentration (in pg/mL) versus time (in hours) was determined for a variety of time ranges, and was determined to correlate with a "good" or "poor" prognosis for the patients. In some embodiments, the plot of the concentration of the tau protein versus time showed two peaks, one occurring mostly in the first 24 hours following the hypoxic event, and one occurring at some point following the first 24 hours following the hypoxic event. Thus, the area under the curve was determined for each patient for three ranges of time: 1) for the entire duration of the data collection, 2) for the first 24 hours, and 3) for the second peak in tau protein concentration (if present). Generally, the baseline used to determine the area under the curve for 1) and 2) was set to zero, whereas the baseline used to determine the area under the curve for 3) was set as the concentration of tau protein determined at the beginning of the rise of the second peak. For the total area under the curve, a value of greater than about 800 correlated with a poor prognosis (e.g., a CPC score of 3, 4, or 5) and a value of less than about 800 correlated with a good prognosis (e.g., a CPC score of 1 or 2). For the area under the curve of the second peak, a value of greater than about 500 correlated with a poor prognosis (e.g., a CPC score of 3, 4, or 5) and a value of less than about 500 correlated with a good prognosis (e.g., a CPC score of 1 or 2). Accordingly, a correlation/algorithm was established between the varying parameters relating to concentration and a prognostic indication.

The developed correlation/algorithm can be applied to patients with unknown outcomes. That is, samples may be obtained from a patient and the concentration of tau protein in each of the samples can be determined. The data may be analyzed to determine the total area under the curve and/or the area under the curve of the second tau protein peak. If the sum of the total area under the curve and/or the area under the curve of the second peak is greater than 800 or 500, respectively, the prognostic indication for that patient is "poor." and if the sum is less than 800 or 500, respectively, the prognostic indication is "good." Using similar techniques, a variety of correlations may be determined for this tau protein (e.g., increase in tau protein concentration, duration of the increase of tau protein concentration, and/or the magnitude of the fold increase of tau protein) and/or other biomarkers.

Exemplary Assay Methods and Systems

Those of ordinary skill in the art will be aware of a variety of assay methods and systems that may be used in connection with the methods of the present invention. Generally, the methods employed have low limits of detection and/or limits of quantification as compared to bulk analysis techniques (e.g., ELISA methods). The use of assay methods that have low limits of detection and/or limits of quantification allows for correlations to be made between the various parameters discussed above and a method of treatment and/or diagnostic indication that may otherwise not be determinable and/or apparent. For example, in the method described above which correlates the total area under the curve and/or the area under the curve of a second peak of tau protein concentration to a prognostic indication of brain injury, the limits of detection, and/or limits of quantification needs to be substantially lower than the LOD and/or LOQ provided by common ELISA techniques.

The terms "limit of detection" (or LOD) and "limit of quantification" (or LOQ) are given their ordinary meaning in the art. The LOD refers to the lowest analyte concentration likely to be reliably distinguished from background noise and at which detection is feasible. The LOD as used herein is defined as three standard deviations (SD) above background noise. The LOQ refers to the lowest concentration at which the analyte can not only be reliably detected but at which some predefined goals for bias and imprecision are met. Generally, as is used herein, the LOQ refers to the lowest concentration above the LOD wherein the coefficient of variation (CV) of the measured concentrations less than about 20%.

In some cases, an assay method employed has a limit of detection and/or a limit of quantification of less than about or about 500 pg/mL, less than about or about 250 pg/mL, less than about or about 100 pg/mL, less than about or about 50 pg/mL, less than about or about 40 pg/mL, less than about or about 30 pg/mL, less than about or about 20 pg/mL, less than about or about 10 pg/mL, less than about or about 5 pg/mL, less than about or about 4 pg/mL, less than about or about 3 pg/mL, less than about or about 2 pg/mL, less than about or about 1 pg/mL, less than about or about 0.8 pg/mL, less than about or about 0.7 pg/mL, less than about or about 0.6 pg/mL, less than about or about 0.5 pg/mL, less than about or about 0.4 pg/mL, less than about or about 0.3 pg/mL, less than about or about 0.2 pg/mL, less than about or about 0.1 pg/mL, less than about or about 0.05 pg/mL, less than about or about 0.04 pg/mL, less than about or about 0.02 pg/mL, less than about or about 0.01 pg/mL, or less. In some cases, an assay method employed has a limit of quantification and/or a limit of detection between about 100 pg/mL and about 0.01 pg/mL, between about 50 pg/mL and about 0.02 pg/mL, between about 25 pg/mL and about 0.02 pg/mL, between about 10 pg/mL and about 0.02 pg/mL. As will be understood by those of ordinary skill the art, the LOQ and/or LOD may differ for each assay method and/or each biomarker determined with the same assay. In some embodiments, the LOD of an assay employed for detecting tau protein is about equal to or less than 0.02 pg/mL. In some embodiments, the LOQ for an assay employed for detecting tau protein is equal to or less than 0.04 pg/mL In some embodiments, the concentration of biomarker molecules in the fluid sample that may be substantially accurately determined is less than about or about 5000 fM, less than about or about 3000 fM, less than about or about 2000 fM, less than about or about 1000 fM, less than about or about 500 fM, less than about or about 300 fM, less than about or about 200 fM, less than about or about 100 fM, less than about or about 50 fM, less than about or about 25 fM, less than about or about 10 fM, less than about or about 5 fM, less than about or about 2 fM, less than about or about 1 fM, less than about or about 0.5 fM, less than about or about 0.1 fM, or less. In some embodiments, the concentration of biomarker molecules in the fluid sample that may be substantially accurately determined is between about 5000 fM and about 0.1 fM, between about 3000 fM and about 0.1 fM, between about 1000 fM and about 0.1 fM, between about 1000 fM and about 1 fM, between about 100 fM and about 1 fM, between about 100 fM and about 0.1 fM, or the like. The concentration of analyte molecules or particles in a fluid sample may be considered to be substantially accurately determined if the measured concentration of the biomarker molecules in the fluid sample is within about 10% of the actual (e.g., true) concentration of the biomarker molecules in the fluid sample. In certain embodiments, the measured concentration of the biomarker molecules in the fluid sample may be within about 5%, within about 4%, within about 3%, within about 2%, within about 1%, within about 0.5%, within about 0.4%, within about 0.3%, within about 0.2% or within about 0.1%, of the actual concentration of the biomarker molecules in the fluid sample. In some cases, the measure of the concentration determined differs from the true (e.g., actual) concentration by no greater than about 20%, no greater than about 15%, no greater than 10%, no greater than 5%, no greater than 4%, no greater than 3%, no greater than 2%, no greater than 1%, or no greater than 0.5%. The accuracy of the assay method may be determined, in some embodiments, by determining the concentration of biomarker molecules in a fluid sample of a known concentration using the selected assay method.

In some embodiments, an assay method employs a step of spatially segregating biomarker molecules into a plurality of locations to facilitate detection/quantification, such that each location comprises/contains either zero or one or more biomarker molecules. Additionally, in some embodiments, the locations may be configured in a manner such that each location can be individually addressed. In some embodiments, a measure of the concentration of biomarker molecules in a fluid sample may be determined by detecting biomarker molecules immobilized with respect to a binding surface having affinity for at least one type of biomarker molecule. In certain embodiments the binding surface may form (e.g., a surface of a well/reaction vessel on a substrate) or be contained within (e.g., a surface of a capture object, such as a bead, contained within a well) one of a plurality of locations (e.g., a plurality of wells/reaction vessels) on a substrate (e.g., plate, dish, chip, optical fiber end, etc.). At least a portion of the locations may be addressed and a measure indicative of the number/percentage/fraction of the locations containing at least one biomarker molecule may be made. In some cases, based upon the number/percentage/fraction, a measure of the concentration of biomarker molecules in the fluid sample may be determined. The measure of the concentration of biomarker molecules in the fluid sample may be determined by a digital analysis method/system optionally employing Poisson distribution adjustment and/or based at least in part on a measured intensity of a signal, as will be known to those of ordinary skill in the art. In some cases, the assay methods and/or systems may be automated.

Certain methods and systems which employ spatially segregating analyte molecules (e.g., biomarkers) are known in the art, and are described in U.S. Patent Application Publication No. US-2007-0259448 (Ser. No. 11/707,385), filed Feb. 16, 2007, entitled "METHODS AND ARRAYS FOR TARGET ANALYTE DETECTION AND DETERMINATION OF TARGET ANALYTE CONCENTRATION IN SOLUTION," by Walt et al.; U.S. Patent Application Publication No. US-2007-0259385 (Ser. No. 11/707,383), filed Feb. 16, 2007, entitled "METHODS AND ARRAYS FOR DETECTING CELLS AND CELLULAR COMPONENTS IN SMALL DEFINED VOLUMES," by Walt et al.; U.S. Patent Application Publication No. US-2007-0259381 (Ser. No. 11/707,384), filed Feb. 16, 2007, entitled "METHODS AND ARRAYS FOR TARGET ANALYTE DETECTION AND DETERMINATION OF REACTION COMPONENTS THAT AFFECT A REACTION," by Walt et al.; International Patent Publication No. WO 2009/029073 (International Patent Application No. PCT/US2007/019184), filed Aug. 30, 2007, entitled "METHODS OF DETERMINING THE CONCENTRATION OF AN ANALYTE IN SOLUTION," by Walt et al.; U.S. Patent Application Publication No. US-2010-0075862 (Ser. No. 12/236,484), filed Sep. 23, 2008, entitled "HIGH SENSITIVITY DETERMINATION OF THE CONCENTRATION OF ANALYTE MOLECULES OR PARTICLES IN A FLUID SAMPLE," by Duffy et al.; U.S. Patent Application Publication No. US-2010-00754072 (Ser. No. 12/236,486), filed Sep. 23, 2008, entitled "ULTRA-SENSITIVE DETECTION OF MOLECULES ON SINGLE MOLECULE ARRAYS," by Duffy et al.; U.S. Patent Application Publication No. US-2010-0075439 (Ser. No. 12/236,488), filed Sep. 23, 2008, entitled "ULTRA-SENSITIVE DETECTION OF MOLECULES BY CAPTURE-AND-RELEASE USING REDUCING AGENTS FOLLOWED BY QUANTIFICATION," by Duffy et al.; International Patent Publication No. WO2010/039179 (International Patent Application No. PCT/US2009/005248), filed Sep. 22, 2009, entitled "ULTRA-SENSITIVE DETECTION OF MOLECULES OR ENZYMES," by Duffy et al.; U.S. Patent Application Publication No. US-2010-0075355 (Ser. No. 12/236,490), filed Sep. 23, 2008, entitled "ULTRA-SENSITIVE DETECTION OF ENZYMES BY CAPTURE-AND-RELEASE FOLLOWED BY QUANTIFICATION," by Duffy et al.; U.S. patent application Ser. No. 12/731,130, filed Mar. 24, 2010, published as US-2011-0212848 on Sep. 1, 2011, entitled "ULTRA-SENSITIVE DETECTION OF MOLECULES OR PARTICLES USING BEADS OR OTHER CAPTURE OBJECTS," by Duffy et al.; International Patent Application No. PCT/US2011/026645, filed Mar. 1, 2011, published as WO 2011/109364 on Sep. 9, 2011, entitled "ULTRA-SENSITIVE DETECTION OF MOLECULES OR PARTICLES USING BEADS OR OTHER CAPTURE OBJECTS," by Duffy et al.; International Patent Application No. PCT/US2011/026657, filed Mar. 1, 2011, published as WO 2011/109372 on Sep. 9, 2011, entitled "ULTRA-SENSITIVE DETECTION OF MOLECULES USING DUAL DETECTION METHODS," by Duffy et al.; U.S. patent application Ser. No. 12/731,135, filed Mar. 24, 2010, published as US-2011-0212462 on Sep. 1, 2011, entitled "ULTRA-SENSITIVE DETECTION OF MOLECULES USING DUAL DETECTION METHODS," by Duffy et al.; International Patent Application No. PCT/US2011/026665, filed Mar. 1, 2011, published as WO 2011/109379 on Sep. 9, 2011, entitled "METHODS AND SYSTEMS FOR EXTENDING DYNAMIC RANGE IN ASSAYS FOR THE DETECTION OF MOLECULES OR PARTICLES," by Rissin et al.; U.S. patent application Ser. No. 12/731,136, filed Mar. 24, 2010, published as US-2011-0212537 on Sep. 1, 2011, entitled "METHODS AND SYSTEMS FOR EXTENDING DYNAMIC RANGE IN ASSAYS FOR THE DETECTION OF MOLECULES OR PARTICLES," by Duffy et al.; U.S. patent application Ser. No. 13/035,472, filed Feb. 25, 2011, entitled "SYSTEMS, DEVICES, AND METHODS FOR ULTRA-SENSITIVE DETECTION OF MOLECULES OR PARTICLES," by Fournier et al.; U.S. patent application Ser. No. 13/037,987, filed Mar. 1, 2011, published as US-2011-0245097 on Oct. 6, 2011, entitled "METHODS AND SYSTEMS FOR EXTENDING DYNAMIC RANGE IN ASSAYS FOR THE DETECTION OF MOLECULES OR PARTICLES," by Rissin et al.; each herein incorporated by reference.

Additional details of exemplary, non-limiting assay methods which comprise one or more steps of spatially segregating biomarker molecules will now be described. In certain embodiments, a method for detection and/or quantifying biomarker molecules in a sample comprises immobilizing a plurality of biomarker molecules with respect to a plurality of capture objects (e.g., beads) that each include a binding surface having affinity for at least one type of biomarker. For example, the capture objects may comprise a plurality of beads comprising a plurality of capture components (e.g., an antibody having specific affinity for a biomarker of interest, etc.). At least some of the capture objects (e.g., at least some associated with at least one biomarker molecule) may be spatially separated/segregated into a plurality of locations, and at least some of the locations may be addressed/interrogated (e.g., using an imaging system). A measure of the concentration of biomarker molecules in the fluid sample may be determined based on the information received when addressing the locations (e.g., using the information received from the imaging system and/or processed using a computer implemented control system). In some cases, a measure of the concentration may be based at least in part on the number of locations determined to contain a capture object that is or was associated with at least one biomarker molecule. In other cases and/or under differing conditions, a measure of the concentration may be based at least in part on an intensity level of at least one signal indicative of the presence of a plurality of biomarker molecules and/or capture objects associated with a biomarker molecule at one or more of the addressed locations.

In some embodiments, the number/percentage/fraction of locations containing a capture object but not containing a biomarker molecule may also be determined and/or the number/percentage/fraction of locations not containing any capture object may also be determined. In such embodiments, a measure of the concentration of biomarker molecules in the fluid sample may be based at least in part on the ratio of the number of locations determined to contain a capture object associated with a biomarker molecule to the total number of locations determined to contain a capture object not associated with a biomarker molecule, and/or a measure of the concentration of biomarker molecule in the fluid sample may be based at least in part on the ratio of the number of locations determined to contain a capture object associated with a biomarker molecule to the number of locations determined to not contain any capture objects, and/or a measure of the concentration of biomarker molecule in the fluid sample may be based at least in part on the ratio of the number of locations determined to contain a capture object associated with a biomarker molecule to the number of locations determined to contain a capture object. In yet other embodiments, a measure of the concentration of biomarker molecules in a fluid sample may be based at least in part on the ratio of the number of locations determined to contain a capture object and a biomarker molecule to the total number of locations addressed and/or analyzed.

In certain embodiments, at least some of the plurality of capture objects (e.g., at least some associated with at least one biomarker molecule) are spatially separated into a plurality of locations, for example, a plurality of reaction vessels in an array format. The plurality of reaction vessels may be formed in, on and/or of any suitable material, and in some cases, the reaction vessels can be sealed or may be formed upon the mating of a substrate with a sealing component, as discussed in more detail below. In certain embodiments, especially where quantization of the capture objects associated with at least one biomarker molecule is desired, the partitioning of the capture objects can be performed such that at least some (e.g., a statistically significant fraction; e.g., as described in International Patent Application No. PCT/US2011/026645, filed Mar. 1, 2011, published as WO 2011/109364 on Sep. 9, 2011, entitled "ULTRA-SENSITIVE DETECTION OF MOLECULES OR PARTICLES USING BEADS OR OTHER CAPTURE OBJECTS," by Duffy et al) of the reaction vessels comprise at least one or, in certain cases, only one capture object associated with at least one biomarker molecule and at least some (e.g., a statistically significant fraction) of the reaction vessels comprise an capture object not associated with any biomarker molecules. The capture objects associated with at least one biomarker molecule may be quantified in certain embodiments, thereby allowing for the detection and/or quantification of biomarker molecules in the fluid sample by techniques described in more detail herein.

An exemplary assay method may proceed as follows. A sample fluid containing or suspected of containing bio-marker molecules is provided. An assay consumable comprising a plurality of assay sites is exposed to the sample fluid. In some cases, the biomarker molecules are provided in a manner (e.g., at a concentration) such that a statistically significant fraction of the assay sites contain a single bio-marker molecule and a statistically significant fraction of the assay sites do not contain any biomarker molecules. The assay sites may optionally be exposed to a variety of reagents (e.g., using a reagent loader) and or rinsed. The assay sites may then optionally be sealed and imaged (see, for example, U.S. patent application Ser. No. 13/035,472, filed Feb. 25, 2011, entitled "SYSTEMS, DEVICES, AND METHODS FOR ULTRA-SENSITIVE DETECTION OF MOLECULES OR PARTICLES," by Fournier et al.). The images are then analyzed (e.g., using a computer imple-mented control system) such that a measure of the concen-tration of the biomarker molecules in the fluid sample may be obtained, based at least in part, by determination of the number/fraction/percentage of assay sites which contain a biomarker molecule and/or the number/fraction/percentage of sites which do not contain any biomarkers molecules. In some cases, the biomarker molecules are provided in a manner (e.g., at a concentration) such that at least some assay sites comprise more than one biomarker molecule. In such embodiments, a measure of the concentration of bio-marker molecules in the fluid sample may be obtained at least in part on an intensity level of at least one signal indicative of the presence of a plurality of biomarkers molecules at one or more of the assay sites In some cases, the methods optionally comprise exposing the fluid sample to a plurality of capture objects, for example, beads. At least some of the biomarker molecules are immobilized with respect to a bead. In some cases, the biomarker molecules are provided in a manner (e.g., at a concentration) such that a statistically significant fraction of the beads associate with a single biomarker molecule and a statistically significant fraction of the beads do not associate with any biomarker molecules. At least some of the plurality of beads (e.g., those associated with a single biomarker molecule or not associated with any biomarker molecules) may then be spatially separated/segregated into a plurality of assay sites (e.g., of an assay consumable). The assay sites may optionally be exposed to a variety of reagents and/or rinsed. At least some of the assay sites may then be addressed to determine the number of assay sites containing a biomarker molecule. In some cases, the number of assay sites containing a bead not associated with a biomarker molecule, the number of assay sites not containing a bead and/or the total number of assay sites addressed may also be determined. Such determination(s) may then be used to determine a measure of the concentration of biomarker molecules in the fluid sample. In some cases, more than one biomarker molecule may associate with a bead and/or more than one bead may be present in an assay site. In some cases, the plurality biomarker molecules may be exposed to at least one additional reaction component prior to, concurrent with, and/or following spatially separating at least some of the biomarker molecules into a plurality of locations.

The biomarker molecules may be directly detected or indirectly detected. In the case of direct detection, a bio-marker molecule may comprise a molecule or moiety that may be directly interrogated and/or detected (e.g., a fluo-rescent entity). In the case of indirect detection, an addi-tional component is used for determining the presence of the biomarker molecule. For example, the biomarker molecules (e.g., optionally associated with a bead) may be exposed to at least one type of binding ligand. A "binding ligand." is any molecule, particle, or the like which specifically binds to or otherwise specifically associates with a biomarker molecule to aid in the detection of the biomarker molecule. In certain embodiments, a binding ligand may be adapted to be directly detected (e.g., the binding ligand comprises a detectable molecule or moiety) or may be adapted to be indirectly detected (e.g., including a component that can convert a precursor labeling agent into a labeling agent). A component of a binding ligand may be adapted to be directly detected in embodiments where the component comprises a measur-able property (e.g., a fluorescence emission, a color, etc.). A component of a binding ligand may facilitate indirect detec-tion, for example, by converting a precursor labeling agent into a labeling agent (e.g., an agent that is detected in an assay). A "precursor labeling agent" is any molecule, par-ticle, or the like, that can be converted to a labeling agent upon exposure to a suitable converting agent (e.g., an enzymatic component). A "labeling agent" is any molecule, particle, or the like, that facilitates detection, by acting as the detected entity, using a chosen detection technique. In some embodiments, the binding ligand may comprise an enzy-matic component (e.g., horseradish peroxidase, beta-galac-tosidase, alkaline phosphatase, etc.). A first type of binding ligand may or may not be used in conjunction with addi-tional binding ligands (e.g., second type, etc.).

More than one type of binding may be employed in any given assay method, for example, a first type of binding ligand and a second type of binding ligand. In one example, the first type of binding ligand is able to associate with a first type of biomarker molecule and the second type of binding ligand is able to associate with the first binding ligand. In another example, both a first type of binding ligand and a second type of binding ligand may associate with the same or different epitopes of a single biomarker molecule, as described herein. In some embodiments, at least one binding ligand comprises an enzymatic component.

In some embodiments, a binding ligand and/or a bio-marker may comprise an enzymatic component. The enzy-matic component may convert a precursor labeling agent (e.g., an enzymatic substrate) into a labeling agent (e.g., a detectable product). A measure of the concentration of biomarker molecules in the fluid sample can then be deter-mined based at least in part by determining the number of locations containing a labeling agent (e.g., by relating the number of locations containing a labeling agent to the number of locations containing a biomarker molecule (or number of capture objects associated with at least one biomarker molecule to total number of capture objects)). Non-limiting examples of enzymes or enzymatic compo-nents include horseradish peroxidase, beta-galactosidase, and alkaline phosphatase. Other non-limiting examples of systems or methods for detection include embodiments where nucleic acid precursors are replicated into multiple copies or converted to a nucleic acid that can be detected readily, such as the polymerase chain reaction (PCR), rolling circle amplification (RCA), ligation, Loop-Mediated Iso-thermal Amplification (LAMP), etc. Such systems and meth-ods will be known to those of ordinary skill in the art, for example, as described in "DNA Amplification: Current Technologies and Applications," Vadim Demidov et al., 2004.

Another exemplary embodiment of indirect detection is as follows. In some cases, the biomarker molecules may be exposed to a precursor labeling agent (e.g., enzymatic sub-strate) and the enzymatic substrate may be converted to a detectable product (e.g., fluorescent molecule) upon exposure to a biomarker molecule.

The assay methods and systems may employ a variety of different components, steps, and/or other aspects that will be known and understood by those of ordinary skill in the art. For example, a method may further comprise determining at least one background signal determination (e.g., and further comprising subtracting the background signal from other determinations), wash steps, and the like. In some cases, the assays or systems may include the use of at least one binding ligand, as described herein. In some cases, the measure of the concentration of biomarker molecules in a fluid sample is based at least in part on comparison of a measured parameter to a calibration curve. In some instances, the calibration curve is formed at least in part by determination at least one calibration factor, as described above.

As will be understood by those of ordinary skill in the art, a system and/or method may be calibrated using natural and/or synthetic forms of the target biomarker, and/or analogues thereof. In embodiments where the target analyte is a tau protein, the system and/or method may be calibrated using one or more natural and/or synthetic isoforms of tau protein. Naturally occurring tau proteins are described herein. Synthetic isoforms of tau proteins include two nearest neighbor antibody epitope synthetic peptides (<20 amino acids) to long synthetic peptides (80-100 amino acids in length. In some cases, short isoforms of the naturally occurring tau proteins may be employed. For example, tau protein isoforms can have varying lengths of amino acids selected from the tau 441 sequence. Non-limiting examples of short forms of tau proteins include tau 50-mers (e.g., comprising residues 187-237, 190-240, or 155-205 of tau 441) and tau 64-mers (e.g., comprising residues 155-235 of tau 441, RGAAP PGQKG QTPPA PKPTPP SSKSG DRSGY SSPGS PGTSR TPSLP TPPTR EPKKV AVVRT PPKS-NH₂ (SEQ ID NO.: 1)). In some cases, at least a portion of the tau protein(s) used may be phosphorylated (e.g., RGAAP PGQKG QTPPA PKPTPP SSKSG DRSGY SSPGS PGTSR TPSLP TPPTR EPKKV AVVRpT PPKS-NH2 (SEQ ID NO.: 2)).

In certain embodiments, solubilized, or suspended precursor labeling agents may be employed, wherein the precursor labeling agents are converted to labeling agents which are insoluble in the liquid and/or which become immobilized within/near the location (e.g., within the reaction vessel in which the labeling agent is formed). Such precursor labeling agents and labeling agents and their use is described in commonly owned U.S. Patent Application Publication No. US-2010-0075862 (Ser. No. 12/236,484), filed Sep. 23, 2008, entitled "HIGH SENSITIVITY DETERMINATION OF THE CONCENTRATION OF ANALYTE MOLECULES OR PARTICLES IN A FLUID SAMPLE," by Duffy et al., incorporated herein by reference.

An exemplary embodiment of an assay method that may be used in certain embodiments of the invention is illustrated in FIG. 1a. A plurality of capture objects 2, are provided (step (A)). In this particular example, the plurality of capture objects comprises a plurality of beads. The beads are exposed to a fluid sample containing a plurality of biomarker molecules 3 (e.g., beads 2 are incubated with biomarker molecules 3). At least some of the biomarker molecules are immobilized with respect to a bead. In this example, the biomarker molecules are provided in a manner (e.g., at a concentration) such that a statistically significant fraction of the beads associate with a single biomarker molecule and a statistically significant fraction of the beads do not associate with any biomarker molecules. For example, as shown in step (B), biomarker molecule 4 is immobilized with respect to bead 5, thereby forming complex 6, whereas some beads 7 are not associated with any biomarker molecules. It should be understood, in some embodiments, more than one biomarker molecule may associate with at least some of the beads, as described herein. At least some of the plurality of beads (e.g., those associated with a single biomarker molecule or not associated with any biomarker molecules) may then be spatially separated/segregated into a plurality of locations. As shown in step (C), the plurality of locations is illustrated as substrate 8 comprising a plurality of wells/reaction vessels 9. In this example, each reaction vessel comprises either zero or one beads. At least some of the reaction vessels may then be addressed (e.g., optically or via other detection means) to determine the number of locations containing a biomarker molecule. For example, as shown in step (D), the plurality of reaction vessels are interrogated optically using light source 15, wherein each reaction vessel is exposed to electromagnetic radiation (represented by arrows 10) from light source 15. The light emitted (represented by arrows 11) from each reaction vessel is determined (and/or recorded) by detector 15 (in this example, housed in the same system as light source 15). The number of reaction vessels containing a biomarker molecule (e.g., reaction vessels 12) is determined based on the light detected from the reaction vessels. In some cases, the number of reaction vessels containing a bead not associated with a biomarker molecule (e.g., reaction vessel 13), the number of wells not containing a bead (e.g., reaction vessel 14) and/or the total number of wells addressed may also be determined. Such determination(s) may then be used to determine a measure of the concentration of biomarker molecules in the fluid sample.

Figure 1B:
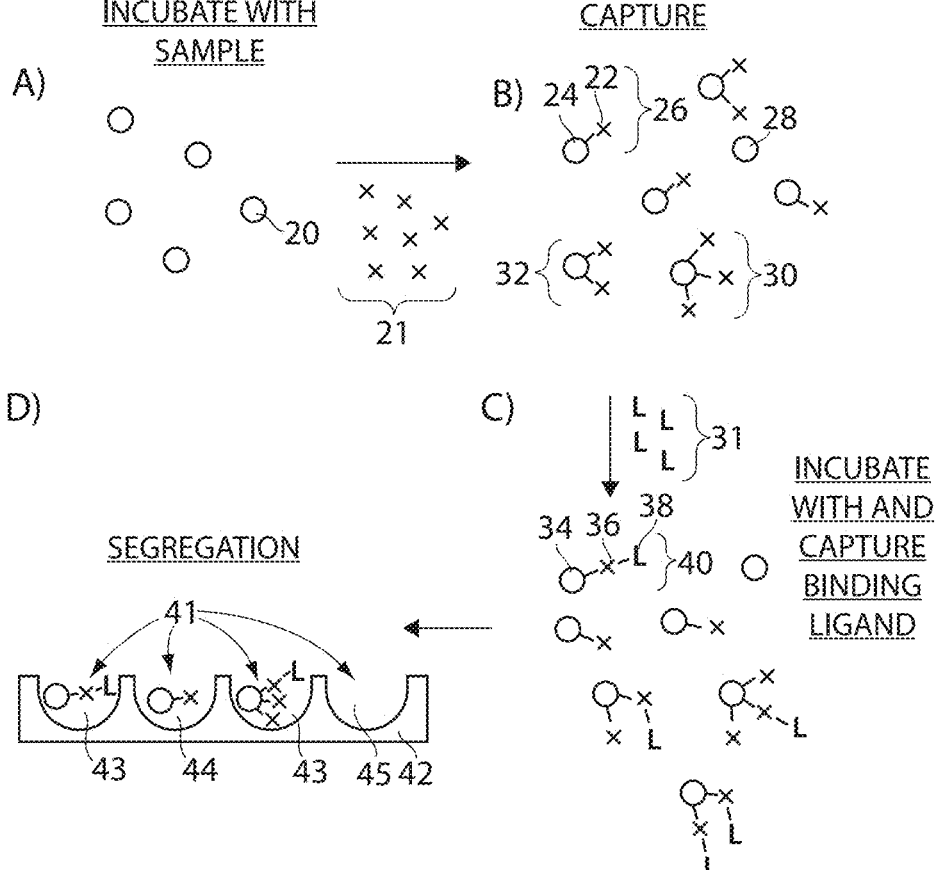
FIG. 1b is a schematic flow diagram depicting one embodiment of steps (A-D) for performing an exemplary method of the present invention.

A non-limiting example of an embodiment where a capture object is associated with more than one biomarker molecule is illustrated in FIG. 1b. A plurality of capture objects 20 are provided (step (A)). In this example, the plurality of capture objects comprises a plurality of beads. The plurality of beads is exposed to a fluid sample containing plurality of biomarker molecules 21 (e.g., beads 20 are incubated with biomarker molecules 21). At least some of the biomarker molecules are immobilized with respect to a bead. For example, as shown in step (B), biomarker molecule 22 is immobilized with respect to bead 24, thereby forming complex 26. Also illustrated is complex 30 comprising a bead immobilized with respect to three biomarker molecules and complex 32 comprising a bead immobilized with respect to two biomarker molecules. Additionally, in some cases, some of the beads may not associate with any biomarker molecules (e.g., bead 28). The plurality of beads from step (B) is exposed to a plurality of binding ligands 31. As shown in step (C), a binding ligand associates with some of the biomarker molecules immobilized with respect to a bead. For example, complex 40 comprises bead 34, biomarker molecule 36, and binding ligand 38. The binding ligands are provided in a manner such that a statistically significant fraction of the beads comprising at least one biomarker molecule become associated with at least one binding ligand (e.g., one, two, three, etc.) and a statistically significant fraction of the beads comprising at least one biomarker molecule do not become associated with any binding ligands. At least a portion of the plurality of beads from step (C) are then spatially separated into a plurality of locations. As shown in step (D), in this example, the locations comprise a plurality of reaction vessels 41 on a substrate 42. The plurality of reaction vessels may be exposed to the plurality of beads from step (C) such at each reaction vessel contains zero or one beads. The substrate may then be analyzed to determine the number of reaction vessels containing a binding ligand (e.g., reaction vessels 43), wherein in the number may be related to a measure of the concentration of biomarker molecules in the fluid sample. In some cases, the number of reaction vessels containing a bead and not containing a binding ligand (e.g., reaction vessel 44), the number of reaction vessels not containing a bead (e.g., reaction vessel 45), and/or the total number of reaction vessels addressed/analyzed may also be determined. Such determination(s) may then be used to determine a measure of the concentration of biomarker molecules in the fluid sample.

In some embodiments, a plurality of locations may be addressed and/or a plurality of capture objects and/or species/molecules/particles of interest may be detected substantially simultaneously. "Substantially simultaneously" when used in this context, refers to addressing/detection of the locations/capture objects/species/molecules/particles of interest at approximately the same time such that the time periods during which at least two locations/capture objects/species/molecules/particles of interest are addressed/detected overlap, as opposed to being sequentially addressed/detected, where they would not. Simultaneous addressing/detection can be accomplished by using various techniques, including optical techniques (e.g., CCD detector). Spatially segregating capture objects/species/molecules/particles into a plurality of discrete, resolvable locations, according to some embodiments facilitates substantially simultaneous detection by allowing multiple locations to be addressed substantially simultaneously. For example, for embodiments where individual species/molecules/particles are associated with capture objects that are spatially segregated with respect to the other capture objects into a plurality of discrete, separately resolvable locations during detection, substantially simultaneously addressing the plurality of discrete, separately resolvable locations permits individual capture objects, and thus individual species/molecules/particles (e.g., biomarker molecules) to be resolved. For example, in certain embodiments, individual molecules/particles of a plurality of molecules/particles are partitioned across a plurality of reaction vessels such that each reaction vessel contains zero or only one species/molecule/particle. In some cases, at least about 80%, at least about 85%, at least about 90%, at least about 95%, at least about 96%, at least about 97%, at least about 98%, at least about 99%, at least about 99.5% of all species/molecules/particles are spatially separated with respect to other species/molecules/particles during detection. A plurality of species/molecules/particles may be detected substantially simultaneously within a time period of less than about 1 second, less than about 500 milliseconds, less than about 100 milliseconds, less than about 50 milliseconds, less than about 10 milliseconds, less than about 1 millisecond, less than about 500 microseconds, less than about 100 microseconds, less than about 50 microseconds, less than about 10 microseconds, less than about 1 microsecond, less than about 0.5 microseconds, less than about 0.1 microseconds, or less than about 0.01 microseconds, less than about 0.001 microseconds, or less. In some embodiments, the plurality of species/molecules/particles may be detected substantially simultaneously within a time period of between about 100 microseconds and about 0.001 microseconds, between about 10 microseconds and about 0.01 microseconds, or less.

In some embodiments, the locations are optically interrogated. The locations exhibiting changes in their optical signature may be identified by a conventional optical train and optical detection system. Depending on the detected species (e.g., type of fluorescence entity, etc.) and the operative wavelengths, optical filters designed for a particular wavelength may be employed for optical interrogation of the locations. In embodiments where optical interrogation is used, the system may comprise more than one light source and/or a plurality of filters to adjust the wavelength and/or intensity of the light source. In some embodiments, the optical signal from a plurality of locations is captured using a CCD camera.

In some embodiments of the present invention, the plurality of reaction vessels may be sealed (e.g., after the introduction of the biomarker molecules, binding ligands, and/or precursor labeling agent), for example, through the mating of the second substrate and a sealing component. The sealing of the reaction vessels may be such that the contents of each reaction vessel cannot escape the reaction vessel during the remainder of the assay. In some cases, the reaction vessels may be sealed after the addition of the biomarker molecules and, optionally, at least one type of precursor labeling agent to facilitate detection of the biomarker molecules. For embodiments employing precursor labeling agents, by sealing the contents in some or each reaction vessel, a reaction to produce the detectable labeling agents can proceed within the sealed reaction vessels, thereby producing a detectable amount of labeling agents that is retained in the reaction vessel for detection purposes.

The plurality of locations may be formed using a variety of methods and/or materials. In some embodiments, the plurality of locations comprises a plurality of reaction vessels/wells on a substrate. In some cases, the plurality of reaction vessels is formed as an array of depressions on a first surface. In other cases, however, the plurality of reaction vessels may be formed by mating a sealing component comprising a plurality of depressions with a substrate that may either have a featureless surface or include depressions aligned with those on the sealing component. Any of the device components, for example, the substrate or sealing component, may be fabricated from a compliant material, e.g., an elastomeric polymer material, to aid in sealing. The surfaces may be or made to be hydrophobic or contain hydrophobic regions to minimize leakage of aqueous samples from the microwells. The reactions vessels, in certain embodiments, may be configured to receive and contain only a single capture object.

In some embodiments, the reaction vessels may all have approximately the same volume. In other embodiments, the reaction vessels may have differing volumes. The volume of each individual reaction vessel may be selected to be appropriate to facilitate any particular assay protocol. For example, in one set of embodiments where it is desirable to limit the number of capture objects used for biomarker capture contained in each vessel to a small number, the volume of the reaction vessels may range from attoliters or smaller to nanoliters or larger depending upon the nature of the capture objects, the detection technique and equipment employed, the number and density of the wells on the substrate and the expected concentration of capture objects in the fluid applied to the substrate containing the wells. In one embodiment, the size of the reaction vessel may be selected such only a single capture object used for biomarker capture can be fully contained within the reaction vessel (see, for example, U.S. patent application Ser. No. 12/731, 130, filed Mar. 24, 2010, published as US-2011-0212848 on Sep. 1, 2011, entitled "ULTRA-SENSITIVE DETECTION OF MOLECULES OR PARTICLES USING BEADS OR OTHER CAPTURE OBJECTS," by Duffy et al.; International Patent Application No. PCT/US2011/026645, filed Mar. 1, 2011, published as WO 2011/109364 on Sep. 9, 2011, entitled "ULTRA-SENSITIVE DETECTION OF MOLECULES OR PARTICLES USING BEADS OR OTHER CAPTURE OBJECTS," by Duffy et al., each herein incorporated by reference).

In some embodiments, the reaction vessels may have a volume between about 1 femtoliter and about 1 picoliter, between about 1 femtoliters and about 100 femtoliters, between about 10 attoliters and about 100 picoliters, between about 1 picoliter and about 100 picoliters, between about 1 femtoliter and about 1 picoliter, or between about 30 femtoliters and about 60 femtoliters. In some cases, the reaction vessels have a volume of less than about 1 picoliter, less than about 500 femtoliters, less than about 100 femtoliters, less than about 50 femtoliters, or less than about 1 femtoliter. In some cases, the reaction vessels have a volume of about 10 femtoliters, about 20 femtoliters, about 30 femtoliters, about 40 femtoliters, about 50 femtoliters, about 60 femtoliters, about 70 femtoliters, about 80 femtoliters, about 90 femtoliters, or about 100 femtoliters.

The total number of locations and/or density of the locations employed in an assay (e.g., the number/density of reaction vessels in an array) can depend on the composition and end use of the array. For example, the number of reaction vessels employed may depend on the number of types of biomarker molecule and/or binding ligand employed, the suspected concentration range of the assay, the method of detection, the size of the capture objects, the type of detection entity (e.g., free labeling agent in solution, precipitating labeling agent, etc.). Arrays containing from about 2 to many billions of reaction vessels (or total number of reaction vessels) can be made by utilizing a variety of techniques and materials. Increasing the number of reaction vessels in the array can be used to increase the dynamic range of an assay or to allow multiple samples or multiple types of biomarker molecules to be assayed in parallel. The array may comprise between one thousand and one million reaction vessels per sample to be analyzed. In some cases, the array comprises greater than one million reaction vessels. In some embodiments, the array comprises between about 1,000 and about 50,000, between about 1,000 and about 1,000,000, between about 1,000 and about 10,000, between about 10,000 and about 100,000, between about 100,000 and about 1,000,000, between about 100,000 and about 500,000, between about 1,000 and about 100,000, between about 50,000 and about 100,000, between about 20,000 and about 80,000, between about 30,000 and about 70,000, between about 40,000 and about 60,000 reaction vessels. In some embodiments, the array comprises about 10,000, about 20,000, about 50,000, about 100,000, about 150,000, about 200,000, about 300,000, about 500,000, about 1,000,000, or more, reaction vessels.

The array of reaction vessels may be arranged on a substantially planar surface or in a non-planar three-dimensional arrangement. The reaction vessels may be arrayed in a regular pattern or may be randomly distributed. In a specific embodiment, the array is a regular pattern of sites on a substantially planar surface permitting the sites to be addressed in the X-Y coordinate plane.

In some embodiments, the reaction vessels are formed in a solid material. As will be appreciated by those in the art, the number of potentially suitable materials in which the reaction vessels can be formed is very large, and includes, but is not limited to, glass (including modified and/or functionalized glass), plastics (including acrylics, polystyrene and copolymers of styrene and other materials, polypropylene, polyethylene, polybutylene, polyurethanes, cyclic olefin copolymer (COC), cyclic olefin polymer (COP), Teflon®, polysaccharides, nylon or nitrocellulose, etc.), elastomers (such as poly(dimethyl siloxane) and poly urethanes), composite materials, ceramics, silica or silica-based materials (including silicon and modified silicon), carbon, metals, optical fiber bundles, or the like. In general, the substrate material may be selected to allow for optical detection without appreciable autofluorescence. In certain embodiments, the reaction vessels may be formed in a flexible material.

A reaction vessel in a surface (e.g., substrate or sealing component) may be formed using a variety of techniques known in the art, including, but not limited to, photolithography, stamping techniques, molding techniques, etching techniques, or the like. As will be appreciated by those of the ordinary skill in the art, the technique used can depend on the composition and shape of the supporting material and the size and number of reaction vessels.

In a particular embodiment, an array of reaction vessels is formed by creating microwells on one end of a fiber optic bundle and utilizing a planar compliant surface as a sealing component. In certain such embodiments, an array of reaction vessels in the end of a fiber optic bundle may be formed as follows. First, an array of microwells is etched into the end of a polished fiber optic bundle. Techniques and materials for forming and etching a fiber optic bundle are known to those of ordinary skill in the art. For example, the diameter of the optical fibers, the presence, size and composition of core and cladding regions of the fiber, and the depth and specificity of the etch may be varied by the etching technique chosen so that microwells of the desired volume may be formed. In certain embodiments, the etching process creates microwells by preferentially etching the core material of the individual glass fibers in the bundle such that each well is approximately aligned with a single fiber and isolated from adjacent wells by the cladding material. Potential advantages of the fiber optic array format is that it can produce thousands to millions of reaction vessels without complicated microfabrication procedures and that it can provide the ability to observe and optically address many reaction vessels simultaneously.

Each microwell may be aligned with an optical fiber in the bundle so that the fiber optic bundle can carry both excitation and emission light to and from the wells, enabling remote interrogation of the well contents. Further, an array of optical fibers may provide the capability for simultaneous or non-simultaneous excitation of molecules in adjacent vessels, without signal "cross-talk" between fibers. That is, excitation light transmitted in one fiber does not escape to a neighboring fiber.

Alternatively, the equivalent structures of a plurality of reaction vessels may be fabricated using other methods and materials that do not utilize the ends of an optical fiber bundle as a substrate. For example, the array may be a spotted, printed or photolithographically fabricated substrate produced by techniques known in the art; see for example WO95/25116; WO95/35505; PCT US98/09163; U.S. Pat. Nos. 5,700,637, 5,807,522, 5,445,934, 6,406,845, and 6,482,593. In some cases, the array may be produced using molding, embossing, and/or etching techniques as will be known to those of ordinary skill in the art.

In some embodiments, the plurality of locations may not comprise a plurality of reaction vessels/wells. For example, in embodiments where capture objects are employed, a patterned substantially planar surface may be employed and the patterned areas form a plurality of locations. In some cases, the patterned areas may comprise substantially hydrophilic surfaces which are substantially surrounded by substantially hydrophobic surfaces. In certain embodiments, a plurality of capture objects (e.g., beads) may be substantially surrounded by a substantially hydrophilic medium (e.g., comprising water), and the beads may be exposed to the patterned surface such that the beads associate in the patterned areas (e.g., the hydrophilic locations on the surface), thereby spatially segregating the plurality of beads. For example, in one such embodiment, a substrate may be or include a gel or other material able to provide a sufficient barrier to mass transport (e.g., convective and/or diffusional barrier) to prevent capture objects used for biomarker capture and/or precursor labeling agent and/or labeling agent from moving from one location on or in the material to another location so as to cause interference or cross-talk between spatial locations containing different capture objects during the time frame required to address the locations and complete the assay. For example, in one embodiment, a plurality of capture objects is spatially separated by dispersing the capture objects on and/or in a hydrogel material. In some cases, a precursor labeling agent may be already present in the hydrogel, thereby facilitating development of a local concentration of the labeling agent (e.g., upon exposure to a binding ligand or biomarker molecule carrying an enzymatic component). As still yet another embodiment, the capture objects may be confined in one or more capillaries. In some cases, the plurality of capture objects may be absorbed or localized on a porous or fibrous substrate, for example, filter paper. In some embodiments, the capture objects may be spatially segregated on a uniform surface (e.g., a planar surface), and the capture objects may be detected using precursor labeling agents which are converted to substantially insoluble or precipitating labeling agents that remain localized at or near the location of where the corresponding capture object is localized. The use of such substantially insoluble or precipitating labeling agents is described herein. In some cases, single biomarker molecules may be spatially segregated into a plurality of droplets. That is, single biomarker molecules may be substantially contained in a droplet containing a first fluid. The droplet may be substantially surrounded by a second fluid, wherein the second fluid is substantially immiscible with the first fluid.

Figure 5A:
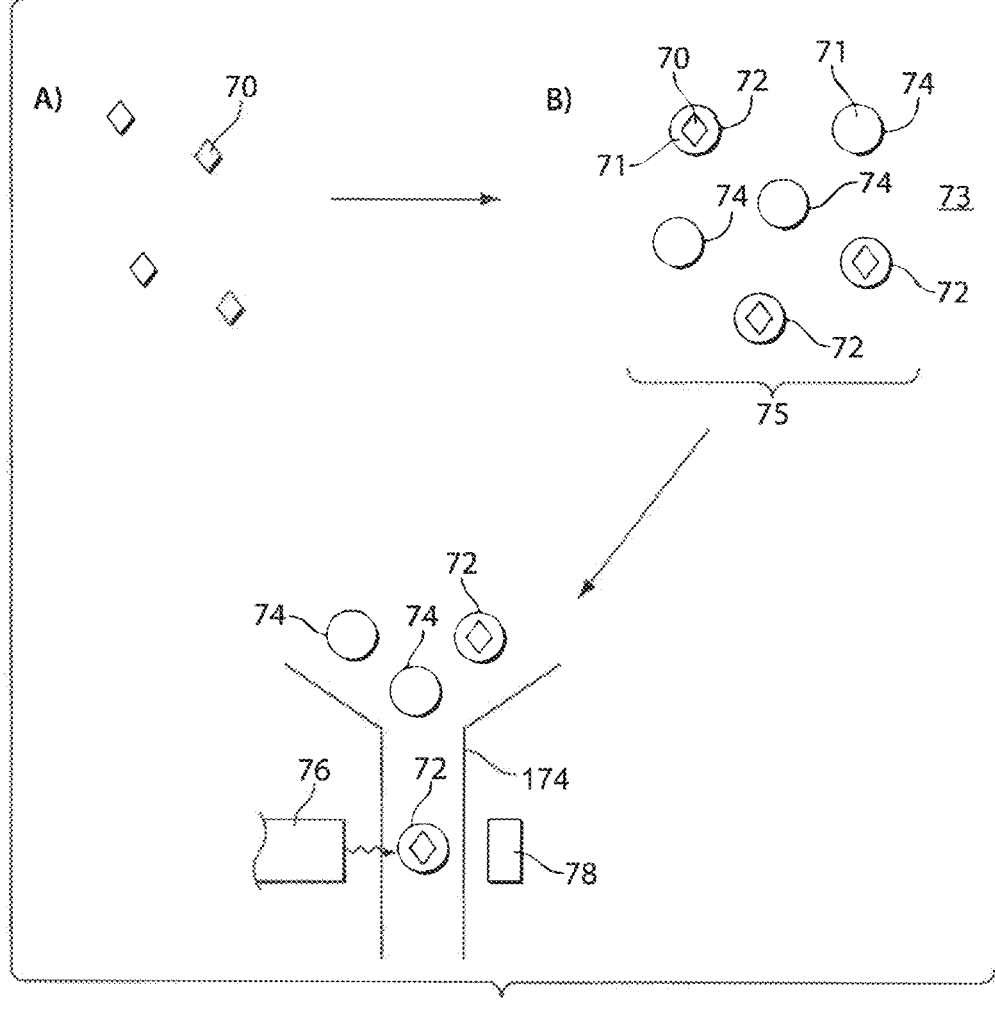
FIG. 5A is a schematic flow diagram depicting one embodiment of steps (A-C) for performing an exemplary method of the present invention.

FIG. 5A illustrates a non-limiting embodiment where single analyte molecules are spatially segregating into a plurality of droplets. In FIG. 5A, plurality of analyte molecules 70 are provided, as shown in step (A). In this example, analyte molecules 70 are capable of being optically detected (e.g., the analyte molecules may be directly detected using optical interrogation). At least some of the plurality of analyte molecules 70 are contained within liquid droplets 72 (e.g., using microfluidic techniques) which comprise fluid 71, as shown in step (B). Additionally, some droplets may be present which do not contain any analyte molecules (e.g., droplets 74 comprising fluid 71). Plurality of droplets 75 are substantially surrounded by fluid 73 which is substantially immiscible with fluid 71. Plurality of droplets 75 can be optically interrogated by feeding droplets into column 174 such that each droplet passes by an optical detection system (e.g., comprising light source 76 and detector 78) single file, as shown in step (C). Each droplet may be determined to contain an analyte molecule when there is a change in the optical signal (e.g., a change in optical signal due to the presence of an analyte molecule in the droplet).

Figure 5B:
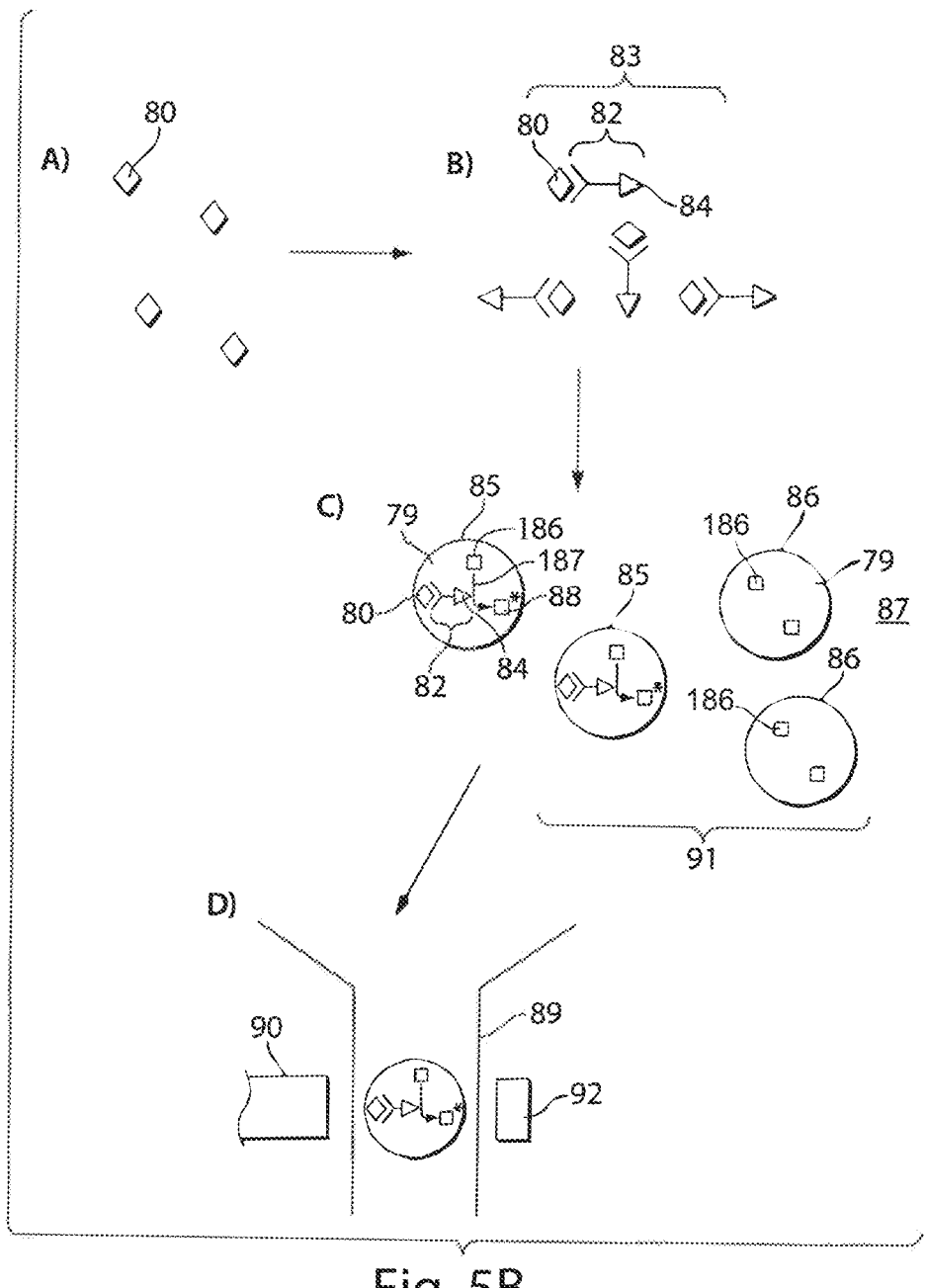
FIG. 5B is a schematic flow diagram depicting one embodiment of steps (A-D) for performing an exemplary method of the present invention.

As another example, as illustrated in FIG. 5B, plurality of analyte molecules 80 are provided, as shown in step (A). In this example, analyte molecules 80 are not capable of being optically detected, and must be indirectly detection (as described herein). Plurality of analyte molecules 80 are exposed to a plurality of binding ligands 82, such that at least one binding ligand associates with a significant portion of the analyte molecules, as shown in step (B), to form complex 83, as shown in step (B). In this example, each binding ligand 82 comprises enzymatic component 84. At least a portion of complexes 83 may be contained in droplets 85 (e.g., using microfluidic techniques), as shown in step (C), which comprise liquid 79. Additionally, some droplets may be present which do not contain any complexes (e.g., droplets 86 comprising fluid 79). Plurality of droplets 91 are substantially surrounded by fluid 87 which is substantially immiscible with fluid 79. Droplets 85 and 86 may additionally comprise precursor labeling agent 186, which is converted to labeling agent 88 upon exposure to enzymatic component 84, as indicated by arrow 187. Plurality of droplets 91 can be optically interrogated by feeding the plurality of droplets into column 89 such that each droplet passes by an optical detection system (e.g., comprising light source 90 and detector 92) single file, as shown in step (D). Each droplet may be determined to contain an analyte molecule when there is a change in the optical signal (e.g., a change in optical signal due to the presence of a labeling agent in the droplet).

Figure 5C:
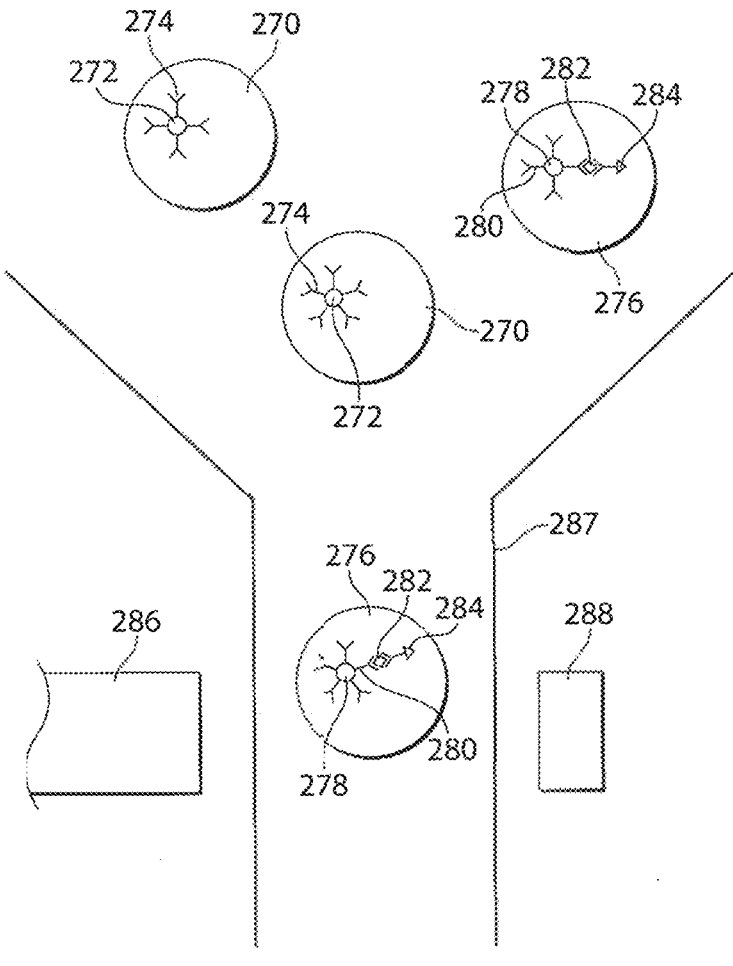
FIG. 5C is a schematic diagram depicting one embodiment for performing an exemplary method of the present invention.

As yet another example, FIG. 5C illustrates an embodiment where single analyte molecules 282 are associated with respect to capture objects 272, 278 via capture components 274. Additionally, in this example, the immobilized analyte molecules are associated with binding ligand 284. The droplets can be optically interrogated by feeding droplets into column 287 such that each droplet passed by the optical detection system (e.g., comprising light source 286 and detector 288) single file. Each droplet may be determined to contain a binding ligand when there is a change in the optical signal (e.g., a change in optical signal due to the presence of a binding ligand in the droplet).

In some embodiments, during the assay, at least one washing step may be carried out. In certain embodiments, the wash solution is selected so that it does not cause appreciable change to the configuration of the capture objects and/or biomarker molecules and/or does not disrupt any specific binding interaction between at least two components of the assay (e.g., a capture component and a biomarker molecule). In other cases, the wash solution may be a solution that is selected to chemically interact with one or more assay components. As will be understood by those of ordinary skill in the art, a wash step may be performed at any appropriate time point during the inventive methods. For example, a plurality of capture objects may be washed after exposing the capture objects to one or more solutions comprising biomarker molecules, binding ligands, precursor labeling agents, or the like. As another example, following immobilization of the biomarker molecules with respect to a plurality of capture objects, the plurality of capture objects may be subjected to a washing step thereby removing any biomarker molecules not specifically immobilized with respect to a capture object.

Other assay methods in addition to those described herein are known in the art and may be used in connection with the inventive methods. For example, various analyzers are commercially available for the determination of the concentration of biomarkers. The assay methods employed should meet the algorithm requirements for LOD and LOQ.

The following examples are included to demonstrate various features of the invention. Those of ordinary skill in the art should, in light of the present disclosure, will appreciate that many changes can be made in the specific embodiments which are disclosed while still obtaining a like or similar result without departing from the scope of the invention as defined by the appended claims. Accordingly, the following examples are intended only to illustrate certain features of the present invention, but do not necessarily exemplify the full scope of the invention.

Example 1

The following example provides experimental details relating to prognostication of neurological outcome in comatose survivors of oxygen deprivation, using tau proteins Objective: Use of peripheral tau protein measurements as an indicator of the presence of brain injury has remained elusive, in large part due to the lack of adequate sensitivity for reliable measurement of the protein in serum or plasma using common technologies. Additionally, little was known about the time-dependence of tau protein release from the central nervous system into peripheral circulation. Using methods described herein, which, in certain embodiments are capable of ultra sensitive tau protein measurement, serial serum samples from 25 resuscitated cardiac arrest patients were analyzed to longitudinally study tau protein release into serum and determine prognostic significance of tau protein elevation for prediction of long-term cognitive impairment from hypoxic insult.

Summary of Methods: 25 unconscious patients with cardiac arrest were resuscitated with restoration of spontaneous circulation and admitted to a hospital intensive care unit (ICU). Patients were treated with hypothermia and repeated blood samplings were obtained during the first five days in the ICU. Serum levels of total tau protein were measured with a digital immunoassay described in Example 2. Cognitive assessments were made using Cerebral Performance Categorization (CPC) at discharge from the ICU and six months later. Tau protein data were analyzed in the context of six-month cognitive outcome.

Summary of Results: Tau protein elevations ranged from modest to very high, and exhibited unexpected bi-modal kinetic profiles in many patients. Total area-under-the-curve (AUC) was highly prognostic for six-month cognitive outcome. AUC of the secondary tau protein peak exhibited 100% sensitivity and 91% specificity for predicting 6-month outcome.

Summary of Conclusions: The data indicate that sufficiently sensitive peripheral tau protein measurements in conjunction with an understanding of tau protein release kinetics have clinical utility for brain injury assessment and prognostication of cognitive outcome.

Additional Background: Tau proteins, with a molecular mass of 48 to 67 kd depending on isoform, are associated with microtubules and localized in the axonal compartment of neurons. Tau proteins plays a structural role in the assembly of tubulin monomers into axonal microtubule bundles, which are important for maintaining the cytoskeleton and axonal transport. Tau protein is generally elevated in the cerebrospinal fluid (CSF) of patients with neurodegenerative disease and severe head injuries, making it a candidate for peripheral measurement as a biomarker of acquired or traumatic brain injury (ABI, TBI). However, studies on peripheral tau protein have been hampered by its low abundance in serum and plasma (typically low pg/mL), making its measurement difficult.

While CSF tau protein elevation is known to correlate with 1-year outcome in severe TBI patients, no such correlation has been made to serum tau protein, in part because most common assays cannot accurately detect the low levels of tau protein in serum. In addition, the clinical value of serum tau protein for assessment of minor head injury has been questioned. A previous study looked at serum tau protein elevation measured in 24 ischemic stroke patients studied using an immunoassay with a limit of detection of 60 pg/mL, but no correlation was made or found between tau protein appearance to stroke severity. A recent rat TBI model indicated serum tau protein elevation peaked rapidly and declined after six hours, with no significant additional tau protein elevation over 7 days. Little else has been reported about the kinetics of tau protein movement across the blood brain barrier (BBB), nor the potential prognostic significance of peripheral tau protein appearance with ABI or TBI.

Methods: This example employed the protocol described in Example 2 below, which is capable in certain embodiments of three logs greater sensitivity than typical conventional methods. The assay was utilized to examine serial serum samples from 25 resuscitated cardiac arrest patients to longitudinally study tau protein release into serum and probe for prognostic significance of tau protein elevation for prediction of long-term cognitive impairment due to hypoxic insult.

The study was performed at the general intensive care unit at Uppsala University Hospital, Sweden, and approved by the Human Ethics Committee of Uppsala. Sweden. Twenty-five unconscious patients with cardiac arrest were resuscitated with restoration of spontaneous circulation (ROSC). Patients were >18 yrs old, exhibited systolic blood pressure >80 mmHg after ROSC, and a Glasgow Coma Scale ≤7.

Upon admission, hypothermia treatment was started immediately after resuscitation. Ventilation was administered during the coma period, with a target $PaO_2$ of ≥12 kPa (90 mmHg) and $PaCO_2$ between 5.0 and 5.5 kPa (38-41 mmHg). Targeted mean arterial pressure was 65-100 mmHg, with application of inotropic/vasopressor support, if required, using dobutamine as the first line medication, followed by noradrenaline (norepinephrine) or adrenaline (epinephrine), if necessary. If the patient was considered euvolaemic but had a diuresis of less than 0.5 ml/kg/h, furosemide was administered. Furosemide was also given if the intensive care physician considered that the patient had a fluid overload. All patients received an arterial line in the radial or femoral artery for blood sampling. Serial blood samples were collected, starting as soon as possible in the emergency phase (within 6 h after cardiac arrest), and continuing at 1, 2, 6, 12, 24, 48, 72, 96, and 108 h after cardiac arrest. Serum aliquots were frozen at −70° C. until analysis.

Patient outcome was assessed in accordance with the Glasgow-Pittsburgh cerebral performance category (CPC) scale at discharge from the intensive care unit and 6 months later. The CPC scale ranges from 1 to 5, with 1 representing mildest possible neurological deficit (patient is able to return to work), and 4-5 representing the most severe deficit (vegetative) and death. A CPC of 1 or 2 was considered a "good" outcome and a CPC score of 3-5 a "poor" outcome. For patients who died after ICU discharge, the better of the two scores was used, as recommended by the Utstein templates.

Patient serum samples were measured in triplicate by a single molecule digital immunoassay for tau protein (see Example 2 for more details). The technique involves performing a paramagnetic bead-based ELISA using beta-galactosidase as a reporter, followed by isolation of individual capture beads within femtoliter-sized reaction wells in a microarray. Isolation of individual beads permits the buildup of fluorescent substrate in the presence of tau protein, such that wells containing a single immunocomplex can be detected. The limit of detection of the assay is 0.02 pg/mL, making it approximately 1000-fold more sensitive than typical conventional immunoassays. The assay was calibrated from 0 pg/mL to 100 pg/mL total tau protein and was able to precisely measure serum tau protein in the patient samples. The extreme sensitivity of the method permits pre-dilution of the samples prior to assay, reducing potential endogenous interferences. All samples were pre-diluted 1:4 with a PBS-tween diluent prior to assay.

Tau protein elevation profiles were analyzed for area-under-the-curve (AUC) with the graphing and statistics software GraphPad Prism™ 5.0d (GraphPad Software, La Jolla, CA). Four of the 25 patients died 24-48 hours after admission, and these patients were excluded from AUC analysis. AUC was evaluated during the first 24-hour period as well as over the full time course of samples (to 108 hours) using a baseline of zero. In addition, the AUC of secondary tau protein elevation peaks were estimated assuming a baseline corresponding to the tau protein concentration measured at the initial time point of the secondary peak. Statistical significance between 'good' and 'poor' 6-month outcome was determined by student t-test, with significance taken as $p<0.05$.

Figure 2:
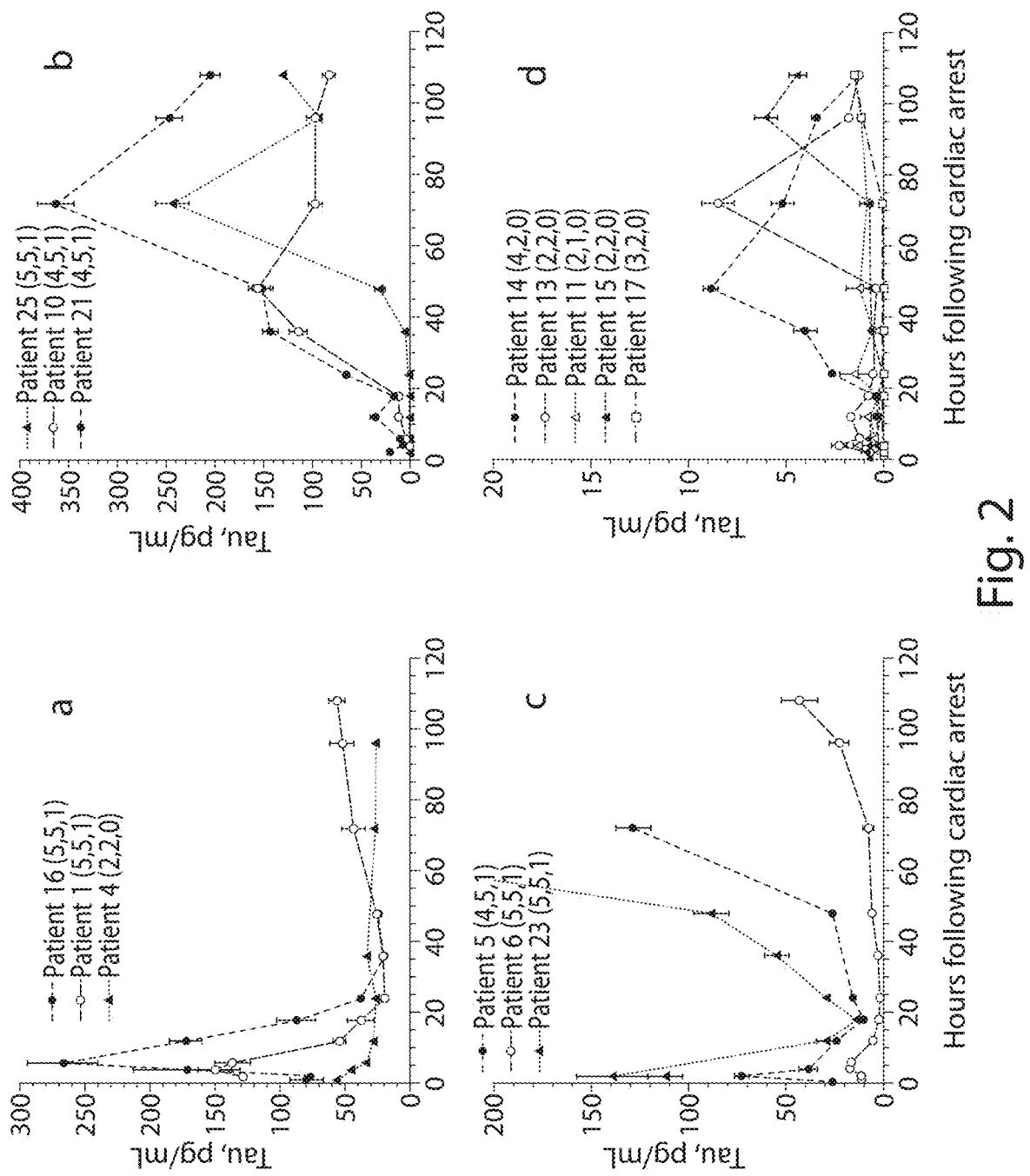
FIG. 2 show plots of serum tau concentrations for numerous patients following resuscitation from cardiac arrest having a-c) a poor outcome and d) a good outcome.

Results: Representative elevation profiles for patients with good and poor 6-month outcomes are depicted in FIG. 2. FIG. 2 shows serum tau following resuscitation from cardiac arrest. CPC scores are listing for each patient in the legends. The first two numbers correspond to the CPC assessments upon discharge from the ICU and six months later. The third number represents overall 6-month outcome assessment (1=poor, 0=good). FIGS. 2a-2c depict representative groupings of patients exhibiting different profiles of tau elevations: a) initial 24-hour peaks; b) delayed peaks, and c) both initial 24-hour and delayed peaks. FIG. 2d depicts representative profiles from patients with good outcomes. Note the difference in scales. Error bars depict SD of triplicate measurements.

Tau protein expression ranged from almost undetectable to large elevations approaching 700 pg/mL. There was a strong general association between tau protein elevation and patient outcome: the more tau protein expressed, the greater the likelihood for poor 6-month outcome. Tau protein elevation also showed clear bi-modal tendencies, with the appearance of one or both peaks varying with patient. The initial peak was generally fully expressed during the first 24 hours following cardiac arrest, while the secondary peak generally expressed after 24-48 hours. Some patients exhibited only the first peak (FIG. 2a), some exhibited only the second peak (FIG. 2b), and some exhibited both peaks (FIG. 2c).

TABLE 2

| Patient | AUC ≤ 24 hr Good | AUC ≤ 24 hr Poor | AUC all Good | AUC all Poor | AUC 2nd peak only Good | AUC 2nd peak only Poor |
|---|---|---|---|---|---|---|
| 2 | | 1590 | | 4759 | | 1440 |
| 3 | 708.9 | | 2145 | | 0 | |
| 4 | 748.3 | | 2861 | | 154.2 | |
| 5 | | 625.2 | | 3007 | | 1890 |
| 6 | | 179.9 | | 1232 | | 897.5 |
| 7 | 4.72 | | 92.86 | | 54.5 | |
| 8 | | 11.19 | | 1646 | | 1545 |

TABLE 2-continued

| Patient | AUC ≤ 24 hr Good | AUC ≤ 24 hr Poor | AUC all Good | AUC all Poor | AUC 2nd peak only Good | AUC 2nd peak only Poor |
|---|---|---|---|---|---|---|
| 9 | 59 | | 1141 | | 0 | |
| 10 | | 109.7 | | 9336 | | 8206 |
| 11 | 14.63 | | 84.56 | | 0 | |
| 12 | | 52.15 | | 848.2 | | 567.8 |
| 13 | 26.01 | | 288.5 | | 215.8 | |
| 14 | 12.93 | | 431.5 | | 393 | |
| 15 | 12.31 | | 184.4 | | 168.2 | |
| 17 | 0.02 | | 30.68 | | 30.9 | |
| 18 | 15.78 | | 46.62 | | 0 | |
| 20 | | 334.6 | | 6827 | | 5511 |
| 21 | | 580.8 | | 19875 | | 18051 |
| 23 | | 1039 | | 26150 | | 23935 |
| 24 | | 12.92 | | 72.9 | | 35.94 |
| 25 | | 9.37 | | 8987 | | 8842 |
| AVG | 160.26 | 413.17 | 730.61 | 7521.83 | 101.66 | 6447.39 |
| t-test (p) | 0.090609467 | | 0.011726946 | | 0.01197362 | |

Figure 3:
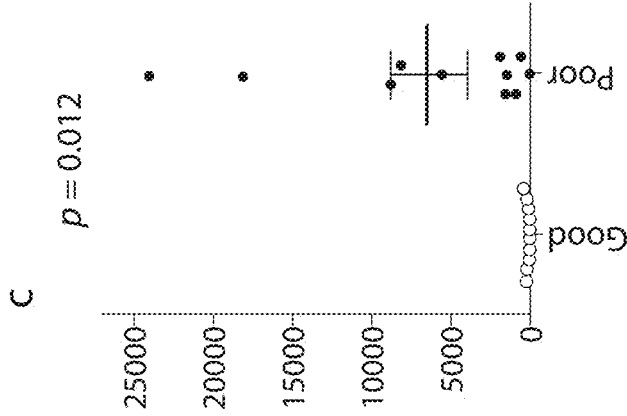
FIG. 3 shows plots of receiver operating characteristics (ROC) curves and areas under the curve values of tau protein concentration versus time for a) the first 24 hours, b) all serial samplings, and c) the secondary tau peak only.
Figure 3:
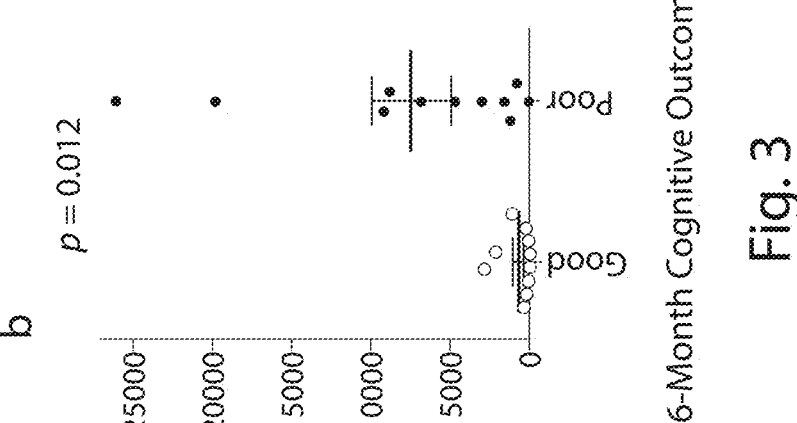
Figure 3:
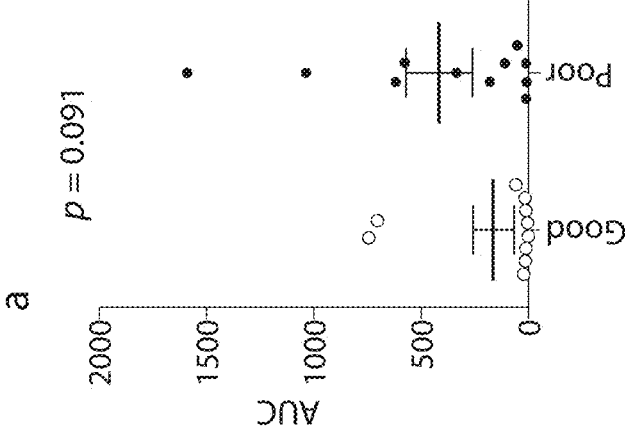

To compare the significance of the primary and secondary elevation profiles for 6-month outcome, AUCs were calculated for the first 24 hours (referred to as the "first peak"), the full time course, and the secondary peak only. Table 2 exhibits AUCs for each patient, which are plotted in FIG. 3. More specifically, Table 2 tabulates characteristics of serum tau elevation profiles from resuscitated survivors of cardiac arrest during the first 96-108 hours following admission to the ICD. Parameters were sorted on the basis of good or poor 6-month cerebral outcome and compared by student t-test. Four patients (all with good outcome) exhibited no discernable secondary peaks. FIG. 3 plots AUC results a) across the first 24 hours, b) for all serial samplings, and c) the secondary tau peak only. Error bars depict standard error of the means.

Weak correlation was observed between the initial 24 hours and 6-month outcome ($p>0.05$). Notably, there was a strong correlation between the secondary peak and 6-month outcome ($p=0.01$). The weak correlation between initial tau protein appearance and outcome reflects inter-patient differences in primary peak expression rather than lack of significance between tau protein elevation and outcome. Calculation of overall AUC gave similar statistical significance with outcome as the AUC of the second peak only. Patients with good outcome generally had very low serum tau protein, and secondary peaks where either absent or weak (FIG. 2d).

The appearance and magnitude of the secondary tau protein peak was highly prognostic for 6-month outcome. Bifurcating the data with an AUC cut point of 500 resulted in 100% sensitivity (10/10 patients) and 91% specificity (10/11 patients) for predicting good and poor 6-month outcomes respectively.

Discussion: These data represent a high-resolution longitudinal examination of serum tau protein elevation following an acute ABI event. The bimodal profile elevation kinetics are consistent with two modes of neuronal damage: initially upon acute oxygen deprivation, followed by delayed cell death due to apoptosis and/or cerebral swelling. With ROSC as an inclusion criterion, the elevation kinetics should be unrelated to reperfusion differences between patients. Patients were all treated with hypothermia, and were not treated with drugs known to significantly affect BBB permeability. It seems likely the bimodal profiles are related to neuronal damage rather than BBB or reperfusion variables.

Inter-patient differences in expression one or both elevation peaks could be related to the extent and duration of the hypoxia. Global cerebral ischemia could trigger rapid necrosis in addition to longer-term apoptosis cascades. Sub lethal hypoxic encephalopathy can set a series of toxic reactions in motion that finish off injured neurons and kill additional ones over hours or days following the insult. While early tau protein peaks were less prognostics for 6-month outcome than the secondary elevation, they are nonetheless deadly when high levels of tau protein are measured. Among the four patients who did not survive the first 48 hours, two patients had prominent initial tau protein peaks of well over 200 pg/mL that had dropped 10-fold by 24 hours (not shown). In these patients, it may have been that the acute initial necrosis was sufficiently lethal, and it might be anticipated that survival would have witnessed prominent secondary peaks.

It is noted that the serial sampling in this study was concluded at 108 hours. It may be that additional tau protein elevation occurs beyond 108 hours. Studies of tau protein elevation in CSF following severe TBI have revealed temporal elevations well beyond five days. It is possible that patients in the present study exhibiting tau protein peaks in the first 24 hours with minimal secondary elevation could go on to express significant additional tau protein beyond 108 hours.

Since the magnitude of cognitive impairment should reflect the magnitude of hypoxia, correlation of serum tau protein elevation with cognitive outcome indicates released tau protein reflects the extent of hypoxia and associated neuronal damage. Serum tau protein appearance as measured by digital immunoassay exhibited considerable prognostic significance for 6-month cognitive outcome, with a sensitivity and specificity of 100% using an AUC cut point of 500. This example demonstrates that serial blood measurements of tau protein in the ICU following resuscitation from cardiac arrest has a clinical value for stratifying likely cognitive outcome.

Example 2

The following example describes the tau protein ultra-sensitive digital immunoassay for plasma tau using single molecule arrays that was employed in Example 1.

Reagents were developed for a paramagnetic bead-based ELISA. Tau protein molecules in plasma were captured on antibody-coated paramagnetic capture beads and labeled with an enzyme conjugate. The beads were loaded into arrays of 50,000, 50-femtoliter reaction wells etched into bundles of optical fibers. Single capture beads trapped in each well were sealed in the presence of enzyme substrate and imaged using a fluorescence microscope fitted with a CCD camera. At low concentrations, the images were analyzed for the presence or absence of single immunocomplexes of labeled tau protein, resulting in a digital signal. At high concentrations, the analog intensity of the beads was normalized to the digital signals, extending the dynamic range of the assay to over four logs. Analytical performance of the assay was evaluated, and serum samples from hypoxia patients were tested for tau protein.

The assay described in this example has a detection limit (i.e., LOD) of 0.02 pg/mL and was linear to 100 pg/mL tau protein ($R2>0.996$, Patient I.J cal curve). Results using serum samples from hypoxia patients showed a bi-phasic response across the time course post hypoxic insult.

Concentrations of tau protein in serum and plasma are believed to be over 100-fold lower than in cerebrospinal fluid.

This example describes the development and validation of a digital immunoassay using single molecule array technology that is capable of measuring tau protein in hypoxia induced serum without biomarker enrichment or sample pretreatment procedures. The assay exhibits over 1000-fold greater sensitivity than validated commercially available ELISAs. The assay can be used for directly measuring and monitoring serum tau protein in therapeutic trials aimed at altering and lowering levels of this protein, down to sub-femtomolar levels.

The single molecule array technology employed two primary steps: an initial analyte capture step conducted with paramagnetic beads, followed by isolation of individual beads in arrays of femtoliter-sized reaction wells for digital imaging. Isolation of the individual beads in microwells permits the buildup of fluorescent product from the enzyme label such that signal from a single immunocomplex is readily detected using a CCD camera. This approach permits counting of single molecules when tau protein concentrations are low enough that the ratio of bound labeled peptide per bead is much less than one. In this concentration realm, Poisson statistics predict that bead-containing microwells in the array will contain either a single labeled tau protein molecule or no labeled tau protein molecules, resulting in a binary signal. Due to the amplified sensitivity for detecting label molecules afforded by confining fluorescent product buildup to the microwells, concentrations of label (detector anti-Tau antibody and enzyme label) can be reduced relative to standard ELISAs. Lowered concentrations of labeling reagents reduces their interaction with capture beads, resulting in reduced nonspecific binding enabling high signal to background ratios, even at extremely low concentrations of biomarker. For higher biomarker concentrations where all beads contain one or more labeled immunocomplexes, digital signals from the Poisson realm are used to calibrate analog intensity measurements, extending the dynamic range to over four logs.

Three reagents were developed for this tau protein immunoassay: capture beads, biotinylated detector, and a conjugate of streptavidin:beta-galactosidase. The capture bead reagent comprised of a commercially available monoclonal anti-tau antibody (Covance) directed to an epitope (amino acids 210-230). The antibody was covalently attached by standard coupling chemistry to 2.7 μm carboxy paramagnetic microbeads (Varian). Because individual beads were captured in array wells 4.5 μm wide×3.25 μm deep, it was advantageous that the capture beads remain monomeric. The antibody-coated beads were diluted to a working concentration of 6×106 beads/mL in Tris buffer with a surfactant and BSA. The biotinylated detector reagent was comprised of two commercially available monoclonal anti-tau antibodys (Pierce) directed to the N-terminus of the Capture Detector (amino acids 159-163 and 194-198). The antibodies were biotinylated using standard methods (Solulink), and the biotinylation level was confirmed spectrophotometrically per manufacturer's instructions. The monomeric state of the detector antibody before and after biotinylation was confirmed by size exclusion HPLC. The biotinylated detector antibodies were diluted to individual concentration of 0.2 μg/ml for assay in a PBS diluent containing a surfactant and newborn calf serum, NCS (PBS/NCS). The enzyme conjugate—streptavidin: β-galactosidase (SβG)—was prepared by covalent conjugation of purified streptavidin (Thermo Scientific) and β-galactosidase (Sigma) using standard coupling chemistry (1-ethyl-3-(3-dimethylaminopropyl) carbodiimide hydrochloride. Thermo Scientific). Aliquots of a concentrated stock solution of SβG were prepared in PBS with 50% glycerol and transferred to −20° C. for storage. Prior to assay, an aliquot was thawed and diluted to 25 pM in PBS/NCS with MgCl2. Purified Tau 381 antigen for calibrators and for specificity testing were from Millipore.

Assay calibrators and controls were prepared by dilution of Tau 381 stock in PBS diluent containing a surfactant and BSA (PBS/BSA). In some cases, a stock solution prepared by dilution to 1000 ng/ml in PBS/10G. For dynamic range/ linearity characterization, a series of calibrators were prepared by serial 3-fold dilution to give a calibration range of 0-100 pg/mL. To evaluate assay day-to-day reproducibility at low concentrations, three low controls were prepared at 0.1, 5.0, and 50.0 pg/mL in PBS/BSA.

50,000 well optical fiber microarrays were prepared as previously described. In brief, optical fiber bundles (Schott North America) were cut into 5 cm lengths and sequentially polished with 30, 9, and 1 um-sized diamond lapping films. One end of each bundle was etched in a 0.025 N HCl solution for 2 minutes and then submerged into water. The differential etch rate of the core and cladding glass of the fiber bundles caused an array of 4.5 um diameter wells to be formed in the core fibers.

Bead-plasma incubations and labeling of immunocom- plexes in conical 96 well plates (Axygen) were conducted using a robotic liquid handling system (Tecan EVO 150). Conical wells are used to facilitate magnetic attraction of the beads to the sides of the wells for efficient removal of reaction mixtures and bead washing. For magnetic attrac- tion, a microplate bar magnet (Invitrogen) was used. Incu- bation periods were conducted with shaking on a microplate shaker (VWR) to keep beads suspended in the wells. The assays were initiated by mixing 100 uL of sample with 600.000 capture beads, and the mixtures were incubated with shaking for two hours. Serum samples were pre-diluted 1:4 prior to assay with PBS/BSA as a precaution for sample quality and interference effects. Following serum incubation in the presence of biotinylated detector antibody, the beads were washed 3 times with a wash buffer of 5-fold concen- trated PBS with a surfactant (5×PBS). After a the wash step, 100 μL of streptavidin-β-galactosidase was incubated with the beads for 30 minutes to form the final enzyme-labeled immunocomplex. The beads were then washed eight times per above, and concentrated to $2 \times 10^7$ beads/ml with the addition of a reduced volume (30 μL) of array loading buffer comprised of PBS with a surfactant. Beads were then loaded onto the arrays. 10 μL of the concentrated bead solution ($2 \times 10^6$ beads) were pipetted onto the arrays and the arrays were centrifuged at 1,300 g for 10 minutes. Excess beads were removed by a PBS rinse and swabbing with deionized water. With this technique, array filling by the beads was generally 50-60%, which was adequate for minimizing contributions to imprecision from Poisson noise. Wells containing tau protein-labeled beads were detected utilizing beta-galactosidase catalyzed hydrolysis of resorufin β-D- galactopyranoside (RGP, Invitrogen) into fluorescent prod- uct (resorufin, excitation 558 nm, emission 577 nm). To introduce RGP substrate to the array wells, droplets of substrate were placed on a silicone gasket and introduced into the array wells with a mechanical platform. This step resulted in an array of sealed femtoliter wells in which enzyme-containing beads developed a concentrated fluores- cence signal.

Imaging was accomplished via a custom-built fluores- cence imaging system containing a light source, objectives, filter cubes and a CCD camera. For each sample, five fluorescent images of one second each were acquired (to identify wells containing an enzyme) and one white light image was acquired (to identify wells containing a bead). Background fluorescence and any contaminating artifacts were discriminated from true 'positive' wells by analyzing for signal growth over the multiple images. These images were analyzed to determine the average number of enzymes per bead (AEB) across the concentration range. In some cases, at <50% active beads, the system was determined to be in the digital realm, so AEB was be determined from the fraction of beads that contain at least one enzyme and the Poisson distribution; and at >50% active beads, the average fluorescence intensity of the beads was normalized to the average fluorescence intensity of beads containing a single enzyme to yield AEB. In other cases, at <70% active beads relative to total beads, AEB was determined as a count of active beads corrected for a low statistical probability of multiple enzymes per bead; and at >70% active beads, the probability of multiple enzymes/bead increases such that all wells contain multiple enzymes and all are growing in signal and in this realm, the signal is was no longer digital, and average fluorescence intensities of the wells were converted to AEB based on the average intensities of wells containing single enzymes as determined at lower Aβ42 concentrations. The AEB unit worked continuously across the digital and analog realms.

For description of various details associate with this assay, see, for example, U.S. patent application Ser. No. 12/731, 130, filed Mar. 24, 2010, published as US-2011-0212848 on Sep. 1, 2011, entitled "ULTRA-SENSITIVE DETECTION OF MOLECULES OR PARTICLES USING BEADS OR OTHER CAPTURE OBJECTS," by Duffy et al.; Interna- tional Patent Application No. PCT/US2011/026645, filed Mar. 1, 2011, published as WO 2011/109364 on Sep. 9, 2011, entitled "ULTRA-SENSITIVE DETECTION OF MOLECULES OR PARTICLES USING BEADS OR OTHER CAPTURE OBJECTS," by Duffy et al.; Interna- tional Patent Application No. PCT/US2011/026657, filed Mar. 1, 2011, published as WO 2011/109372 on Sep. 9, 2011, entitled "ULTRA-SENSITIVE DETECTION OF MOLECULES USING DUAL DETECTION METHODS," by Duffy et al.; U.S. patent application Ser. No. 12/731,135, filed Mar. 24, 2010, published as US-2011-0212462 on Sep. 1, 2011, entitled "ULTRA-SENSITIVE DETECTION OF MOLECULES USING DUAL DETECTION METHODS," by Duffy et al.; International Patent Application No. PCT/ US2011/026665, filed Mar. 1, 2011, published as WO 2011/ 109379 on Sep. 9, 2011, entitled "METHODS AND SYS- TEMS FOR EXTENDING DYNAMIC RANGE IN ASSAYS FOR THE DETECTION OF MOLECULES OR PARTICLES," by Rissin et al.; U.S. patent application Ser. No. 12/731,136, filed Mar. 24, 2010, published as US-2011- 0212537 on Sep. 1, 2011, entitled "METHODS AND SYS- TEMS FOR EXTENDING DYNAMIC RANGE IN ASSAYS FOR THE DETECTION OF MOLECULES OR PARTICLES," by Duffy et al.; U.S. patent application Ser. No. 13/035,472, filed Feb. 25, 2011, entitled "SYSTEMS, DEVICES, AND METHODS FOR ULTRA-SENSITIVE DETECTION OF MOLECULES OR PARTICLES," by Fournier et al.; U.S. patent application Ser. No. 13/037,987, filed Mar. 1, 2011, published as US-2011-0245097 on Oct. 6, 2011, entitled "METHODS AND SYSTEMS FOR EXTENDING DYNAMIC RANGE IN ASSAYS FOR THE DETECTION OF MOLECULES OR PARTICLES," by Rissin et al.; each herein incorporated by reference. While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B." when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either." "one of," "only one of," or "exactly one of." "Consisting essentially of," when used in the claims, shall have its ordinary meaning as used in the field of patent law.

As used herein in the specification and in the claims, the phrase "at least one." in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A method of producing a bodily fluid sample of a patient suspected of having a neurological condition containing an analytically quantified amount of an endogenous phosphorylated tau protein, said method comprising:

(A) obtaining a volume of bodily fluid comprising blood, or a blood component selected from plasma and serum, (B) diluting the volume of bodily fluid, and (C) quantifying through the use of an analytical protein concentration measurement assay a concentration of the phosphorylated tau protein in the volume of bodily fluid to produce the bodily fluid sample containing the analytically quantified amount of the endogenous phosphorylated tau protein;

wherein the analytically quantified concentration of the endogenous phosphorylated tau protein contained in the bodily fluid sample is less than about 5 pg/mL, and a limit of quantification of the analytical protein concentration measurement assay used in step (C) for quantifying the concentration of the phosphorylated tau protein is less than about 0.2 pg/mL.

2. The method of claim 1, wherein the analytical protein concentration measurement assay used in step (C) comprises:

i. exposing a plurality of capture objects that each include a binding surface having affinity for the phosphorylated tau protein to the volume of bodily fluid;

ii. immobilizing at least some molecules of the phosphorylated tau protein with respect to the plurality of capture objects such that at least some of the capture objects associate with at least one molecule of the phosphorylated tau protein and a statistically significant fraction of the capture objects do not associate with any molecules of the phosphorylated tau protein;

iii. determining a proportion of the plurality of capture objects that associated with a molecule of the phosphorylated tau protein in step ii; and iv. determining a measure of the concentration of the phosphorylated tau protein in the volume of bodily fluid based at least in part on the proportion determined in step iii.

3. The method of claim 2, wherein the plurality of capture objects comprises a plurality of beads.

4. The method of claim 1, wherein the analytical protein concentration measurement assay used in step (C) comprises spatially segregating molecules of the phosphorylated tau protein into a plurality of locations, wherein a statistically significant fraction of the locations contain a single molecule of the phosphorylated tau protein and a statistically significant fraction of the locations do not contain any molecules of the phosphorylated tau protein.

5. The method of claim 4, wherein the plurality of locations comprises a plurality of reaction vessels.

6. The method of claim 1, wherein the phosphorylated tau protein is p-tau-231.

7. The method of claim 1, wherein the phosphorylated tau protein is p-tau-181.

8. The method of claim 1, wherein the volume of bodily fluid comprises blood.

9. The method of claim 1, wherein the volume of bodily fluid comprises plasma.

10. The method of claim 1, wherein the volume of bodily fluid comprises serum.

11. The method of claim 1, wherein the volume of bodily fluid does not comprise cerebrospinal fluid (CSF).

12. The method of claim 1, wherein the patient suspected of having a neurological condition is recovering from a brain injury.

13. The method of claim 12, wherein the volume of bodily fluid has been collected from the patient within 12 hours of the brain injury.

14. The method of claim 12, wherein the brain injury results from a hypoxic event.

15. The method of claim 12, wherein the brain injury comprises a hypoxic event caused by cardiac arrest.

16. The method of claim 12, wherein the brain injury comprises a hypoxic event caused by stroke.

17. The method of claim 12, wherein the brain injury comprises a hypoxic event caused by an ischemic event.

18. The method of claim 12, wherein the brain injury comprises a hypoxic event caused by a thrombosis.

19. The method of claim 1, wherein the limit of detection for the analytical protein concentration measurement assay is less than about 0.02 pg/mL.

20. The method of claim 1, wherein the analytical protein concentration measurement assay used in step (C) comprises:
   i. suspending a plurality of capture objects that each include a binding surface having affinity for the phosphorylated tau protein in the diluted volume of bodily fluid,
   ii. immobilizing at least some molecules of the phosphorylated tau protein with respect to at least some of the plurality of capture objects suspended in the diluted volume of bodily fluid such that at least some of the capture objects associate with at least one molecule of the phosphorylated tau protein from the volume of bodily fluid,
   iii. interrogating at least some of the capture objects associated with at least one molecule of the phosphorylated tau protein from the volume of bodily fluid; and
   iv. determining a measure of the concentration of the phosphorylated tau protein in the volume of bodily fluid based at least in part on the interrogating step performed in step iii.

21. The method of claim 20, wherein the plurality of capture objects comprises a plurality of beads.

22. The method of claim 1, wherein the limit of quantification for the analytical protein concentration measurement assay is greater than or equal to about 0.01 pg/mL and less than or equal to about 0.2 pg/mL.

* * * * *